(12) United States Patent
Tucker et al.

(10) Patent No.: US 9,173,995 B1
(45) Date of Patent: Nov. 3, 2015

(54) SELF-ORIENTING SYRINGE AND SYRINGE INTERFACE

(71) Applicant: Bayer Medical Care Inc., Indianola, PA (US)

(72) Inventors: Barry L. Tucker, Verona, PA (US); Kevin P. Cowan, Allison Park, PA (US); Arthur E. Uber, III, Pittsburgh, PA (US); Edward J. Rhinehart, Monroeville, PA (US); Michael A. Spohn, Fenelton, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 14/526,294

(22) Filed: Oct. 28, 2014

(51) Int. Cl.
*A61M 37/00* (2006.01)
*A61M 5/145* (2006.01)

(52) U.S. Cl.
CPC ....... *A61M 5/14546* (2013.01); *A61M 5/14566* (2013.01); *A61M 2005/14573* (2013.01)

(58) Field of Classification Search
CPC .......... A61M 5/14546; A61M 5/1456; A61M 5/14566; A61M 5/1458; A61M 2005/14573
USPC ................................................ 604/154–155
See application file for complete search history.

(56) References Cited

U.S. PATENT DOCUMENTS

| | | |
|---|---|---|
| 1,988,480 A | 1/1935 | Lampkin |
| 2,627,720 A | 2/1953 | Glass |
| 2,734,504 A | 2/1956 | Crescas et al. |
| 2,946,331 A | 7/1960 | Jungst et al. |
| 2,956,563 A | 10/1960 | Sarnoff |
| 3,115,135 A | 12/1963 | Sarnoff |
| 3,348,545 A | 10/1967 | Sarnoff et al. |
| 3,395,704 A | 8/1968 | Frey et al. |
| 3,631,847 A | 1/1972 | Hobbs, II |
| 3,701,345 A | 10/1972 | Heilman et al. |
| 3,752,145 A | 8/1973 | Runnells et al. |
| 3,812,843 A | 5/1974 | Wootten et al. |
| 3,880,138 A | 4/1975 | Wootten et al. |
| 4,006,736 A | 2/1977 | Kranys et al. |
| 4,150,672 A | 4/1979 | Whitney et al. |
| 4,267,836 A | 5/1981 | Whitney et al. |
| 4,269,185 A | 5/1981 | Whitney et al. |
| 4,273,122 A | 6/1981 | Whitney et al. |
| 4,342,312 A | 8/1982 | Whitney et al. |
| 4,345,595 A | 8/1982 | Whitney et al. |

(Continued)

FOREIGN PATENT DOCUMENTS

| | | |
|---|---|---|
| DE | 69507018 T2 | 8/1999 |
| DE | 69416686 T2 | 10/1999 |

(Continued)

*Primary Examiner* — Edelmira Bosques
(74) *Attorney, Agent, or Firm* — Joseph L. Kent; David Schramm; James R. Stevenson

(57) ABSTRACT

A syringe includes a barrel having a proximal end, a distal end, and a sidewall extending between the proximal end and the distal end along a longitudinal axis. At least one syringe retaining member protrudes radially outwardly relative to an outer surface of the sidewall. The at least one syringe retaining member tapers axially in a direction from the distal end toward the proximal end. The at least one syringe retaining member is configured for selective engagement with a locking mechanism on a fluid injector to releasably lock the syringe with the fluid injector. A taper of the at least one syringe retaining member is configured to rotationally guide the syringe into alignment with the locking mechanism.

30 Claims, 39 Drawing Sheets

(56) References Cited

U.S. PATENT DOCUMENTS

| | | |
|---|---|---|
| 4,351,335 A | 9/1982 | Whitney et al. |
| 4,405,318 A | 9/1983 | Whitney et al. |
| 4,424,720 A | 1/1984 | Bucchianeri |
| 4,465,473 A | 8/1984 | Ruegg |
| 4,573,978 A | 3/1986 | Reilly |
| 4,634,431 A | 1/1987 | Whitney et al. |
| 4,636,198 A | 1/1987 | Stade |
| 4,677,980 A | 7/1987 | Reilly et al. |
| 4,695,271 A | 9/1987 | Goethel |
| 4,744,786 A | 5/1988 | Hooven |
| 4,854,324 A | 8/1989 | Hirschman et al. |
| 4,869,720 A | 9/1989 | Chernack |
| 4,936,833 A | 6/1990 | Sams |
| 4,966,601 A | 10/1990 | Draenert |
| 5,002,538 A | 3/1991 | Johnson |
| 5,007,904 A | 4/1991 | Densmore et al. |
| 5,098,386 A | 3/1992 | Smith |
| 5,178,609 A | 1/1993 | Ishikawa |
| 5,209,731 A | 5/1993 | Sterman et al. |
| 5,219,099 A | 6/1993 | Spence et al. |
| 5,269,762 A | 12/1993 | Armbruster et al. |
| 5,279,569 A | 1/1994 | Neer et al. |
| 5,300,031 A | 4/1994 | Neer et al. |
| 5,383,858 A | 1/1995 | Reilly et al. |
| 5,451,221 A | 9/1995 | Cho et al. |
| 5,456,669 A | 10/1995 | Neer et al. |
| 5,520,653 A | 5/1996 | Reilly et al. |
| 5,535,746 A | 7/1996 | Hoover et al. |
| 5,779,675 A | 7/1998 | Reilly et al. |
| 5,782,815 A | 7/1998 | Yanai et al. |
| 5,792,102 A | 8/1998 | Muller-Spath |
| 5,873,861 A | 2/1999 | Hitchins et al. |
| 5,944,694 A | 8/1999 | Hitchins et al. |
| 5,947,929 A | 9/1999 | Trull |
| 5,947,935 A | 9/1999 | Rhinehart et al. |
| 6,315,758 B1 | 11/2001 | Neer et al. |
| 6,336,913 B1 | 1/2002 | Spohn et al. |
| 6,368,307 B1 | 4/2002 | Ziemba et al. |
| 6,432,089 B1 | 8/2002 | Kakimi et al. |
| 6,520,930 B2 | 2/2003 | Critchlow et al. |
| 6,652,489 B2 | 11/2003 | Trocki et al. |
| 6,659,979 B2 | 12/2003 | Neer et al. |
| 6,716,195 B2 | 4/2004 | Nolan, Jr. et al. |
| 6,733,477 B2 | 5/2004 | Cowan et al. |
| 6,743,202 B2 | 6/2004 | Hirschman et al. |
| 6,958,053 B1 | 10/2005 | Reilly |
| 7,273,477 B2 | 9/2007 | Spohn et al. |
| 7,393,341 B2 | 7/2008 | Nemoto |
| 7,419,478 B1 | 9/2008 | Reilly et al. |
| 7,462,166 B2 | 12/2008 | Cowan et al. |
| 7,497,843 B1 | 3/2009 | Castillo et al. |
| 7,553,294 B2 | 6/2009 | Lazzaro et al. |
| 7,563,249 B2 | 7/2009 | Schriver et al. |
| 7,666,169 B2 | 2/2010 | Cowan et al. |
| 7,674,244 B2 | 3/2010 | Kalafut et al. |
| 7,682,345 B2 | 3/2010 | Savage |
| 7,691,085 B2 | 4/2010 | Dedig et al. |
| 7,846,136 B2 | 12/2010 | Witowski |
| 8,012,125 B1 | 9/2011 | Fago et al. |
| 8,038,651 B2 | 10/2011 | Keller |
| 8,133,203 B2 | 3/2012 | Hack |
| 8,439,876 B2 | 5/2013 | Spohn et al. |
| 8,572,834 B2 | 11/2013 | Cude |
| 8,721,596 B2 | 5/2014 | Trocki et al. |
| 2002/0128607 A1 | 9/2002 | Haury et al. |
| 2007/0219508 A1 | 9/2007 | Bisegna et al. |
| 2009/0112087 A1 | 4/2009 | Fago |
| 2011/0106015 A1 | 5/2011 | Liscio et al. |
| 2011/0208123 A1 | 8/2011 | Gray et al. |
| 2012/0016234 A1 | 1/2012 | Nemoto et al. |
| 2012/0265143 A1 | 10/2012 | Krumme et al. |
| 2013/0274655 A1 | 10/2013 | Jennings et al. |
| 2013/0281940 A1 | 10/2013 | Gelblum et al. |
| 2013/0340608 A1 | 12/2013 | Yamamoto |
| 2014/0027009 A1 | 1/2014 | Riley et al. |

FOREIGN PATENT DOCUMENTS

| | | |
|---|---|---|
| DE | 69527281 T2 | 1/2003 |
| DE | 202004005433 U1 | 8/2004 |
| DE | 102004032970 A1 | 2/2006 |
| EP | 0143895 A1 | 8/1984 |
| EP | 0346950 A2 | 6/1985 |
| EP | 0362484 A2 | 4/1990 |
| EP | 482677 B1 | 4/1998 |
| EP | 893133 B1 | 11/2002 |
| EP | 1416994 A1 | 5/2004 |
| EP | 1188669 B1 | 8/2004 |
| EP | 1465101 A2 | 10/2004 |
| EP | 1281408 B1 | 11/2004 |
| EP | 1484071 A1 | 12/2004 |
| EP | 1512423 A1 | 3/2005 |
| EP | 1531889 A1 | 5/2005 |
| EP | 1563859 A1 | 8/2005 |
| EP | 1588728 A1 | 10/2005 |
| EP | 1596908 A1 | 11/2005 |
| EP | 1642606 A1 | 4/2006 |
| EP | 1647291 A1 | 4/2006 |
| EP | 1827535 A2 | 5/2006 |
| EP | 1681069 A1 | 7/2006 |
| EP | 1688157 A1 | 8/2006 |
| EP | 1703924 A1 | 9/2006 |
| EP | 1723977 A1 | 11/2006 |
| EP | 1732093 A1 | 12/2006 |
| EP | 1736189 A1 | 12/2006 |
| EP | 1767233 A1 | 3/2007 |
| EP | 1782853 A1 | 5/2007 |
| EP | 1820523 A1 | 8/2007 |
| EP | 1820524 A1 | 8/2007 |
| EP | 1825875 A1 | 8/2007 |
| EP | 1825876 A1 | 8/2007 |
| EP | 1825877 A1 | 8/2007 |
| EP | 1896100 A2 | 3/2008 |
| EP | 1932556 A1 | 6/2008 |
| EP | 1888218 B1 | 12/2008 |
| EP | 1486219 B1 | 4/2009 |
| EP | 2015800 A4 | 5/2009 |
| EP | 2055332 A1 | 5/2009 |
| EP | 1847285 B1 | 9/2009 |
| EP | 1670522 B1 | 11/2009 |
| EP | 2187993 A1 | 5/2010 |
| EP | 2227274 A1 | 9/2010 |
| EP | 2227276 A1 | 9/2010 |
| EP | 2240219 A2 | 10/2010 |
| EP | 2244766 A1 | 11/2010 |
| EP | 2253348 A1 | 11/2010 |
| EP | 2315148 A1 | 4/2011 |
| EP | 2025356 B1 | 5/2011 |
| EP | 2318966 A2 | 5/2011 |
| EP | 2331175 A1 | 6/2011 |
| EP | 2341456 A1 | 7/2011 |
| EP | 2347359 A2 | 7/2011 |
| EP | 2353118 A1 | 8/2011 |
| EP | 2361647 A1 | 8/2011 |
| EP | 2362791 A2 | 9/2011 |
| EP | 2376146 A2 | 10/2011 |
| EP | 2384778 A1 | 11/2011 |
| EP | 2409720 A1 | 1/2012 |
| EP | 2411071 A2 | 2/2012 |
| EP | 2416821 A1 | 2/2012 |
| EP | 2427234 A1 | 3/2012 |
| EP | 2429614 A2 | 3/2012 |
| EP | 2227275 B1 | 6/2012 |
| EP | 2464402 A2 | 6/2012 |
| EP | 2337595 B1 | 7/2012 |
| EP | 2481430 A1 | 8/2012 |
| EP | 2485790 A1 | 8/2012 |
| EP | 2316509 B1 | 10/2012 |
| EP | 2363158 B1 | 11/2012 |
| EP | 2536449 A1 | 12/2012 |
| EP | 1938853 B1 | 1/2013 |
| EP | 2222358 B1 | 1/2013 |
| EP | 2275155 B1 | 4/2013 |
| EP | 2316507 B1 | 4/2013 |
| EP | 2316506 B1 | 5/2013 |

(56) References Cited

FOREIGN PATENT DOCUMENTS

| | | | |
|---|---|---|---|
| EP | 2359883 B1 | 5/2013 |
| EP | 2229199 B1 | 6/2013 |
| EP | 2416824 B1 | 6/2013 |
| EP | 2618870 A2 | 7/2013 |
| EP | 2621553 A2 | 8/2013 |
| EP | 2628496 A1 | 8/2013 |
| EP | 2363160 B1 | 9/2013 |
| EP | 2251053 B1 | 10/2013 |
| EP | 2643035 A2 | 10/2013 |
| EP | 2654843 A1 | 10/2013 |
| EP | 2665501 A1 | 11/2013 |
| EP | 1716884 B1 | 12/2013 |
| EP | 2286855 B1 | 12/2013 |
| EP | 2520318 B1 | 12/2013 |
| EP | 2671603 A1 | 12/2013 |
| EP | 2686040 A1 | 1/2014 |
| EP | 2692375 A1 | 2/2014 |
| EP | 2185227 B1 | 3/2014 |
| EP | 2707824 A2 | 3/2014 |
| EP | 2732393 A2 | 5/2014 |
| EP | 2734253 A1 | 5/2014 |
| GB | 848204 A | 9/1960 |
| GB | 1049263 A | 11/1966 |
| GB | 1576733 A | 10/1980 |
| GB | 2486690 A | 6/2012 |
| GB | 2501897 A | 11/2013 |
| JP | 4833984 B2 | 12/2011 |
| JP | 2012120934 A | 6/2012 |
| JP | 4965582 B2 | 7/2012 |
| JP | 5436897 B2 | 3/2014 |
| JP | 5518844 B2 | 6/2014 |
| WO | 0012157 A1 | 3/2000 |
| WO | 0012158 A1 | 3/2000 |
| WO | 2007130061 A1 | 11/2007 |
| WO | 2009036496 A2 | 3/2009 |
| WO | 2012124028 A1 | 9/2012 |
| WO | 2012155035 A1 | 11/2012 |

Loading

Locked

Half un-lock

Near extract

Extracting

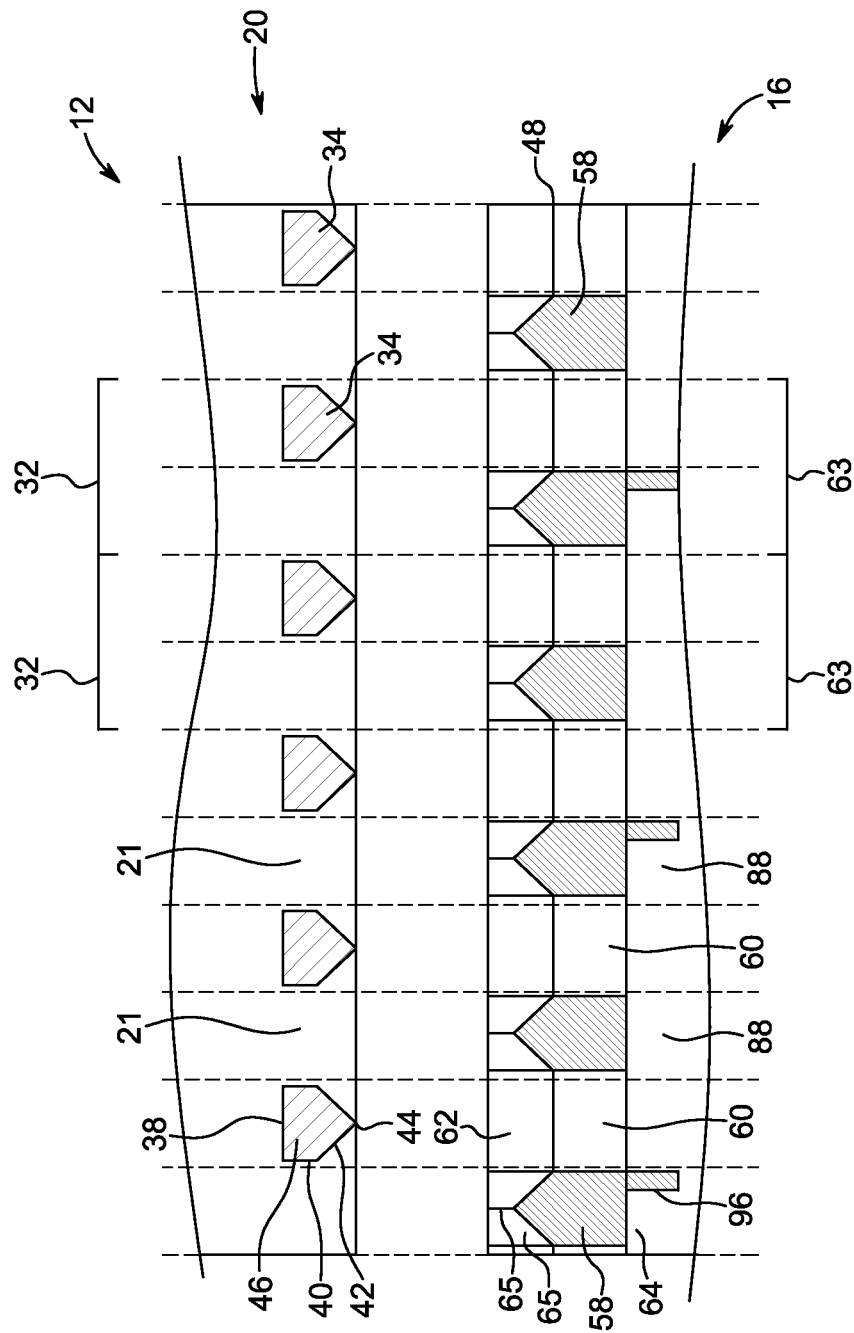

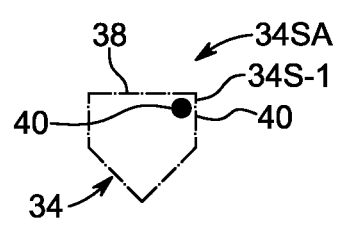
FIG. 5S(1)
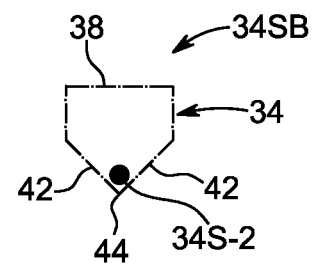
FIG. 5S(2)

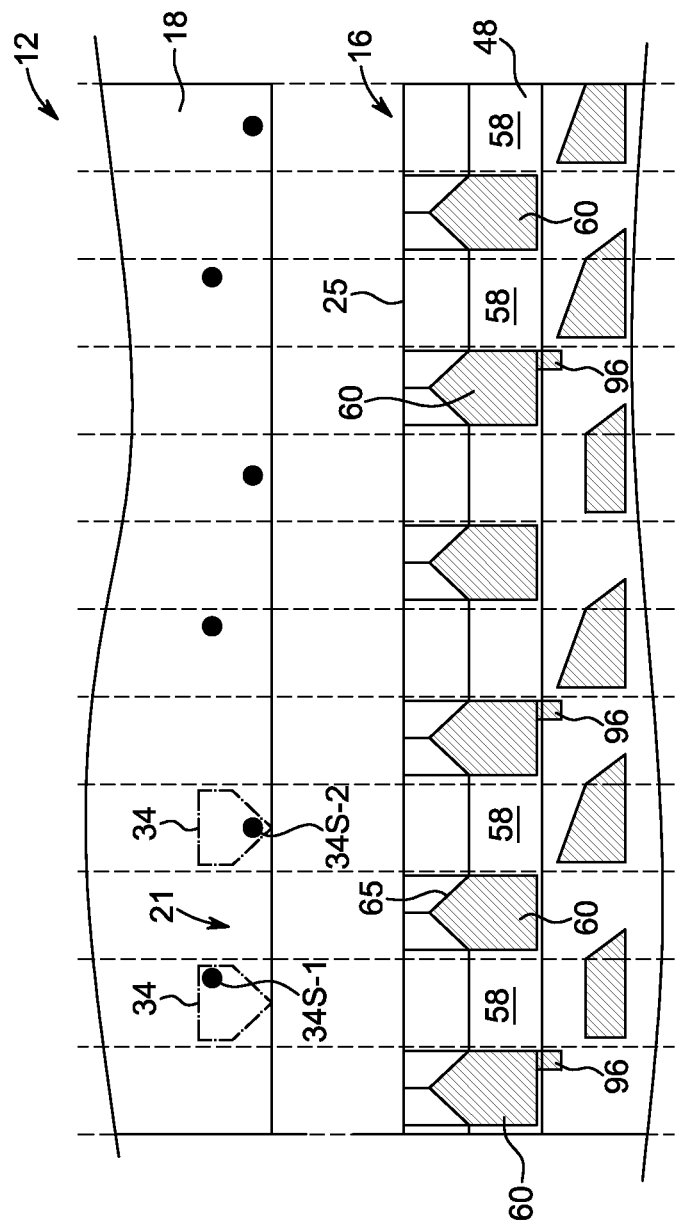
FIG. 5S(3)

SELF-ORIENTING SYRINGE AND SYRINGE INTERFACE

BACKGROUND OF THE DISCLOSURE

1. Field of the Disclosure

The present disclosure relates generally to a system including a self-orienting, front-loading syringe for use with a fluid injector and, further, to a connection interface for securing the syringe to the fluid injector and to a method for loading and removal of the syringe to and from the fluid injector.

2. Description of Related Art

In many medical diagnostic and therapeutic procedures, a medical practitioner, such as a physician, injects a patient with one or more medical fluids. In recent years, a number of injector-actuated syringes and fluid injectors for pressurized injection of medical fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other molecular imaging procedures. In general, these fluid injectors are designed to deliver a preset amount of fluid at a preset pressure and/or flow rate.

In some injection procedures, the medical practitioner places a catheter or a needle connected to tubing, or other fluid delivery connection into a vein or artery of the patient. The catheter or the tubing is connected to either a manual or to an automatic fluid injection mechanism. Automatic fluid injection mechanisms typically include at least one syringe connected to at least one fluid injector having, for example, at least one powered linear piston. The at least one syringe includes, for example, a source of contrast and/or a source of flushing fluid. The medical practitioner enters settings into an electronic control system of the fluid injector for a fixed volume of contrast and/or saline and a fixed rate of injection for each.

The injected contrast and/or saline are delivered to a patient's vasculature through the catheter or needle inserted into the patient's body, such as the patient's arm or groin area. A dose of contrast is referred to as a bolus. Once the bolus of contrast is delivered to the desired site, that area is imaged using a conventional imaging technique, such as angiography imaging or scanning, computed tomography (CT), ultrasound, magnetic resonance imaging (MRI), positron emission tomography (PET), and other molecular imaging procedures. The presence of the contrast becomes clearly visible against the background of the surrounding tissue.

Various front-loading connection interfaces have been developed to facilitate the loading and removal of the syringe to and from the fluid injector. In some embodiments, the syringe having a retention feature is inserted into a syringe port on the fluid injector by aligning the syringe with a corresponding locking feature provided on the fluid injector. It is often necessary for the medical practitioner to manually align the retention feature of the syringe with the corresponding locking feature on the fluid injector before the syringe can be loaded onto the injector. In some cases, there are only one or two possible alignments for loading, such as shown in U.S. Pat. No. 6,336,913. In these syringes, the operator must rotate the syringe to find an alignment that allows the syringe to engage the fluid injector. It is then necessary for the operator to manually rotate the syringe relative to the locking feature to create a strong enough engagement for operation of the injector. In another embodiment disclosed in U.S. Pat. No. 6,652,489, there is no need to rotationally align the syringe or to rotate the syringe for installation or engagement. To remove the syringe, the operator must rotate the syringe at least 45 degrees, and more commonly 90 degrees, about its longitudinal axis. After rotation, the operator must then physically pull the syringe out of the injector. In some embodiments, the operator must pull on the syringe at the same time while rotating the syringe. Such syringe injector features require additional time and effort to load/remove the syringe from the injector, resulting in increased time for a medical injection procedure.

Accordingly, there is a need in the art for an improved syringe and injector attachment, interface, and/or locking feature that allows the operator to more easily disengage or release the syringe from the fluid injector, for example to relieve the operator of the effort of simultaneously pulling and rotating the syringe. There is a further need in the art for reducing or eliminating the need for the operator to rotationally align the syringe with the fluid injector during engagement of the syringe with the fluid injector. While various syringe connection interfaces and methods are known in the medical field, improved syringe designs, syringe retention mechanisms, connection interfaces between the syringe and the fluid injector and methods for loading and removing the syringe to and from the fluid injector continue to be in demand.

SUMMARY OF DISCLOSURE

In view of the disadvantages of the existing connection interfaces between the syringe and the fluid injector, there is a need in the art for an improved connection interface between the syringe and the fluid injector that overcomes the deficiencies of the prior art. There is an additional need for improved syringes, syringe retention mechanisms, and methods for engaging and disengaging the syringe to and from the fluid injector so that the syringe does not have to be manually rotationally aligned about its longitudinal axis relative to the fluid injector to allow easy loading or removal/ejection of the syringe to and from the fluid injector.

In one embodiment, a syringe may include a barrel having a proximal end, a distal end, and a substantially circumferential sidewall extending between the proximal end and the distal end along a longitudinal axis. At least one syringe retaining member may protrude radially outwardly relative to an outer surface of the sidewall. The at least one syringe retaining member may taper axially along the outer surface of the sidewall in a direction from the distal end toward the proximal end. The at least one syringe retaining member may be configured for engagement with a locking mechanism on a fluid injector to releasably lock the syringe with the fluid injector. A taper of the at least one syringe retaining member may be configured to rotationally guide the syringe into self-oriented alignment with the locking mechanism and axially eject the syringe upon rotation of the syringe.

The at least one syringe retaining member may have at least one first surface tapered axially in a direction from the distal end toward the proximal end. The at least one syringe retaining member may further have a second surface configured to guide the syringe into self-oriented alignment with the locking mechanism. The first surface and the second surface on the syringe retaining member may be linear, segmented, curved, continuous, discontinuous, or planar. The second surface may be tapered axially in a direction opposite the first surface. The at least one syringe retaining member may be monolithically formed on the outer surface of the syringe. The at least one syringe retaining member may be separated from the outer surface of the syringe. The at least one syringe retaining member may have a base surface arranged substantially perpendicularly relative to the longitudinal axis. At least a portion of the at least one syringe retaining member may protrude substantially perpendicularly relative to the outer surface of the syringe. Individual syringe retaining members in the plurality of syringe retaining members may be shaped substantially the same or may have two or more different shapes.

In some embodiments, a plurality of syringe retaining members may be spaced around at least a portion of the outer surface of the syringe. The plurality of syringe retaining members may be separated at substantially equal angular intervals around the outer surface of the syringe. The plurality of syringe retaining members may be separated at unequal angular intervals around the outer surface. The plurality of syringe retaining members may be aligned longitudinally at or near the proximal end relative to the longitudinal axis. At least one of the plurality of syringe retaining members may be offset toward the proximal end of the barrel. At least one of the plurality of syringe retaining members may be offset toward the distal end of the barrel.

In some embodiments, the at least one syringe retaining member may have one or more locking tabs having at least one stop surface for preventing a rotation of the syringe within the locking mechanism. The at least one syringe retaining member may have at least one first lug and at least one second lug. The at least one first lug may be the same or different from the at least one second lug. The at least one first lug may be offset longitudinally along the longitudinal axis relative to the at least one second lug. At least one of the first lug and the second lug may have an inclined release member protruding at an angle from the outer surface of the barrel to a top surface of the at least one of the first lug and the second lug. The at least one syringe retaining member may have at least one radially inwardly recessed hollow portion and in certain embodiments at least one reinforcing member may be provided in the at least one hollow portion. A flange may protrude radially outwardly from the outer surface of the sidewall relative to the longitudinal axis and distally of the at least one syringe retaining member. The flange may extend around at least a portion of the outer surface of the sidewall. The flange may have a longitudinal stop surface for limiting a length of a longitudinal insertion of the syringe into the locking mechanism. The at least one syringe retaining member may have a shape with a triangular outline, an arrowhead-shaped outline, a rectangular outline, or a rounded outline. The at least one syringe retaining member may have a top surface shaped to correspond to the outer surface of the syringe. The at least one syringe retaining member may be configured for being received within a clearance space on the locking mechanism.

In some embodiments, a syringe may have a barrel with a proximal end, a distal end, and a sidewall extending substantially circumferentially between the proximal end and the distal end along a longitudinal axis. The syringe may have at least one syringe retaining member protruding radially outwardly relative to an outer surface of the sidewall. The at least one syringe retaining member may have at least one surface tapered axially along the outer surface of the sidewall in a direction from the distal end toward the proximal end. The at least one syringe retaining member may be configured for engagement with a locking mechanism on a fluid injector to releasably lock the syringe with the fluid injector. The at least one surface may be configured to rotationally guide the syringe into self-oriented alignment with the locking mechanism and may further be configured to axially eject the syringe upon rotation of the syringe.

In other embodiments, a syringe may have a barrel with a proximal end, a distal end, and a sidewall extending substantially circumferentially between the proximal end and the distal end along a longitudinal axis. The syringe may have at least one syringe retaining member protruding radially outwardly relative to an outer surface of the sidewall. The at least one syringe retaining member may have a first surface and a second surface, such that the first surface is offset axially and radially relative to the second surface. The at least one syringe retaining member may be configured for engagement with a locking mechanism on a fluid injector to releasably lock the syringe with the fluid injector. At least one of the first and the second surface may be configured to rotationally guide the syringe into self-oriented alignment with the locking mechanism and the first surface and the second surface may further be configured to axially eject the syringe upon rotation of the syringe.

In some embodiments, a fluid injection apparatus may include at least one syringe having a cylindrical barrel with a distal end, a proximal end, a sidewall, and a longitudinal axis extending therebetween. The barrel may have at least one syringe retaining member protruding radially outwardly from an outer surface of the sidewall. The at least one syringe retaining member may have a surface tapered axially in a direction toward the proximal end. The apparatus may further include an injector having an injector housing defining at least one syringe port for receiving the at least one syringe and a locking mechanism associated with the at least one syringe port for securing the at least one syringe within the at least one syringe port. The locking mechanism may be configured for engaging the at least one syringe retaining member of the syringe to releasably lock the at least one syringe within the at least one syringe port and to axially eject the at least one syringe from the at least one syringe port upon rotation of the syringe.

In some embodiments, the first surface may be configured to rotationally guide the at least one syringe into self-alignment alignment with the locking mechanism. The locking mechanism may include a housing having a proximal end, a distal end, and a central opening extending therebetween, a first retaining ring at the distal end of the housing, and a second retaining ring within the central opening of the housing between the proximal end and the first retaining ring. The second retaining ring may be rotatable relative to the first retaining ring to operatively engage the at least one syringe retaining member of the syringe. The first retaining ring may have at least one first recess configured to receive the at least one syringe retaining member when the proximal end of the at least one syringe is inserted into the at least one syringe port. The at least one first recess may project radially outwardly into an inner sidewall of the first retaining ring. Lateral surfaces of the at least one first recess may define a guide path for guiding a movement of the at least one syringe retaining member within the at least one first recess. The at least one first recess may have at least one guide surface for guiding the first surface of the at least one syringe into the at least one first recess. The first surface of the at least one syringe retaining member may engage at least a portion of the at least one guide surface upon movement of the at least one syringe in a proximal direction. The at least one guide surface may be angled or curved relative to the longitudinal axis in a direction from the distal end toward the proximal end. A plurality of syringe retaining members may be spaced around at least a portion of the outer surface of the sidewall of the at least one syringe, such as near the proximal end, and a plurality of first recesses may be spaced apart around at least a portion of an inner surface of the first retaining ring.

In other embodiments, the second retaining ring may have one or more locking elements on at least a portion of an inner sidewall of the second retaining ring. The one or more locking elements may extend radially outward into an inner sidewall of the second retaining ring. The one or more locking elements may be separated by one or more second recesses. The one or more second recesses may be configured to receive the at least one syringe retaining member when the proximal end of the at least one syringe is inserted through the first retaining ring. The first retaining ring may include one or more first recesses and the second retaining ring may include one or more second recesses configured for receiving the at least one syringe retaining member upon rotation of the second retaining ring into selective alignment with the one or more first recesses. At least one elastically resilient member may be coupled with the second retaining ring. At least one sensor may be operatively associated with the injector for sensing information about the syringe. The at least one sensor may be configured for reading information encoded on an encoding device on the syringe.

In some embodiments, a method of loading a syringe into a locking mechanism of a syringe port of a fluid injector may include providing a syringe having at least one syringe retaining member protruding radially outwardly from an outer surface of a syringe sidewall with at least one tapering surface tapering in a direction from a distal end toward a proximal end of the syringe, and engaging the at least one tapering surface of the syringe with at least a portion of the locking mechanism to rotationally guide the syringe into self-oriented alignment with the locking mechanism. The method may further include self-orienting the syringe within the syringe port.

These and other features and characteristics of syringes, syringe connection interfaces, and systems having syringes and/or syringe connection interfaces, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only. As used in the specification and the claims, the singular form of "a", "an", and "the" include plural referents unless the context clearly dictates otherwise.

BRIEF DESCRIPTION OF THE DRAWINGS

FIGS. 4A-4M show cylindrical plan projection views of connection interfaces for securing a syringe to a fluid injector according to various other embodiments;

DETAILED DESCRIPTION

Figure 1A:
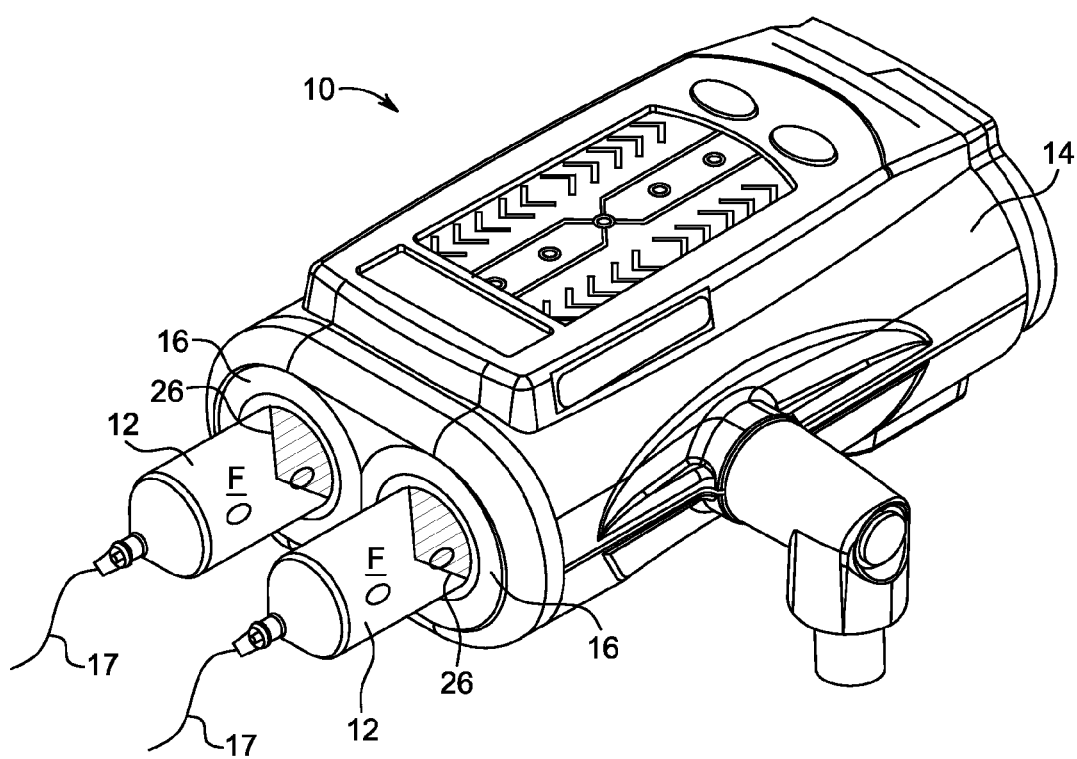
FIG. 1A is a schematic view of a system including a fluid injector and a syringe according to an embodiment of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe, the term "proximal" refers to a portion of a syringe nearest the to an injector when a syringe is oriented for connecting to an injector. The term "distal" refers to a portion of a syringe farthest away from an injector when a syringe is oriented for connecting to an injector. The term "radial" refers to a direction in a cross-sectional plane normal to a longitudinal axis of a syringe extending between proximal and distal ends. The term "circumferential" refers to a direction around an inner or outer surface of a sidewall of a syringe. The term "axial"

refers to a direction along a longitudinal axis of a syringe extending between the proximal and distal ends. The term "self-orienting" means that a syringe orients itself to the correct orientation within a syringe port during insertion without effort by a technician. The terms "axial taper", "axial tapering", and "tapering axially" mean an angle of inclination of at least one virtual or real surface on a syringe in a cylindrical plan projection view in a direction from a distal end toward a proximal end of a syringe. It is to be understood, however, that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments (i.e., aspects, variants, variations) disclosed herein are not to be considered as limiting.

Referring to the drawings in which like reference characters refer to like parts throughout the several views thereof, the present disclosure is generally directed to syringe and a connection interface for connecting a syringe to a fluid injector.

With reference to FIG. 1A, a fluid injector 10 (hereinafter referred to as "injector 10"), such as an automated or powered fluid injector, is adapted to interface with and actuate at least one syringe 12, each of which may be independently filled with a medical fluid F, such as contrast media, saline solution, or any desired medical fluid. The injector 10 may be used during a medical procedure to inject the medical fluid into the body of a patient by driving a plunger 26 of the at least one syringe 12 with at least one piston. The injector 10 may be a multi-syringe injector, wherein several syringes 12 may be oriented in a side-by-side or other relationship and include plungers 26 separately actuated by respective pistons associated with the injector 10. In embodiments with two syringes arranged in a side-by-side relationship and filled with two different medical fluids, the injector 10 may be configured to deliver fluid from one or both of the syringes 12.

The injector 10 may be enclosed within a housing 14 formed from a suitable structural material, such as plastic or metal. The housing 14 may be of various shapes and sizes depending on the desired application. For example, the injector 10 may be a free-standing structure configured to be placed on the floor or may be a smaller design for placement on a suitable table or support frame. The injector 10 includes at least one syringe port 16 for connecting the at least one syringe 12 to respective piston elements. As will be described hereinafter, in some embodiments, the at least one syringe 12 includes at least one syringe retaining member configured for retaining the syringe 12 within the syringe port 16 of the injector 10. The at least one syringe retaining member is configured to operatively engage a locking mechanism provided on or in the syringe port 16 of the injector 10 to facilitate self-oriented loading and/or removal of the syringe 12 to and from the injector 10, as will be described herein. The syringe retaining member and the locking mechanism together define a connection interface for connecting the syringe 12 to the injector 10.

At least one fluid path set 17 may be fluidly connected with the at least one syringe 12 for delivering medical fluid F from the at least one syringe 12 to a catheter, needle, or other fluid delivery connection (not shown) inserted into a patient at a vascular access site. Fluid flow from the at least one syringe 12 may be regulated by a fluid control module (not shown). The fluid control module may operate various, pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. One embodiment of a suitable front-loading fluid injector that may be modified for use with the above-described system including at least one syringe and at least one syringe interface for self-oriented loading and releasable retaining of the at least one syringe with the fluid injector described herein with reference to FIG. 1A is disclosed in U.S. Pat. No. 5,383,858 to Reilly et al. which is incorporated by reference in its entirety. Another embodiment of relevant multi-fluid delivery systems that may be modified for use with the present system are found in U.S. Pat. No. 7,553,294 to Lazzaro et al.; U.S. Pat. No. 7,666,169 to Cowan et al.; International Patent Application No. PCT/US2012/037491 (published as WO 2012/155035); and United States Patent Application Publication No. 2014/0027009 to Riley et al.; all of which are assigned to the assignee of the present application, and the disclosures of which are incorporated herein by reference. Other embodiments may include new fluid injector systems designed to include various embodiments of the interface described herein.

Figure 1B:
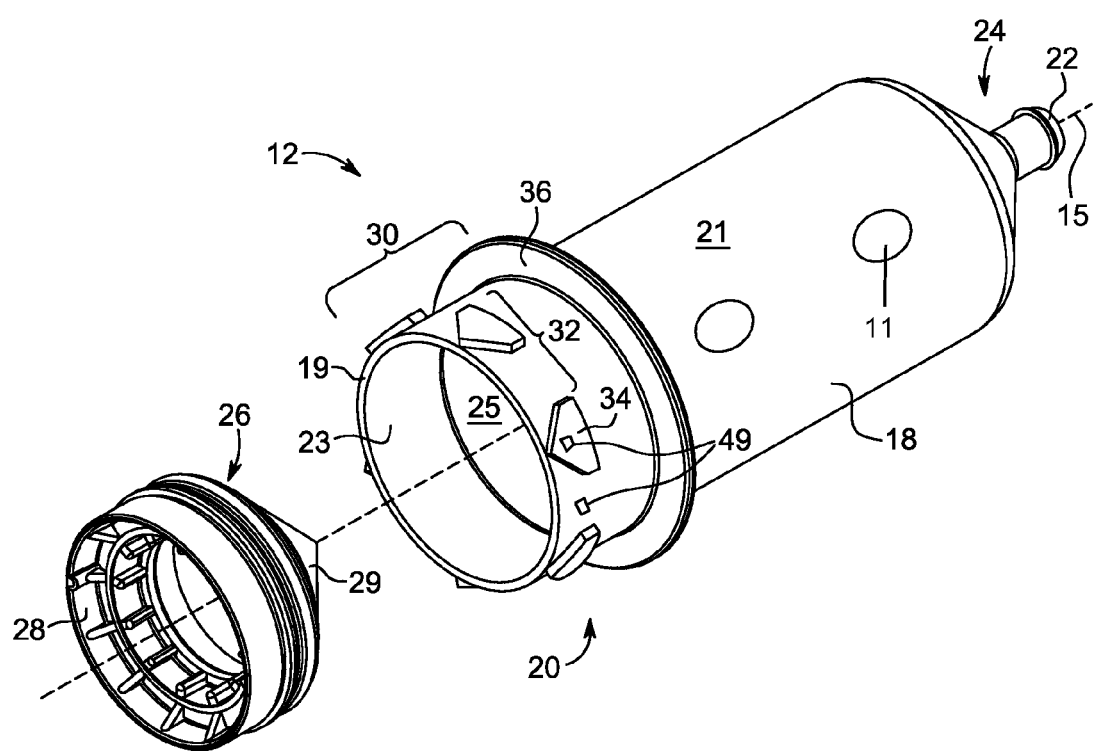
FIG. 1B is a perspective view of a syringe according to one embodiment of the present disclosure.

Having described the general structure and function of the injector 10, the at least one syringe 12 will now by discussed in greater detail. With reference to FIG. 1B, the syringe 12 generally has a cylindrical syringe barrel 18 formed from glass, metal, or a suitable medical-grade plastic. The barrel 18 has a proximal end 20 and a distal end 24, with a sidewall 19 extending therebetween along a length of a longitudinal axis 15 extending through a center of the barrel 18. The barrel 18 may be made from a transparent or translucent material, and may include at least one fluid verification member 11 for verifying a presence of the fluid F within the syringe barrel 18. A nozzle 22 extends from the distal end 24 of the barrel 18. The barrel 18 has an outer surface 21 and an inner surface 23 that defines an interior volume 25 configured for receiving the fluid therein. The proximal end 20 of the barrel 18 may be sealed with the plunger 26 that is slidable through the barrel 18. The plunger 26 forms a liquid-tight seal against the inner surface 23 of sidewall 19 of the barrel 18 as it is advanced therethrough. The plunger 26 may have a rigid inner element 28 configured for engagement with the piston of the injector 10. The plunger 26 may further include an elastomeric cover 29 disposed over at least a portion of the rigid inner element 28. The elastomeric cover 29 is configured to engage the inner surface 23 of the barrel 18 and provide a liquid-tight seal against the sidewall 19 of the barrel 18 as it is advanced therethrough.

A drip flange 36 may extend radially outward from the outer surface 21 of the syringe barrel 18 relative to the longitudinal axis 15. The drip flange 36 may extend around at least a portion of the outer circumference of the barrel 18. In one embodiment, the drip flange 36 is positioned distally along the longitudinal axis 15 relative to a syringe retaining member 32. The drip flange 36 may be configured to prevent fluid that drips from the nozzle 22 from entering the syringe port 16 on the injector 10. In this manner, the drip flange 36 helps reduce the amount of fluid that may enter the syringe port 16 and jam or otherwise interfere with the connection interface 100 (shown in FIG. 2A) and/or the interior mechanics and electronics of the injector 10. In some embodiments, the drip flange 36 defines a longitudinal stop surface that delimits the insertion section 30 of the syringe 12 (see FIG. 1B). The drip flange 36 may be formed integrally with the barrel 18 or it may be affixed or otherwise secured to the outer surface 21 of the barrel 18 using, for example, a frictional fit and/or an adhesive, welding, or by molding. In other embodiments, the drip flange 36 may be formed on the outer surface 21 of the barrel 18 by etching, laser cutting, or machining.

With continued reference to FIG. 1B, the proximal end 20 of the syringe 12 is sized and adapted for being removably inserted in the syringe port 16 of the injector 10 (shown in FIG. 1A). In some embodiments, the proximal end 20 of the syringe 12 defines an insertion section 30 that is configured to be removably inserted into the syringe port 16 of the injector 10 while the remaining portion of the syringe 12 remains outside of the syringe port 16. As will be described in detail herein, in certain embodiments, the proximal end 20 of the syringe 12 includes one or more syringe retaining members 32 adapted to form a locking engagement with a corresponding locking mechanism in the syringe port 16 of the injector 10 for releasably retaining the syringe 12 in the syringe port 16. The combination of the syringe having the one or more syringe retaining members 32 and the locking mechanism 35 (shown in FIG. 2A) of the injector 10 defines a connection interface for loading and unloading the syringe 12 to and from the injector 10. In some embodiments, at least a portion of the one or more syringe retaining members 32 may cooperate with at least a portion of the locking mechanism to self-orient the syringe 12 relative to the syringe port 16 such that the syringe 12 may be releasably inserted into and locked with the syringe port 16.

With reference to FIGS. 2A-2D, a connection interface 100 for loading and unloading the at least one syringe 12 (FIG. 1B) from the at least one syringe port 16 of the injector 10 (shown in FIG. 1A) is shown in accordance with one embodiment. The syringe 12 and the injector 10 include the connection interface 100 having at least one syringe retaining member 32 provided on the syringe 12 and a corresponding locking mechanism 35 provided on the syringe port 16 of the injector 10. In one embodiment, the at least one syringe retaining member 32 is provided on or near the proximal end 20 of the syringe barrel 18 and/or on at least a part of the insertion section 30. For example, the at least one syringe retaining member 32 may be provided on an outer surface 21 of the syringe barrel 18 on at least a portion of the insertion section 30. The at least one syringe retaining member 32 may be formed integrally with the barrel 18 or it may be affixed or otherwise secured to the outer surface 21 of the barrel 18 using, for example, a frictional fit and/or an adhesive, welding, or by molding. In other embodiments, the at least one syringe retaining member 32 may be formed on the outer surface 21 of the barrel 18 by etching, laser cutting, or machining.

Referring to FIG. 1B, the at least one syringe retaining member 32 may be formed as including one or more lugs 34 that protrude radially outwardly from the outer surface 21 of the syringe barrel 18 relative to the longitudinal axis 15. In some embodiments, a plurality of lugs 34 may be separated radially about the circumference of the barrel 18. In such embodiments, the lugs 34 are separated from each other by portions of the outer surface 21 of the barrel 18. Together, each lug 34 and the outer surface 21 of the barrel 18 on one radially adjacent side (left or right) of the lug 34 define the syringe retaining member 32. In embodiments where more than two lugs 34 are provided, the lugs 34 may be evenly or unevenly spaced apart in a radial direction on the outer surface 21 of the barrel 18. In one exemplary and non-limiting embodiment with six syringe retaining members 32 having equal angular separation therebetween, such as shown in FIG. 1B, each syringe retaining member 32 extends over 60 degrees and is therefore separated by 60 degrees from syringe retaining member 32 adjacent on either side. In such embodiment, each lug 34 may extend over 30 degrees of the circumference of the barrel 18 while the portion of the outer surface 21 of the barrel 18 that defines the remainder of the syringe retaining member 32 extends over the remaining 30 degrees. In other embodiments, each lug 34 may extend at an angle α (shown in FIG. 2B), which may be more than 30 degrees or less than 30 degrees of the circumference of the barrel 18. Similarly, each portion of the outer surface 21 of the barrel 18 between adjacent lugs 34 may extend at an angle β (shown in FIG. 2B), which may be more than 30 degrees or less than 30 degrees of the circumference of the barrel 18. In some embodiments, the syringe retaining members 32 may have unequal angular extension and/or unequal angular spacing between the syringe retaining members 32 about the outer circumference of the barrel 18. Furthermore, the one or more syringe retaining members 32 may be aligned longitudinally along the longitudinal axis 15 from the proximal end 20. In other embodiments, at least one lug 34 may be offset longitudinally relative to the remaining lugs in a direction toward the proximal end 20 or the distal end 24. In an embodiment in which one or more lugs 34 is absent, the corresponding syringe retaining member 32 can be defined by the clearance surface(s) which is the outer surface 21 of the barrel 18 between adjacent lugs 34. While embodiments having each syringe retaining member 32 extending over 60 degrees are exemplified in the attached drawings, syringes with retaining members 32 having other angles of separation, for example 360/x degrees where x is value from 1 and 36, are also within the scope of the present disclosure.

Figure 2A:
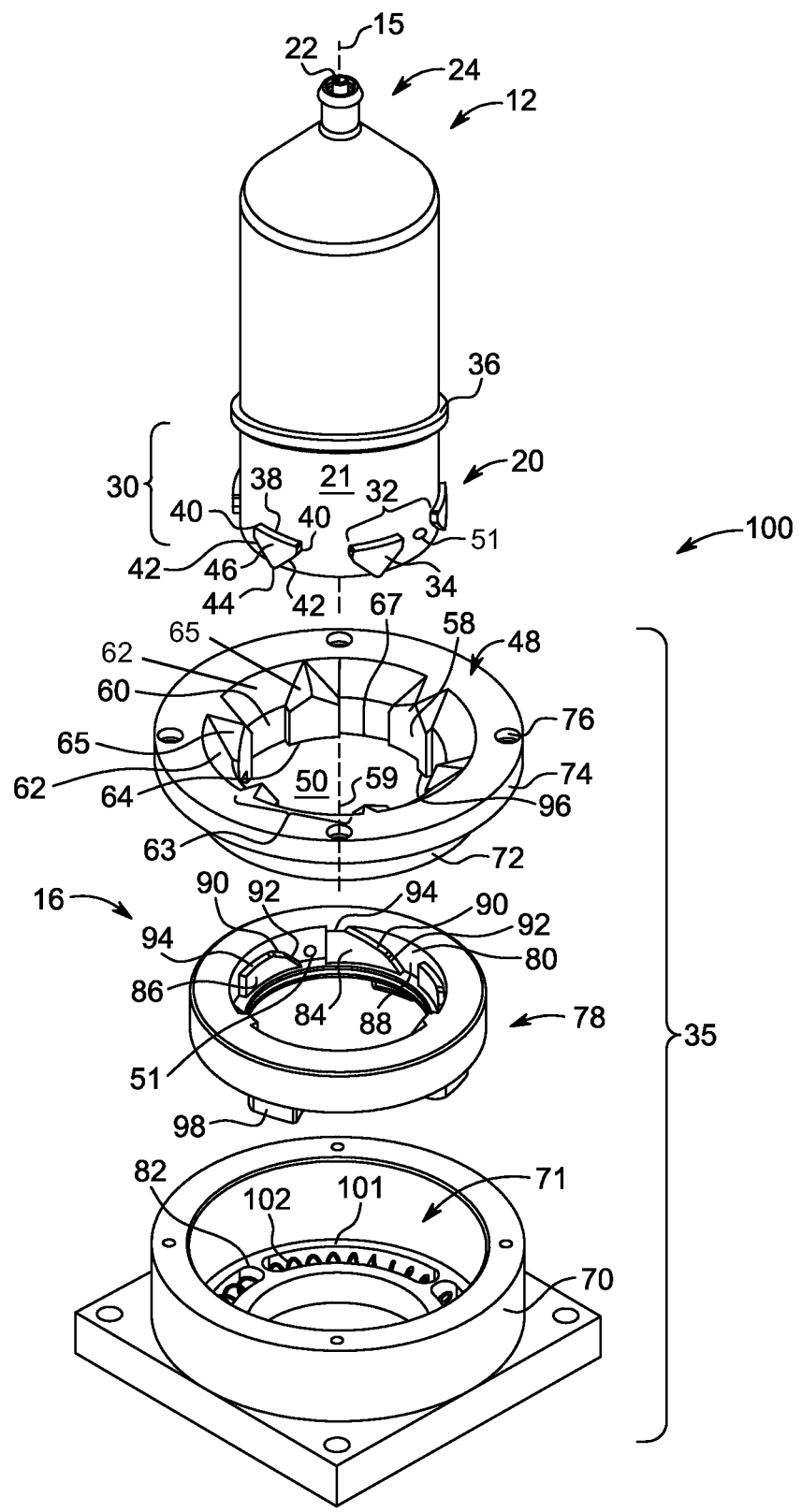
FIG. 2A is an exploded perspective view of a connection interface for securing a syringe to a fluid injector according to one embodiment.
Figure 2B:
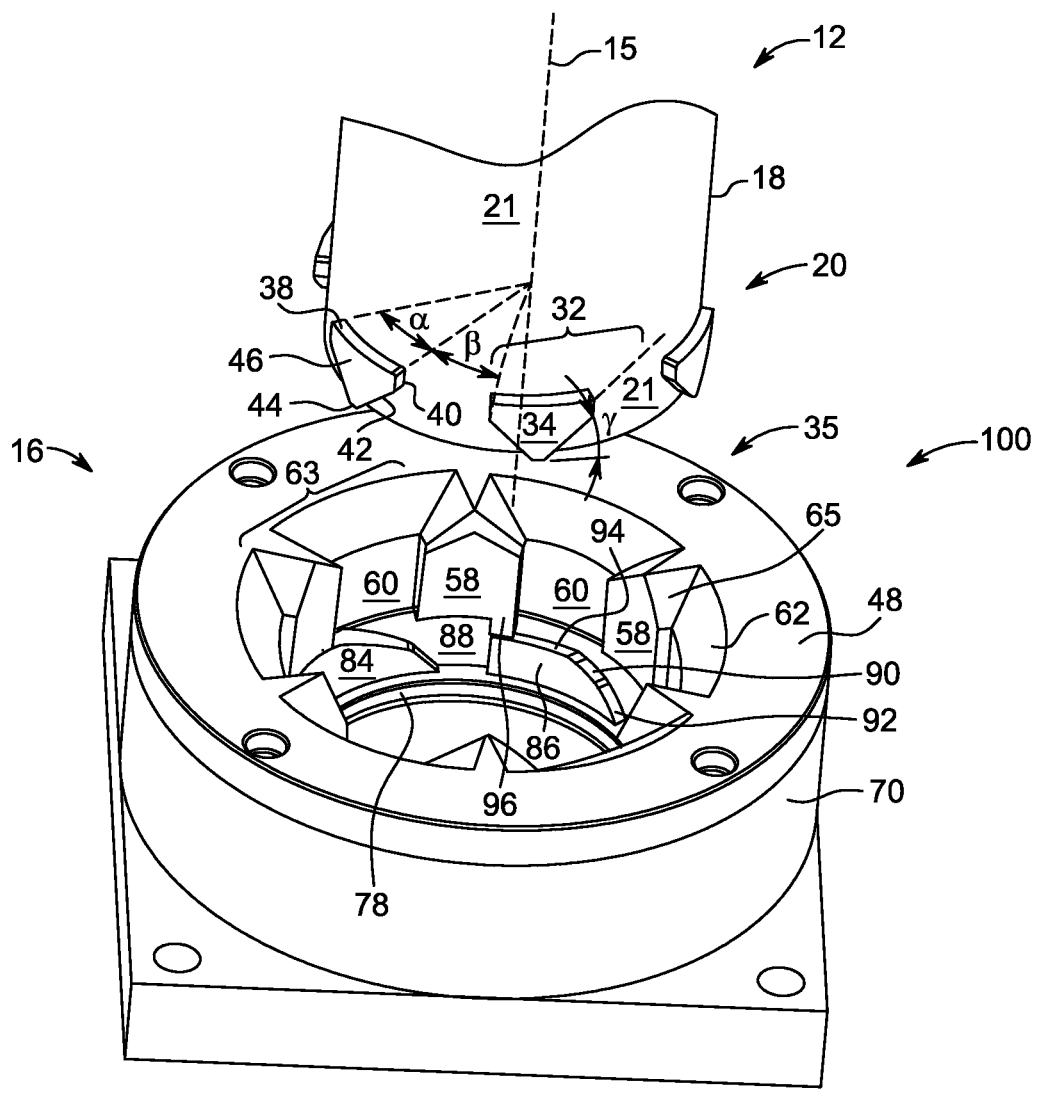
FIG. 2B is a detailed perspective view of the assembled connection interface shown in FIG. 2A.

With reference to FIGS. 2A-2B, each of the one or more lugs 34 may have a generally triangular, rectangular, polygonal, or arrowhead shape. The one or more lugs 34 protrude radially outwardly from the outer surface 21 of the barrel 18 in a direction substantially perpendicular to the outer surface 21. In some embodiments, the one or more lugs 34 or portions of lugs 34 protrude radially outwardly from the outer surface 21 of the barrel 18 at an obtuse or acute angle between the outer surface 21 of the barrel 18 and a top surface 46 of the one or more lugs 34. In some embodiments, the lugs 34 may have an identical shape to each other. In other embodiments, at least one of the lugs 34 may have a shape different from a shape of the remaining lugs 34.

In some embodiments, each of the one or more lugs 34 has a base surface 38 that may be substantially perpendicular to the longitudinal axis 15 of the barrel 18 in a radial cross-sectional plane. In other embodiments, the base surface 38 may be angled relative to the direction of the longitudinal axis 15 as it extends around the outer circumference of the barrel 18 in a radial cross-sectional plane. The base surface 38 may be planar, segmented, arcuate, curved, or a combination thereof. In some embodiments, the base surface 38 may have a plurality of individual sections that together define the base surface 38. The plurality of individual sections of the base surface 38 may define a surface that may be planar, segmented, arcuate, curved, or a combination thereof.

In certain embodiments, at least one first surface 40 may extend from at least one end of the base surface 38 in a direction substantially parallel or tapered to the longitudinal axis 15. With reference to FIG. 2B, a pair of first surfaces 40 is shown on opposite ends of the base surface 38. In some embodiments, at least one first surface 40 may be tapered axially relative to the longitudinal axis 15 in a proximal or a distal direction of the longitudinal axis 15. The axial tapering of the at least one first surface 40 relative to the longitudinal axis 15 may be defined as an angle of inclination of the first surface 40 in a cylindrical plan projection view in a direction from the distal end 24 toward the proximal end 20. The first surfaces 40 may be tapered in a same direction or opposite directions relative to the direction of the longitudinal axis 15. The at least one first surface 40 may be directly connected with the base surface 38. In some embodiments, at least one first surface 40 may be disconnected from the base surface 38. The at least one first surface 40 may be planar, segmented, arcuate, curved, or a combination thereof. In some embodiments, the at least one first surface 40 may have a plurality of individual sections that together define the at least one first surface 40. The plurality of individual sections of the at least one first surface 40 may define a surface that may be planar, segmented, arcuate, curved, or a combination thereof.

At least one second surface 42 extends from at least one first surface 40 or the base surface 38. With reference to FIG. 2B, a pair of second surfaces 42 is shown extending from the proximal ends of first surfaces 40. In some embodiments, at least one second surface 42 may be tapered axially and circumferentially (and optionally radially) relative to the longitudinal axis 15 in a proximal or a distal direction of the longitudinal axis 15. In some embodiments, at least one second surface 42 may be tapered axially relative to the longitudinal axis 15 in a proximal direction. The axial and circumferential tapering of the at least one second surface 42 relative to the longitudinal axis 15 may be defined as an angle of inclination of the second surface 42 in a cylindrical plan projection view in a direction from the distal end 24 toward the proximal end 20. For example, the at least one second surface 42 may be tapered at an angle γ (shown in FIG. 2B) relative to a plane normal to the longitudinal axis 15. Each of the second surfaces 42 may be tapered at a same or different angle γ relative to the plane normal to the longitudinal axis 15. The second surfaces 42 may join together at a rounded or a sharp point 44. At least one second surface 42 may be directly connected with at least one of the first surface 40, the base surface 38, and the point 44. In some embodiments, at least one second surface 42 may be disconnected from at least one of the first surface 40, the base surface 38, and the point 44. In some embodiments, the pair of second surfaces 42 may be omitted such that only the first surfaces 40 may join at the rounded or sharp point 44. In other embodiments, the rounded or sharp point 44 may be disconnected from the first surfaces 40 or the second surfaces 42. The at least one second surface 42 may be planar, segmented, arcuate, curved, or a combination thereof. In some embodiments, the at least one second surface 42 may have a plurality of individual sections that together define the at least one second surface 42. The plurality of individual sections of the at least one second surface 42 may define a surface that may be planar, segmented, arcuate, curved, or a combination thereof.

The base surface 38, the first and second surfaces 40, 42, and the point 44 define a border or an outline of the top surface 46 of each of the one or more lugs 34. In some embodiments, the top surface 46 may be shaped to correspond to the curvature of the syringe barrel 18. In other embodiments, the top surface 46 of one or more of the lugs 34 may be angled relative to the outer surface 21 of the syringe barrel 18 such that a first end of the top surface 46 is higher than a second end of the top surface 46 relative to the surface of the syringe barrel 18. The top surface 46 may be continuous and uninterrupted, or it may be comprised of a plurality of separate surfaces that together define the top surface 46. The top surface 46 may be planar, segmented, arcuate, curved, or a combination thereof. In some embodiments, the base surface 38, the first and second surfaces 40, 42, and the point 44 define a border or an outline of the lug 34 having a generally arrowhead shape shown in FIGS. 2A-2B.

With reference to FIGS. 2A-2D, according to one embodiment, the syringe port 16 of the injector 10 (shown in FIG. 1A) has a locking mechanism 35 configured to operatively engage the at least one syringe retaining member 32 of the syringe 12. Referring initially to FIG. 2A, the locking mechanism 35 includes a housing 70 with a central opening 71 configured to receive the proximal end 20 of the syringe 12. The housing 70 may be formed as part of the housing 14 of the injector 10 (shown in FIG. 1A) or as a fitted attachment to the housing 14 of injector 10. A first retaining ring 48 is secured to a distal end of the housing 70 such that the central opening 71 of the housing 70 is aligned with a central opening 50 of the first retaining ring 48. The first retaining ring 48 has a body 72 having a radially extending flange 74. At least a portion of the body 72 extends away from the flange 74 in a proximal direction. When installed on the housing 70, the flange 74 engages a top portion of the housing 70 and is secured by one or more fasteners (not shown) extending through one or more fastener openings 76. At least a portion of the body 72 of the first retaining ring 48 is inserted into the central opening 71 of the housing 70. In other embodiments, the first retaining ring 48 may be secured to the housing 70 by other mechanical fastening arrangements, such as a clip, screws, adhesives, welding, or snap fit. When installed on the housing 70, a central axis 59 of the first retaining ring 48 is coaxial with a central axis of the housing 70.

With continuing reference to FIG. 2A, an inner portion of a sidewall 58 within the central opening 50 of the first retaining ring 48 has one or more first recesses 60 that are configured to receive the one or more lugs 34 of the syringe 12 when the insertion section 30 of the syringe 12 is inserted through the central opening 50 of the first retaining ring 48. The one or more first recesses 60 may be evenly spaced about the inner circumference of the sidewall 58. In such embodiments, the first recesses 60 are separated from each other by portions of the sidewall 58 of the first retaining ring 48. Together, each first recess 60 and the sidewall 58 of the first retaining ring 48 on one radially adjacent side (left or right) of the first recess 60 define a clearance space 63 for receiving the syringe retaining member 32 on the syringe 12. The first recess 60 of each clearance space 63 may be configured to receive at least one lug 34 of the syringe retaining member 32, while the sidewall 58 of the first retaining ring 48 may be configured to receive a portion of the outer surface 21 of the barrel 18 when the syringe retaining member 32 is inserted into the clearance space 63. For example, in an embodiment where the first retaining ring 48 has six clearance spaces 63 equally separated about the circumference of the first retaining ring 48, each clearance space 63 is separated 60 degrees apart from the clearance spaces 63 adjacent on either side. In such embodiments, each first recesses 60 may extend over 30 degrees of the circumference of the first retaining ring 48 while the portion of the sidewall 58 of the first retaining ring 48 that defines the remainder of the clearance space 63 extend over the remaining 30 degrees of the circumference. In other embodiments, the first retaining ring 48 may include 1-5 or 7-12 or more clearance spaces 63 wherein each first recess 60 may extend over more than 30 degrees or less than 30 degrees of the circumference of the sidewall 58 of the first retaining ring 48. In some embodiments, the number of lugs 34 on the syringe 12 corresponds to the number of first recesses 60 on the retaining ring 48. In other embodiments, the number of lugs 34 on the syringe 12 is smaller than the number of first recesses 60 on the retaining ring 48. In such embodiments, the lugs 34 on the syringe 12 are spaced apart along an outer circumference of the syringe barrel 18 such that each lug 34 can be aligned with a corresponding first recess 60 on the retaining ring 48. In other embodiments, the number of lugs 34 on the syringe 12 is higher than the number of first recesses 60 on the retaining ring 48 such that more than one lug 34 may be received within at least one first recess 60.

Each of the one or more first recesses 60 extends radially outward into the inner portion of the sidewall 58 relative to the central axis 59. The lateral surfaces of each first recess 60 define a travel path for guiding the movement of the lug 34 in and out of the first recess 60 as the insertion section 30 of the syringe 12 is inserted into and out of the first retaining ring 48. Each first recess 60 extends substantially parallel along a direction of the central axis 59. In some embodiments, each first recess 60 may have one or more guiding surfaces 62 and 65 that guide the lugs 34 into self-oriented alignment with the first recesses 60 such that the lugs 34 can be inserted into the first recesses 60 and self-align the syringe 12 within syringe port 16 without any guidance or effort of the technician. The guiding surfaces 62 and 65 may be inclined radially and axially toward an opening of the first recess 60 to self-orient and guide the movement of the second surfaces 42 of the lugs 34. In some embodiments, the guiding surfaces 65 may be pointed axially such that a first portion of the guiding surface 65 is inclined toward one of the first recesses 60 while a second portion of the guiding surface 65 is inclined toward an adjacent first recess 60. The one or more guiding surfaces 62 and 65 aid in self-orienting the syringe 12 as it is inserted into the syringe port 16 by guiding the one or more lugs 34 of the syringe 12 into the corresponding one or more first recesses 60 on the syringe port 16. In this manner, a syringe 12 whose longitudinal axis 15 may be axially misaligned with the axis 59 of the syringe port 16 and the one or more lugs 34 which may be initially misaligned with the corresponding one or more first recesses 60 in a rotational direction about the longitudinal axis 15 of the syringe 12 are brought in alignment axially with the syringe port 16 and rotationally with the one or more first recesses 60 by interaction of at least the second surfaces 42 of the lugs 34 and the one or more guiding surfaces 62 and 65. The one or more first recesses 60 may have a bottom surface 67 that is substantially perpendicular to the central axis 59. In some embodiments, the bottom surface 67 may be angled or tapered in a radial direction.

With continued reference to the embodiment in FIG. 2A, the locking mechanism 35 may further include a second retaining ring 78 having a substantially annular shape with an inner sidewall 80. The second retaining ring 78 is disposed within the central opening 71 of the housing 70 between a proximal end of the body 72 of the first retaining ring 48 and a bottom 82 of the housing 70. As detailed further herein, the second retaining ring 78 is rotatable relative to the first retaining ring 48 and the housing 70, which are fixed relative to each other. The second retaining ring 78 may have one or more first locking elements 84 and, optionally, one or more second locking elements 86 disposed on at least a portion of the inner sidewall 80. The one or more first and second locking elements 84, 86 may be arranged in an alternating manner such that each first locking element 84 has a second locking element 86 provided on either side of it along the circumference of the inner sidewall 80. In other embodiments, at least one second locking element 86 is provided for a plurality of first locking elements 84. In some embodiments, the total number of first and second locking elements 84, 86 may correspond to the total number of first recesses 60 and/or the at least one syringe retaining member 32 of the syringe 12. In other embodiments, the total number of first and second locking elements 84, 86 may correspond to a multiple or fraction of the number of at least one syringe retaining members 32 of the syringe 12.

The one or more first and second locking elements 84, 86 extend radially outward from the inner sidewall 80 of the second retaining ring 78 and are separated by one or more second recesses 88. The one or more second recesses 88 are configured to receive the one or more lugs 34 of the syringe 12 when the insertion section 30 of the syringe 12 is inserted through the central opening 50 of the first retaining ring 48. The one or more second recesses 88 are arranged around a circumference of the inner sidewall 80 of the second retaining ring 78 such that the one or more second recesses 88 may be selectively aligned with the one or more first recesses 60 on the first retaining ring 48. For example, in an embodiment where the first retaining ring 48 has six first recesses 60 equally separated about the housing 70, the second retaining ring 78 may also have six second recesses 88 equally separated apart (i.e., separated by 60 degrees) from the second recesses 88 adjacent on either side.

With reference to FIG. 2B, the one or more first locking elements 84 have a first inclined surface 90 configured for engaging at least the second surface 42 of the at least one lug 34. The first inclined surface 90 may be linear, segmented, curved, or a combination thereof. The one or more first locking elements 84 may have a second inclined surface 92 additionally configured to engage at least one of the point 44, the first surface 40, and/or the second surface 42 of the lugs 34. Similarly, the one or more second locking elements 86 may have a second inclined surface 92 configured to engage at least one of the point 44, the first surface 40, and/or the second surface 42 of the lugs 34. The second inclined surface 92 may be linear, segmented, curved, or a combination thereof. The first inclined surface 90 on the one or more second locking elements 86 may transition to a linear top surface 94 that is substantially parallel to a top surface of the second retaining ring 78. The angle and profile of the first inclined surface 90 of the one or more first locking elements 84 may be the same as or different than the second inclined surface 92 of the locking elements 84 and 86. In some embodiments, only a first inclined surface 90 may be provided in linear, segmented, curved, or combination form.

Figure 2C:
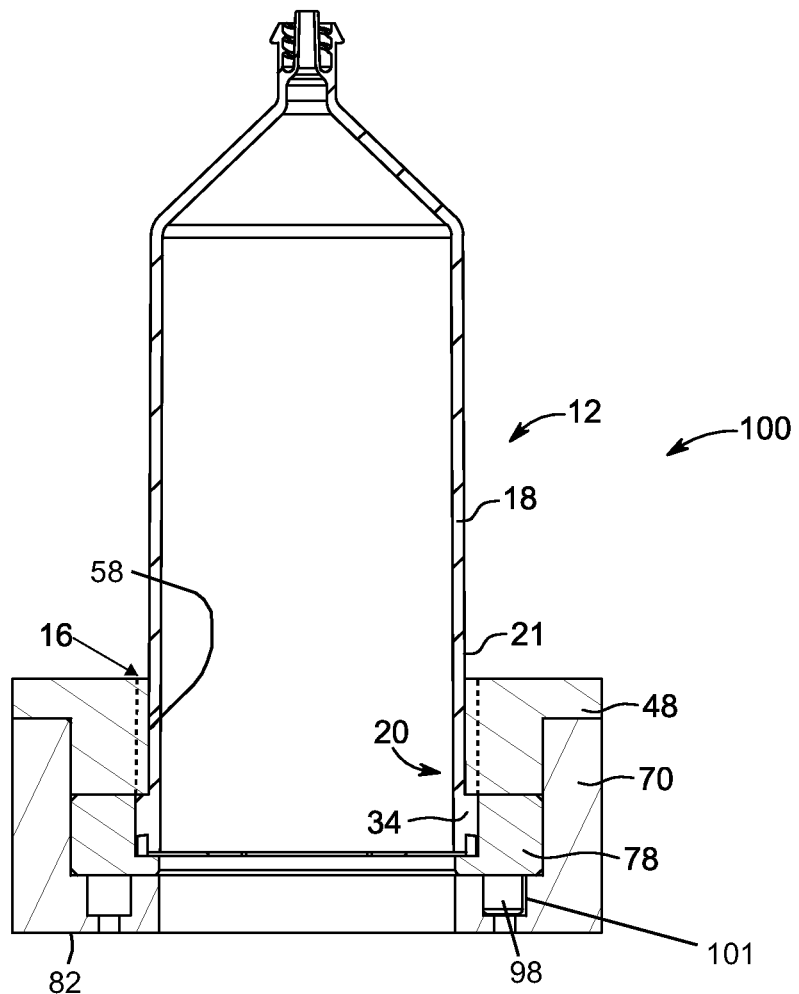
FIG. 2C is a cross-sectional view of the connection interface shown in FIG. 2A with a syringe loaded into a syringe port.

With continuing reference to FIGS. 2C-2B, the one or more first locking elements 84 may extend higher along the inner sidewall 80 relative to the one or more second locking elements 86. The linear top surface 94 of the one or more second locking elements 86 may be positioned lower relative to the top of the one or more first locking elements 84 in order to accommodate the relative sliding movement of one or more locking tabs 96 extending proximally from the first retaining ring 48. The one or more locking tabs 96 define a rotational stop surface for one or more lugs 34 once the syringe 12 is inserted into the syringe port 16. In other embodiments, the one or more locking tabs 96 may be provided separately from the one or more second locking elements 86. In some embodiments, the one or more locking tabs 96 may be provided on the syringe and/or at least one of the lugs 34, as described herein.

Figure 2D:
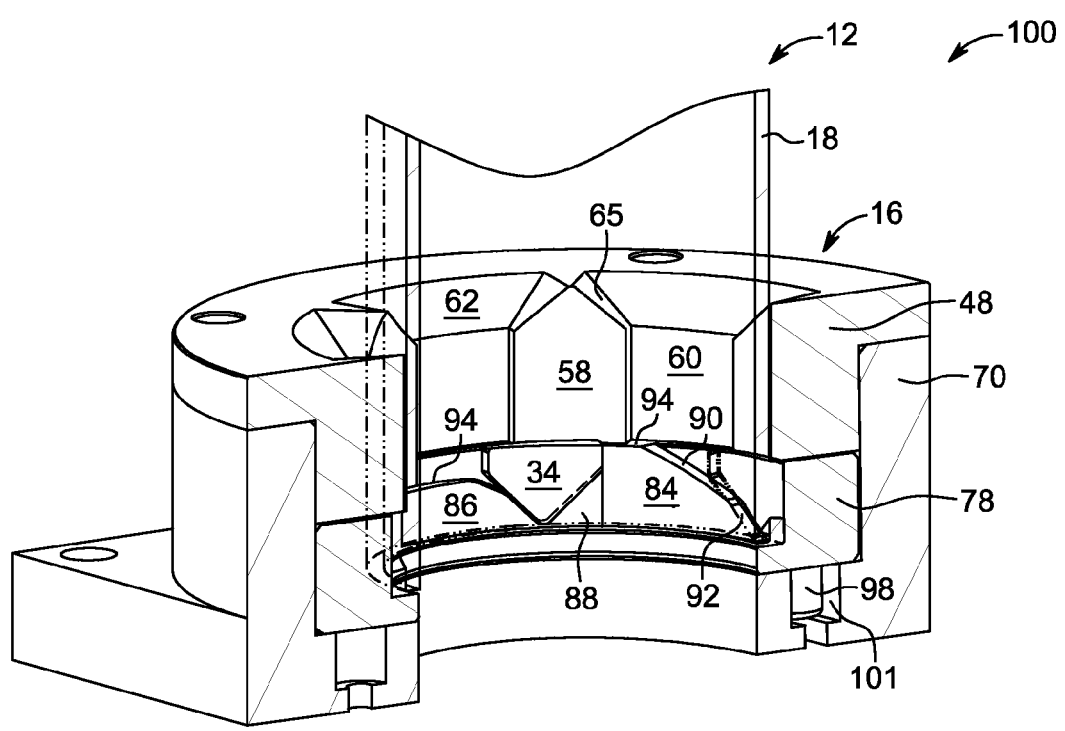
FIG. 2D is a cross-sectional perspective view of the connection interface shown in FIG. 2C.

With reference to FIG. 2D, the second retaining ring 78 is rotatably retained within the housing 70. At least one guide pin 98 extends in a proximal direction from a bottom surface of the second retaining ring 78. The at least one guide pin 98 is received inside at least one guide pin slot 101 formed on the bottom 82 of the housing 70. The at least one guide pin slot 101 may extend over a portion of a circumference of the bottom 82 (see FIG. 2A). At least one elastically resilient member 102 (shown in FIG. 2A), such as a spring, is connected to or in contact with at least a portion of the second retaining ring 78 and with at least a portion of the housing 70.

In one embodiment, the elastically resilient member 102 may be connected to or in contact with at one end of the at least one guide pin 98, while the opposing end of the elastically resilient member 102 may be connected to or in contact with an end of the at least one guide pin slot 101. The at least one elastically resilient member 102 (shown in FIG. 2A) urges the second retaining ring 78 to a first position (see FIG. 2B) wherein the one or more first recesses 60 are not aligned with the one or more second recesses 88. By inserting the syringe 12 into the syringe port 16, the one or more lugs 34 engage the one or more first and second locking elements 84, 86 to rotate the second retaining ring 78 to a second position and allow the insertion of the one or more lugs 34 into the one or more second recesses 88, as described herein.

To insert the syringe 12 into the syringe port 16, the insertion section 30 of the syringe 12 is urged into contact with the first retaining ring 48. If the lugs 34 are initially misaligned relative to the first recesses 60, guiding surfaces, for example the point 44 and/or at least one first surface 40 and/or at least one second surface 42 on the one or more lugs 34 and the guiding surfaces 62, 65 on the locking mechanism 35, guide the lugs 34 toward self-alignment with the first recesses 60 as the insertion section 30 is moved proximally relative to the retaining ring 48. Continued proximal movement of the syringe 12 relative to the first retaining ring 48 causes the lugs 34 to be guided into the first recesses 60 until at least a portion of one or more of the lugs 34 is brought into contact with the one or more first and second locking elements 84, 86 of the second retaining ring 78. The first and second inclined surfaces 90, 92 are configured for engaging at least one of the lug 34 surfaces 40, 42, or the point 44. Continued proximal movement of the syringe 12 relative the first retaining ring 48 causes the lugs 34 to exert a proximally directed force on the first and/or second inclined surfaces 90, 92 and thus on second retaining ring 78. As the second retaining ring 78 is prevented from moving proximally by the housing 70 and because of the slope or taper on the first and second inclined surfaces 90, 92 and/or the point 44 and/or at least one first surface 40 and/or at least one second surface 42 on the lug 34, the proximal movement creates a force which has a component in the rotational direction which acts against the restoring force of the at least one elastically resilient member 102 to rotate the second retaining ring 78 from the first position shown in FIG. 2B to a second position where the one or more first recesses 60 are aligned with the one or more second recesses 88. In this embodiment, the point 44 and/or at least one first surface 40 and/or at least one second surface 42 on the lug 34 are the opening surfaces which force open the locking or attachment mechanism 35. The one or more lugs 34 may cause the second retaining ring 78 to rotate in the first direction, such as a clockwise or a counterclockwise direction. As the second retaining ring 78 is rotated during a proximal movement of the syringe 12 within the syringe port 16, the one or more lugs 34 are guided into the corresponding one or more second recesses 88 until the point 44 of the lugs 34 engages a bottom or stop surface of the one or more second recesses 88. As the operator releases the syringe 12, under the restoring action of the elastically resilient member 102, the second retaining ring 78 is rotated in the second direction, which is opposite to the first direction, from the second position back to the first position. According to certain embodiments, rotation of the second retaining ring 78 relative to the housing 70 causes the syringe 12 to rotate therewith until the one or more lugs 34 are secured behind one or more retention surfaces 64 of the first retaining ring 48 and engage the one or more locking tabs 96. In this example embodiment, the first surface 40 is the rotational stop surface which interacts with locking tab 96. In some embodiments, movement of the second retaining ring 78 may be limited by the position of the one or more guide pins 98 within the one or more guide pin slots 101. Alternatively, one or more first and second locking elements 84, 86 of the second retaining ring 78 could interact with one or more elements on first retaining ring 48, for example an extension of one or more locking tabs 96 to limit the rotation of the second retaining ring 78. As the second retaining ring 78, along with the syringe 12, is rotated to the first position, the one or more second recesses 88 are offset relative to the one or more first recesses 60 such that removal of the syringe 12 in the distal direction is prevented by one or more retention surfaces 64 of the first retaining ring 48 interacting with one or more base surfaces 38 of one or more lugs 34.

In another embodiment, the elastically resilient member 102 continues to exert a torque to close or hold the lug 34 against locking tab 96. In some embodiments, second inclined surface 92 continues to be urged against the second surface 42 of the lug 34. In such embodiments, because the syringe 12 can rotate no further, the force between the two surfaces urges the syringe 12 distally, pushing the one or more base surfaces 38 against the one or more retention surfaces 64. This has the benefit of taking up the mechanical slack, slop, or clearances that are needed to allow free motion of the syringe 12 during installation and removal. The strength of the torque, the slopes/tapers of the surfaces, and the friction involved can be adjusted to lock the syringe 12 tightly enough that minimal reverse or proximal motion will happen during the filling of a syringe 12. An audible and/or tactile feedback may be provided when the syringe 12 is seated and locked within the syringe port 16. The audible and/or tactile feedback may be generated by an interaction of any surface on the syringe 12 with a corresponding surface on the syringe port 16 when the syringe 12 is in the locked position. For example, audible and/or tactile feedback may be generated by an interaction of at least one surface on the lug 34, such as the point 44 and/or at least one first surface 40 and/or at least one second surface 42, with at least a portion of the locking mechanism 35. The rotation of the syringe 12 due to the force of the elastically resilient member 102 during engagement may produce a tactile feedback.

To unlock and remove the syringe 12 from the syringe port 16, the syringe 12 is rotated relative to the first retaining ring 48 about the central axis 59 against the restoring force of the elastically resilient member 102. For example, if the syringe 12 is locked within the syringe port 16 by rotating the syringe 12 in a clockwise direction, the syringe 12 may be unlocked by rotating the syringe 12 in a counterclockwise direction. Rotation of the syringe 12 aligns the second recesses 88 with the first recesses 60. The syringe 12 can then be removed/ejected from the syringe port 16 by movement of the syringe 12 in a distal direction. In the process of turning the syringe 12 and thus rotating the second retaining ring 78 against the force of the elastically resilient member 102, the at least one second surface 42 or the point 44 on the syringe 12 and the first and/or second inclined surface 90, 92 on the second retaining ring 78 interact to create a distally directed force on the syringe 12 to eject/urge the syringe 12 out of syringe port 16. When a syringe 12 is released, unlatched, or disengaged, the syringe 12 is free to be removed or pulled from the syringe port 16 by the user. In some embodiments of the present disclosure, when the syringe 12 is released from the syringe port 16, there is an axial force ejecting, pushing, urging or moving the syringe 12 distally out of the syringe port 16 without any guidance or effort by the technician. In certain embodiments, this force or motion may not necessarily be sufficient to fully eject the syringe 12 all the way out of the syringe port 16, however, the force or motion may be sufficient so that the user has a tactile indication or feedback that the rotation is sufficient for release and the syringe 12 may be more readily removed from the syringe port 16. For example, rotation of the syringe barrel 18 may cause the point 44 on the lug 34 to slide along the surface in a distal direction along the surface of the first and/or second inclined surface 90, 92 on the second retaining ring 78. When the base surface 38 of the one or more lugs 34 clears the corresponding one or more retention surfaces 64 on the second retaining ring 78, the distally directed force causes the syringe 12 to be urged distally and, if allowed, be ejected to a first position out of the syringe port 16, indicating to the operator that the syringe 12 has been fully released and can be removed from the syringe port 16. As the syringe 12 is removed from the syringe port 16, the restoring force of the elastically resilient member 102 causes the second retaining ring 78 to return to the first position for a subsequent insertion of the new syringe 12. In the embodiment shown in FIGS. 2A-2D, the syringe 12 may be rotated 30 degrees or less about the longitudinal axis 15 to disengage the syringe 12 for removal from the syringe port 16.

The operation of the locking mechanism 35 can be further explained through the interaction of the retention surfaces of the syringe 12 and syringe port 16 that cooperate to retain the syringe 12 in the syringe port 16 once one or more of the base surfaces 38 of the syringe 12 is engaged with the one or more retention surfaces 64 of the first retaining ring 48. The guiding surfaces of the syringe 12 and syringe port 16 that cooperate to self-align or automatically rotationally align the syringe 12 and the syringe port 16 for self-oriented installation of the syringe 12 include the one or more second surfaces 42 and/or point 44 of the syringe 12 and the one or more guiding surfaces 65 of the syringe port 16. The opening surfaces of the syringe 12 and syringe port 16 that cooperate to open the syringe port 16 for the installation of the syringe 12 include the one or more second surfaces 42 of the syringe 12 and one or more of the first and/or second inclined surfaces 90, 92 of the syringe port 16. The tightening surfaces of the syringe 12 and syringe port 16 that cooperate to take up the mechanical slack or tolerances include one or more surfaces 38, 40, 42 of the syringe 12 and/or surfaces 64, 96, 90, 92 of syringe port 16. The detachment surfaces of the syringe 12 and syringe port 16 that cooperate to disengage or remove the syringe 12 from the syringe port 16 include surfaces 42 of the syringe 16 and surfaces 90, 92 of the syringe port 16. The ejection surfaces of the syringe 12 and syringe port 16 that cooperate to create a distally directed force to urge ejection of the syringe 12 from syringe port 16 include the second surfaces 42 of the syringe 12 and second inclined surfaces 92 of the syringe port 16. The rotational stop surfaces of the syringe 12 and syringe port 16 that cooperate to prevent rotation as a luer connector is screwed onto the syringe 12 include the one or more first surfaces 40 of the syringe 12 and the one or more locking tabs 96 of the syringe port 16, as well as any frictional force between the one or more base surfaces 38 of the syringe 12 and the one or more retention surfaces 64 of the syringe port 16. The syringe clearance surface(s), which allow the syringe to fit into the syringe port 16, include outer surface 21 of the barrel 18 on one radially adjacent side (left or right) of the lug 34 which clear the sidewall 58 of the first retaining ring 48.

Figure 3A:
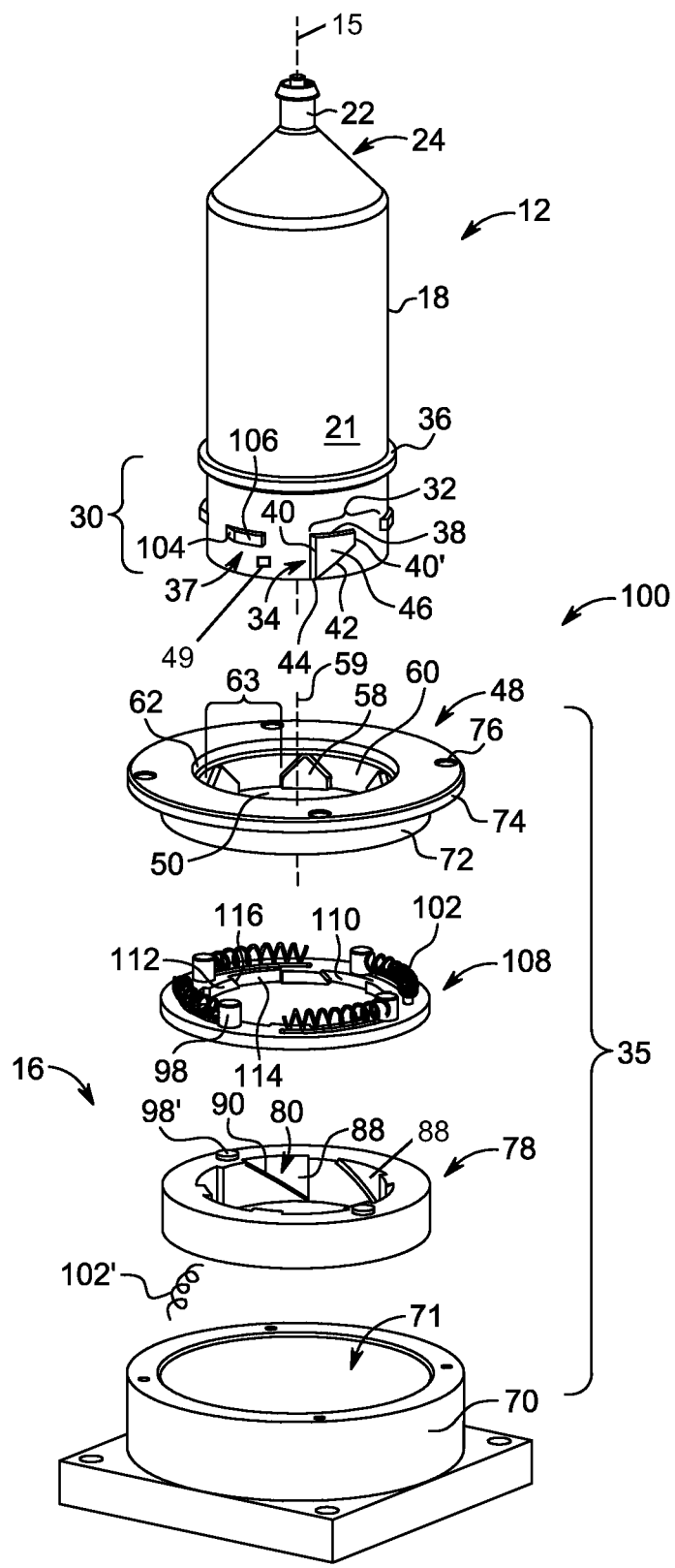
FIG. 3A is a front, exploded perspective view of a connection interface for securing a syringe to a fluid injector according to another embodiment.
Figure 3B:
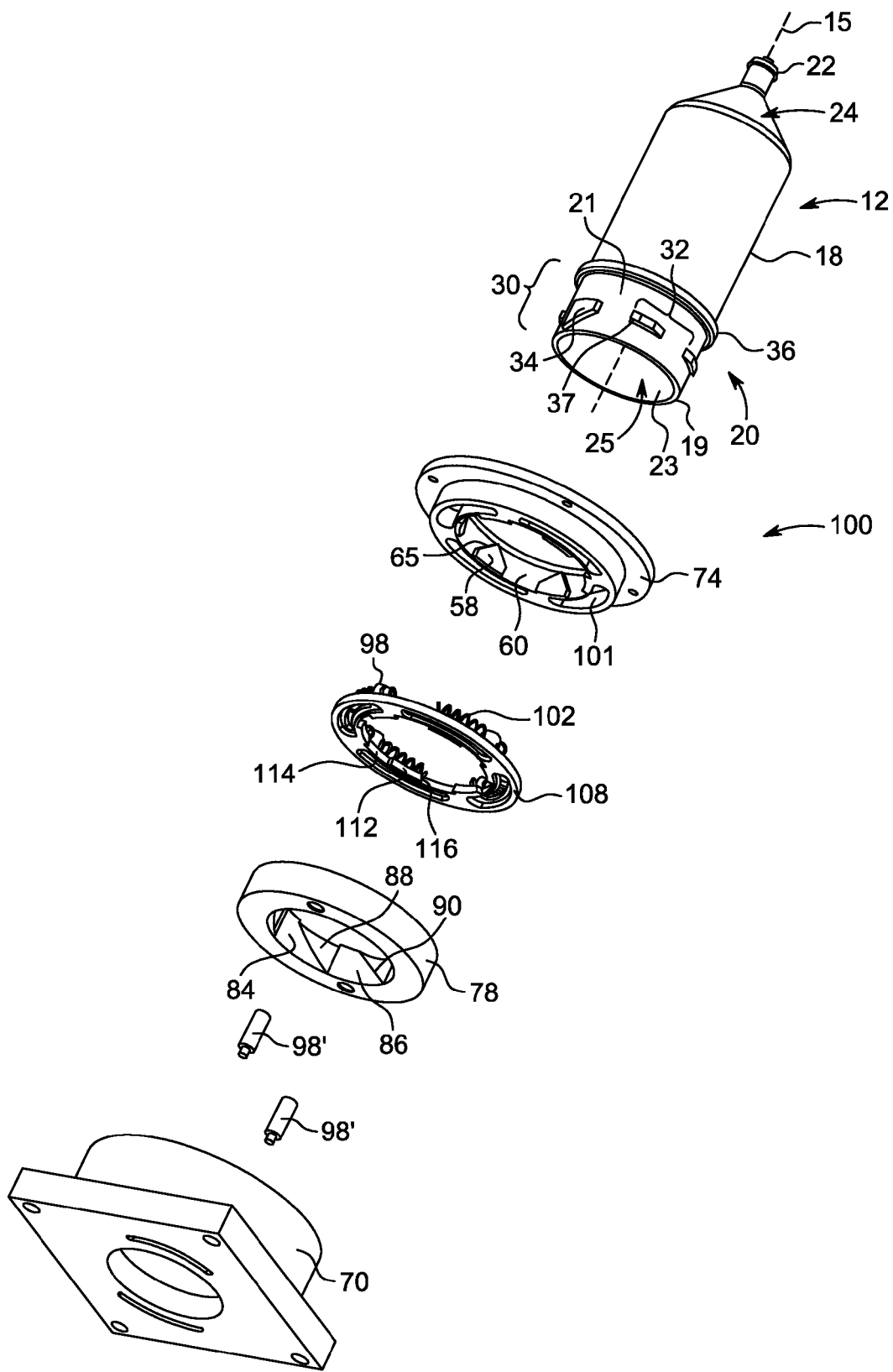
FIG. 3B is a rear, exploded perspective view of the connection interface shown in FIG. 3A.
Figure 3C:
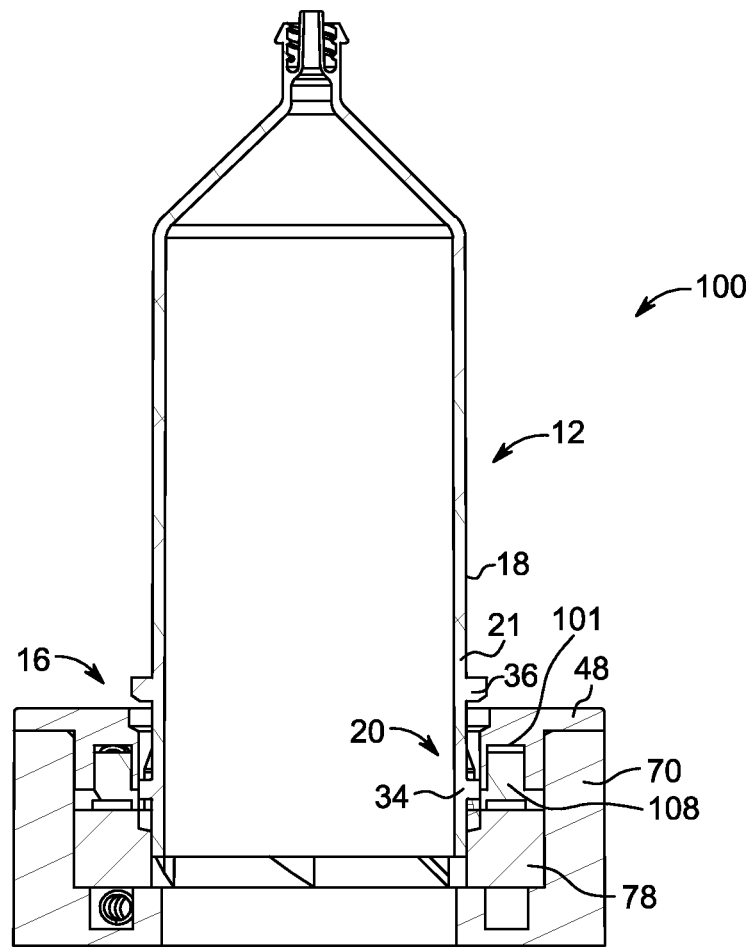
FIG. 3C is a cross-sectional view of the connection interface shown in FIG. 3A with a syringe loaded into a syringe port.

With reference to FIGS. 3A-3B, a connection interface 100 for loading and removing the at least one syringe 12 from the at least one syringe port 16 of the injector 10 is shown in accordance with another embodiment. The syringe 12 and the injector 10 include the connection interface 100 having at least one syringe retaining member 32 provided on the syringe 12 and a corresponding locking mechanism 35 provided on the syringe port 16 of the injector 10.

With reference to FIGS. 3A-3B, the syringe 12 generally has a cylindrical syringe barrel 18 formed from glass or a suitable medical-grade plastic. The barrel 18 has a proximal end 20 and a distal end 24, with a substantially cylindrical sidewall 19 (shown in FIG. 3B) extending therebetween along a length of a longitudinal axis 15 extending through a center of the barrel 18. A nozzle 22 extends from the distal end 24 of the barrel 18. The barrel 18 has an outer surface 21 and an inner surface 23 (shown in FIG. 3B) that defines an interior volume 25 (shown in FIG. 3B) configured for receiving a medical fluid therein.

A drip flange 36 may optionally extend radially outward from the outer surface 21 of the syringe barrel 18 relative to the longitudinal axis 15. The drip flange 36 may extend around at least a portion of the outer circumference of the barrel 18. In one embodiment, the drip flange 36 is positioned distally along the longitudinal axis 15 relative to the syringe retaining member 32. The drip flange 36 may be configured to prevent fluid that drips from the nozzle 22 from entering the syringe port 16 on the injector 10. In this manner, the drip flange 36 helps reduce the amount of fluid that may enter the syringe port 16 and jam or interfere with the connection interface 100 and/or the interior mechanics and electronics of the injector 10 (shown in FIG. 1A). In some embodiments, the drip flange 36 defines a stop surface that delimits the insertion section 30 of the syringe 12. The drip flange 36 may be formed integrally with the barrel 18 or it may be affixed or otherwise secured to the outer surface 21 of the barrel 18 using, for example, a frictional fit and/or an adhesive. In other embodiments, the drip flange 36 may be formed on the outer surface 21 of the barrel 18 by etching, laser cutting, machining, or molding.

With continued reference to FIGS. 3A-3B, the proximal end 20 of the syringe 12 is sized and adapted to be inserted in the syringe port 16 of the injector 10 (shown in FIG. 1A). In some embodiments, the proximal end 20 of the syringe 12 defines an insertion section 30 that is configured to be removably inserted into the syringe port 16 of the injector 10 while the remaining portion of the syringe 12 remains outside of the syringe port 16. One or more syringe retaining members 32 are provided on or near the proximal end 20 of the syringe barrel 18 as described herein, for forming a locking engagement with a corresponding locking mechanism 35 in the syringe port 16 according to the embodiment shown in FIGS. 3A-3B. For example, the one or more syringe retaining member 32 may be provided on an outer surface 21 of the syringe barrel 18. The syringe retaining member 32 may be formed integrally with the barrel 18 or it may be affixed or otherwise secured to the outer surface 21 of the barrel 18 using, for example, a frictional fit, welding, and/or an adhesive. In other embodiments, the syringe retaining member 32 may be formed on the outer surface 21 of the barrel 18 by etching, laser cutting, machining, or molding. The combination of the syringe 12 having the one or more syringe retaining members 32 and the locking mechanism 35 of the injector 10 (shown in FIG. 1A) defines a connection interface for loading and unloading of the syringe 12 to and from the injector 10. In some embodiments, the one or more syringe retaining members 32 cooperate with at least a portion of the locking mechanism 35 to self-orient the syringe 12 relative to the syringe port 16 such that the syringe 12 may be releasably locked with the syringe port 16.

In the embodiment shown in FIGS. 3A-3B, the at least one syringe retaining member 32 is formed as one or more first lugs 34 and optionally one or more second lugs 37 that protrude radially outwardly from the outer surface 21 of the syringe barrel 18 relative to the longitudinal axis 15. The one or more first lugs 34 and/or one or more second lugs 37 protrude radially outwardly from the outer surface 21 of the barrel 18 in a direction substantially perpendicular to the outer surface 21. In embodiments where more than two first and/or second lugs 34, 37 are provided, the first and second lugs 34, 37 may be evenly or unevenly spaced apart in a radial direction about an outer circumference of the barrel 18. In such embodiments, the first and second lugs 34, 37 are separated from each other by portions of the outer surface 21 of the barrel 18. Together, each first or second lug 34, 37 and the outer surface 21 of the barrel 18 on one radially adjacent side (left or right) of the first or second lug 34, 37 define the syringe retaining member 32. In some embodiments, a plurality of first and/or second lugs 34, 37 may be clustered and separated radially about the circumference of the barrel 18 from one or more adjacent clusters of first or second lugs 34, 37. For example, in an embodiment with six syringe retaining members 32 having equal angular separation therebetween, each syringe retaining member 32 extends over 60 degrees and is therefore separated by 60 degrees from the syringe retaining member 32 adjacent on either side. In such an embodiment, each first or second lug 34, 37 may extend over 30 degrees of the circumference of the barrel 18, while the portion of the outer surface 21 of the barrel 18 that defines the remainder of the syringe retaining member 32 extends over the remaining 30 degrees of the circumference. In other embodiments, each first or second lug 34, 37 may extend over more than 30 degrees or less than 30 degrees of the circumference of the barrel 18. In some embodiments, the syringe retaining members 32 may have unequal angular extension and/or unequal angular spacing between the syringe retaining members 32 about the outer circumference of the barrel 18. The one or more first lugs 34 are offset longitudinally along the longitudinal axis 15 relative to the one or more second lugs 37. In one embodiment, the one or more first lugs 34 are positioned closer to the proximal end 20 than the one or more second lugs 37. In other embodiments, one or more first lugs 34 are aligned longitudinally with the one or more second lugs 37 along the longitudinal axis 15 such that at least a portion of the one or more first lugs 34 is at a same longitudinal distance from the proximal end 20 as at least a portion of the one or more second lugs 37. In an embodiment in which one or more lugs 34 or 37 are absent, the corresponding retaining member 32 may be defined as the clearance surface(s), which is the outer surface 21 of the barrel 18 between adjacent lugs 34, 37. While embodiments having each syringe retaining member 32 extending over 60 degrees are exemplified in the attached drawings, syringes with retaining members 32 having other angles of separation, for example 360/x degrees where x is value from 1 and 36, are also within the scope of the present disclosure.

With continuing reference to FIG. 3A, each of the one or more first lugs 34 may have a generally triangular, polygonal, or arrowhead shape or alternatively may be shaped according to FIGS. 5A-Z or 10A-H. Each of the one or more first lugs 34 has a base surface 38 that may be substantially perpendicular to the longitudinal axis 15 of the barrel 18. In some embodiments, the base surface 38 may be angled relative to the direction of the longitudinal axis 15 in a radial cross-sectional plane. In other embodiments, the base surface 38 may be angled relative to the direction of the longitudinal axis 15 as it extends around the outer circumference of the barrel 18 in a radial cross-sectional plane. The base surface 38 may be planar, segmented, arcuate, curved, or a combination thereof.

In some embodiments, the base surface 38 may have a plurality of individual sections that together define the base surface 38. The plurality of individual sections of the base surface 38 may define a surface that may be planar, segmented, arcuate, curved, or a combination thereof.

In certain embodiments, at least one first surface 40 may extend on one end of the base surface 38 in a direction substantially parallel to the longitudinal axis 15. In some embodiments, at least one first surface 40 may be tapered axially relative to the longitudinal axis 15 in a proximal or a distal direction of the longitudinal axis 15. The axial tapering of the at least one first surface 40 relative to the longitudinal axis 15 may be defined as an angle of inclination of the first surface 40 in a cylindrical plan projection view in a direction from the distal end 24 toward the proximal end 20. The at least one first surface 40 may be directly connected with the base surface 38. In some embodiments, at least one first surface 40 may be disconnected from the base surface 38. The at least one first surface 40 may be planar, segmented, arcuate, curved, or a combination thereof. In some embodiments, the at least one first surface 40 may have a plurality of individual sections that together define the at least one first surface 40. The plurality of individual sections of the at least one first surface 40 may define a surface that may be planar, segmented, arcuate, curved, or a combination thereof.

At least one second surface 40' may extend on one end of the base surface 38 opposite the first surface 40 in a direction substantially parallel to the longitudinal axis 15. In some embodiments, at least one second surface 40' may be tapered axially relative to the longitudinal axis 15 in a proximal or a distal direction of the longitudinal axis 15. The axial tapering of the at least one second surface 40' relative to the longitudinal axis 15 may be defined as an angle of inclination of the first surface 40 in a cylindrical plan projection view in a direction from the distal end 24 toward the proximal end 20. The at least one second surface 40' may be directly connected with the base surface 38. In some embodiments, at least one second surface 40' may be disconnected from the base surface 38. The at least one second surface 40' may be planar, segmented, arcuate, curved, or a combination thereof. In some embodiments, the at least one second surface 40' may have a plurality of individual sections that together define the at least one second surface 40'. The plurality of individual sections of the at least one second surface 40' may define a surface that may be planar, segmented, arcuate, curved, or a combination thereof.

In some embodiments, at least one third surface 42 extends from one end of the second surface 40' to the end of the first surface 40. The at least one third surface 42 may be tapered axially relative to the longitudinal axis 15 in a proximal or a distal direction of the longitudinal axis 15. In some embodiments, at least one third surface 42 may be tapered axially relative to the longitudinal axis 15 in a proximal direction. The axial tapering of the at least one third surface 42 relative to the longitudinal axis 15 may be defined as an angle of inclination of the at least one third surface 42 in a cylindrical plan projection view in a direction from the distal end 24 toward the proximal end 20. The at least one third surface 42 and the at least one first surface 40 may join together at a rounded or a sharp point 44. The at least one third surface 42 may be directly connected with at least one of the first surfaces 40 at the point 44. In some embodiments, at least one third surface 42 may be disconnected from at least one of the first surfaces 40 at the point 44. In some embodiments, the point 44 may be disconnected from the at least one third surface 42 and the first surface 40. The at least one third surface 42 may be planar, segmented, arcuate, curved, or a combination thereof. In some embodiments, the at least one third surface 42 may have a plurality of individual sections that together define the at least one third surface 42. The plurality of individual sections of the at least one third surface 42 may define a surface that may be planar, segmented, arcuate, curved, or a combination thereof.

The base surface 38 and the first, second, and third surfaces 40, 40', 42 define a top surface 46 of each of the one or more first lugs 34. In some embodiments, the top surface 46 may be shaped to correspond to the curvature of the syringe barrel 18. In other embodiments, the top surface 46 of one or more of the lugs 34 may be angled relative to the outer surface 21 of the syringe barrel 18 such that a first end of the top surface 46 is higher than a second end of the top surface 46 relative to the syringe barrel 18. The top surface 46 may be continuous and uninterrupted, or it may be comprised of a plurality of separate surfaces that together define the top surface 46. The top surface 46 may be planar, segmented, arcuate, curved, or a combination thereof.

Each of the one or more second lugs 37 may be formed as a projection that extends radially outward from the outer surface 21 of the barrel 18. The one or more second lugs 37 optionally have an inclined release member 104 that extends from the outer surface 21 of the barrel 18 to the top surface 106 of the at least one second lug 37 in a direction of the circumference of the barrel 18. If present, the inclined release member 104 may facilitate the molding of the syringe 12 in a simple two part mold. In some embodiments, the top surface 106 may be shaped to correspond to the curvature of the syringe barrel 18. In other embodiments, the top surface 106 may be angled relative to the outer surface 21 of the syringe barrel 18. The top surface 106 may be continuous and uninterrupted, or it may be comprised of a plurality of separate surfaces that together define the top surface 106. The top surface 106 may be planar, segmented, arcuate, curved, or a combination thereof. The release member 104 may be configured to engage a third retaining ring 108 to release the syringe 12 from the syringe port 16, as described herein.

With continuing reference to FIG. 3A, the at least one syringe port 16 of the injector 10 (shown in FIG. 1A) has a locking mechanism 35 configured to operatively engage the at least one syringe retaining member 32 of the syringe 12. The locking mechanism 35 includes a housing 70 having a substantially circular shape with a central opening 71 configured to receive the proximal end 20 of the syringe 12. The housing 70 may be formed as part of the housing 14 of the injector 10 (shown in FIG. 1A) or as a fitted attachment of the housing 14 of the injector 10. A first retaining ring 48 is secured to a distal end of the housing 70 such that the central opening 71 of the housing 70 is aligned with a central opening 50 of the first retaining ring 48. The first retaining ring 48 has a body 72 having a radially extending flange 74. At least a portion of the body 72 extends away from the flange 74 in a proximal direction. When installed on the housing 70, the flange 74 engages a top portion of the housing 70 and is secured by one or more fasteners (not shown) extending through one or more fastener openings 76. At least a portion of the body 72 of the first retaining ring 48 is inserted into the central opening 71 of the housing 70. In other embodiments, the first retaining ring 48 may be secured to the housing 70 by other mechanical fastening arrangement, such as a clip or snap fit. When installed on the housing 70, the central axis 59 of the first retaining ring 48 is coaxial with a central axis of the housing 70.

With continuing reference to FIG. 3A, an inner portion of a sidewall 58 within the central opening 50 of the first retaining ring 48 has one or more first recesses 60 that are configured to receive the one or more first lugs 34 of the syringe 12 when the insertion section 30 of the syringe 12 is inserted through the central opening 50 of the first retaining ring 48. The one or more first recesses 60 may be evenly spaced about the inner circumference of the sidewall 58. In such embodiments, the first recesses 60 are separated from each other by portions of the sidewall 58 of the first retaining ring 48. Together, each first recess 60 and the sidewall 58 of the first retaining ring 48 on one radially adjacent side (left or right) of the first recess 60 define a clearance space 63 for receiving the syringe retaining member 32 on the syringe 12. The first recess 60 of each clearance space 63 may be configured to receive at least one first lug 34 or the second lug 37 of the syringe retaining member 32, while the sidewall 58 of the first retaining ring 48 may be configured to receive a portion of the sidewall 19 of the barrel 18 when the syringe retaining member 32 is inserted into the clearance space 63. For example, in an embodiment where the first retaining ring 48 has six clearance spaces 63 equally separated about the circumference of the first retaining ring 48, each clearance space 63 is separated 60 degrees apart from the clearance spaces 63 adjacent on either side. In such embodiments, each first recesses 60 may extend over 30 degrees of the circumference of the first retaining ring 48 while the portion of the sidewall 58 of the first retaining ring 48 that defines the remainder of the clearance space 63 extends over the remaining 30 degrees of the circumference. In other embodiments, the first retaining ring 48 may include 1-5 or 7-12 or more clearance spaces 63 wherein each first recess 60 may extend over more than 30 degrees or less than 30 degrees of the circumference of the sidewall 58 of the first retaining ring 48. In some embodiments, the number of first and second lugs 34, 37 on the syringe 12 corresponds to the number of first recesses 60 on the retaining ring 48. In other embodiments, the number of first and second lugs 34, 37 on the syringe 12 is smaller than the number of first recesses 60 on the retaining ring 48. In such embodiments, the first and second lugs 34, 37 on the syringe 12 are spaced apart along an outer circumference of the syringe barrel 18 such that each first or second lug 34, 37 can be aligned with a corresponding first recess 60 on the retaining ring 48. In other embodiments, the number of first and second lugs 34, 37 on the syringe 12 is higher than the number of first recesses 60 on the retaining ring 48 such that more than one first and second lugs 34, 37 may be received within at least one first recess 60. For example, the first or second lug 34, 37 may be formed as a collection of lugs, either in one lug position or spread over two or more lug positions which operate together to perform one or more of the functions herein attributed to the first or second lugs 34, 37 or any surface thereof.

Each of the one or more first recesses 60 extends radially outward into the inner portion of the sidewall 58 relative to the central axis 59. The lateral surfaces of each first recess 60 define a travel path for guiding the movement of the first and second lugs 34, 37 in and out of the first recess 60 as the insertion section 30 of the syringe 12 is inserted into and out of the first retaining ring 48. Each first recess 60 extends substantially parallel along a direction of the central axis 59. In some embodiments, each first recess 60 may have one or more guiding surfaces 62 that guide the first and second lugs 34, 37 into self-alignment with the first recesses 60 such that the first and second lugs 34, 37 can be inserted into the first recesses 60 and self-align the syringe 12 within syringe port 16 without any guidance or effort by the technician. The guiding surfaces 62 may be inclined to toward an opening of the first recess 60 to guide the movement of the first and second lugs 34, 37. In this manner, the one or more first and second lugs 34, 37 which may be initially misaligned relative to the corresponding one or more recesses 60 are brought in self-alignment with the one or more recesses 60 by the one or more guiding surfaces 62.

With continued reference to the embodiment in FIG. 3A, the locking mechanism 35 further includes a second retaining ring 78 having a substantially annular shape with an inner sidewall 80. The second retaining ring 78 is disposed within the central opening 71 of the housing 70 between a proximal end of the body 72 of the first retaining ring 48 and a bottom 82 of the housing 70. As detailed further herein, the second retaining ring 78 is rotationally movable and axially fixed relative to the first retaining ring 48 and the housing 70. The second retaining ring 78 has one or more second recesses 88. The one or more second recesses 88 are configured to receive the one or more first and second lugs 34, 37 of the syringe 12 when the insertion section 30 of the syringe 12 is inserted through the central opening 50 of the first retaining ring 48. The one or more second recesses 88 are arranged around a circumference of the inner sidewall 80 of the second retaining ring 78 such that the one or more second recesses 88 are aligned with the one or more first recesses 60 on the first retaining ring 48. For example, in an embodiment where the first retaining ring 48 has six first recesses 60, the second retaining ring 78 may also have six second recesses 88 separated 60 degrees apart each other. The rotational movement of the second retaining ring 48 may be guided and constrained by one or more proximal pins 98' and/or one or more elastically resilient members 102' housed in one or more slots in housing 70.

With continued reference to FIG. 3A, the locking mechanism 35 may further include a third retaining ring 108 having a substantially annular shape with an inner sidewall 110. The third retaining ring 108 is disposed within the central opening 71 of the housing 70 between the first retaining ring 48 and the second retaining ring 78. As detailed further herein, the third retaining ring 108 is rotatable relative to the first retaining ring 48, the second retaining ring 78, and the housing 70, which are all fixed relative to each other. The third retaining ring 108 has one or more locking elements 112 disposed on at least a portion of the inner sidewall 110. The one or more locking elements 112 extend radially outward relative to the inner sidewall 110 and are arranged in an alternating manner such that each locking element 112 is separated by a third recess 114.

The one or more locking elements 112 have an inclined surface 116 configured for selectively engaging the third surface 42 of the one or more first lugs 34. The inclined surface 116 may be linear, segmented, curved, or a combination thereof.

With continued reference to FIG. 3A, the third retaining ring 108 is rotatably retained within the housing 70. At least one guide pin 98 extends from the third retaining ring 108 and is received inside at least one guide pin slot 101 (not shown) formed on one or both of the first and second retaining rings 48, 78. At least one elastically resilient member 102, such as a spring, is connected at one end to at least a portion of the third retaining ring 108 and to at least a portion of one or both of the first and second retaining rings 48, 78. In one embodiment, the elastically resilient member 102 may be connected at one end to the at least one guide pin 98, while the opposing end of the elastically resilient member 102 may be connected to the at least one guide pin slot 101. The at least one elastically resilient member 102 urges the third retaining ring 108 to a first position. By inserting the syringe 12 into the syringe port 16 in a proximal direction, the opening surface, in this embodiment the third surface 42 of one or more lugs 34, engages the one or more locking elements 112 to rotate the third retaining ring 108 to a second position where the at least one third recess 114 is aligned with at least one first recess 60 and at least one second 88. Once the second surface 40' on the first lug 34 clears the inclined surface 116 of the locking element 112, the third retaining ring 108 rotates in the opposite direction back to its initial first position and locks the syringe 12 within the syringe port 16 where base surface 38 is retained proximal to locking element 112, as described herein. An audible and/or tactile feedback may be provided when the syringe 12 is locked within the syringe port 16, for example by the movement of the third retaining ring 108 to the first position.

Figure 3D:
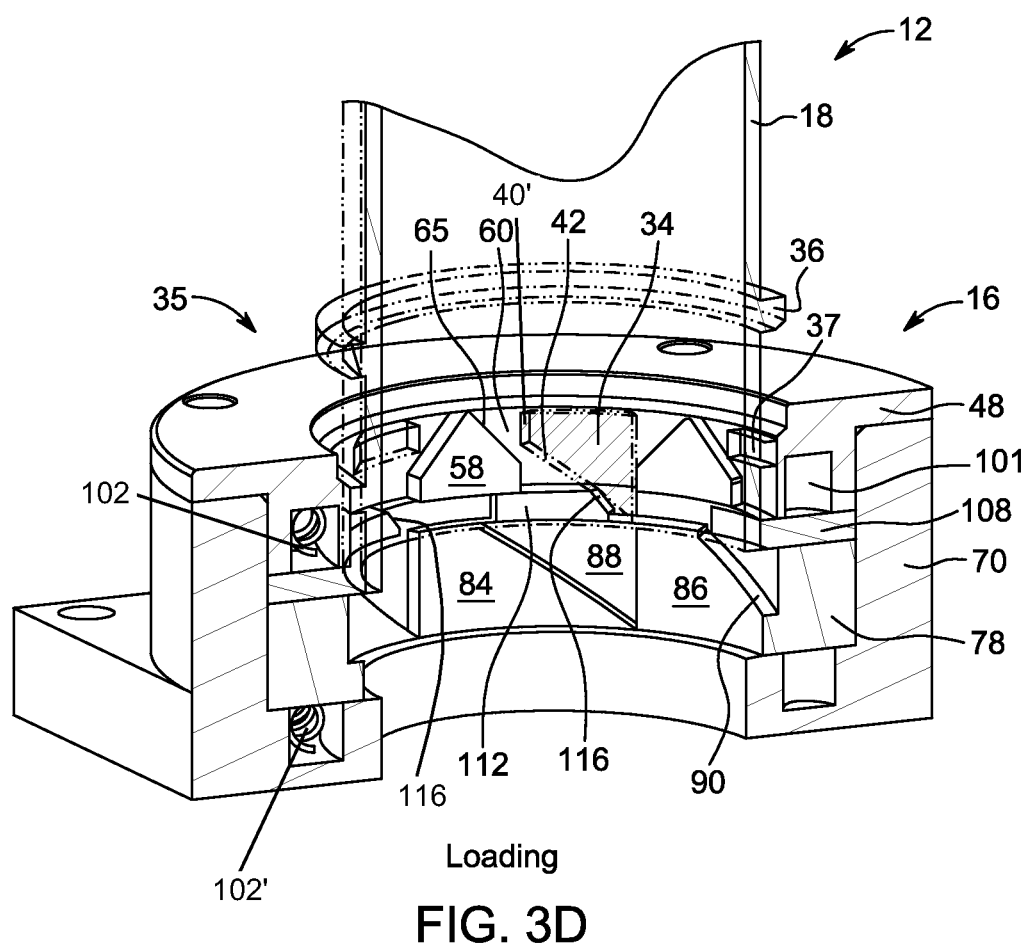
FIG. 3D is a cross-sectional view of the connection interface of FIG. 3C showing the syringe being loaded into the syringe port.
Figure 3E:
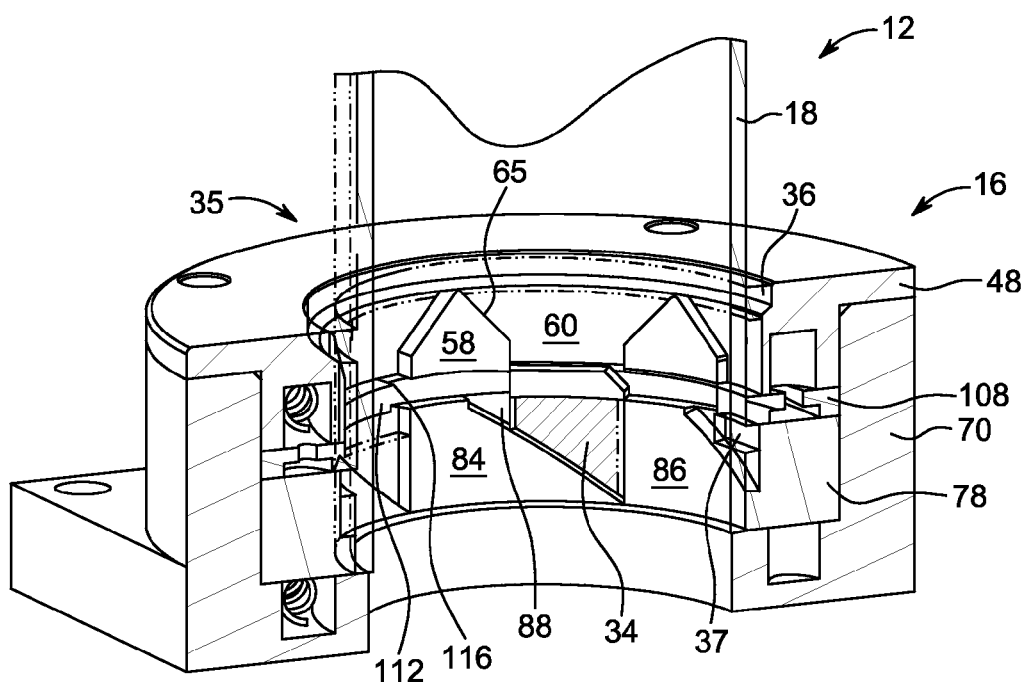
FIG. 3E is a cross-sectional view of the connection interface of FIG. 3C showing the syringe locked relative to the syringe port.

To insert the syringe 12 into the syringe port 16, the insertion section 30 of the syringe 12 is urged into contact with the first retaining ring 48, such as shown in FIG. 3D. If the first and second lugs 34, 37 are initially misaligned relative the first recesses 60, the guiding surfaces 65 guide the first and second lugs 34, 37 toward self-alignment with the first recesses 60 as the insertion section 30 is moved proximally relative to the first retaining ring 48. Continued proximal movement of the syringe 12 relative the first retaining ring 48 causes the first and second lugs 34, 37 to be guided within the first recesses 60 until at least a portion of the third surface 40' of one or more of the first lugs 34 is brought into contact with the inclined surface 116 of the one or more locking elements 112 of the third retaining ring 108. The inclined surface 116 is configured for engaging the second surface 40' of the first lugs 34. As shown in FIG. 3D, continued proximal movement of the syringe 12 relative the first retaining ring 48 causes the first lugs 34 to act against the restoring force of the at least one elastically resilient member 102 to rotate the third retaining ring 108 from the first position shown in FIG. 3D to a second position shown in FIG. 3E. The one or more first lugs 34 may cause the third retaining ring 108 to rotate in a first direction, such as a clockwise or a counterclockwise direction. As the third retaining ring 108 is rotated during a proximal movement of the syringe 12 within the syringe port 16, the one or more first lugs 34 and second lugs 37 are guided into the corresponding one or more second recesses 88 until the base surface 38 of all the first and second lugs 34, 37 clear the bottom portion of the third retaining ring 108. Under the restoring action of the elastically resilient member 102, the third retaining ring 108 is rotated in a second direction which is opposite to the first direction. Rotation of the third retaining ring 108 relative to the housing 70 causes the locking elements 112 to be positioned over the one or more first and second lugs 34, 37 such that removal of the syringe 12 in the distal direction is prevented.

Figure 3F:
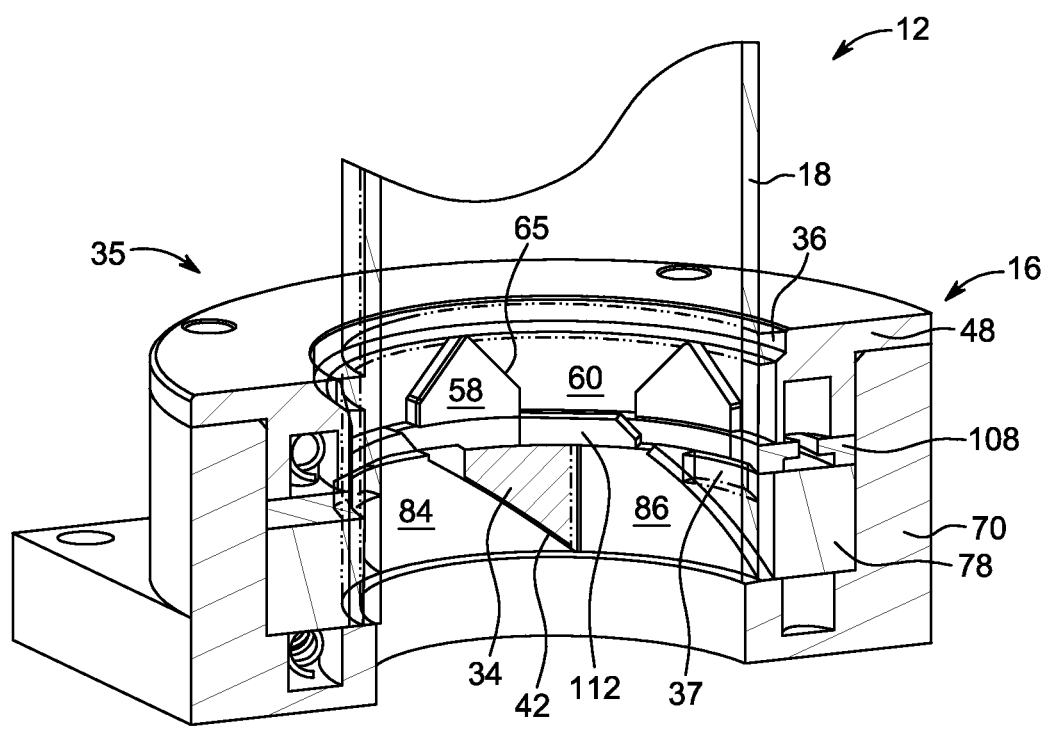
FIG. 3F is a cross-sectional view of the connection interface of FIG. 3C showing a first step in unlocking the syringe from the syringe port.
Figure 3G:
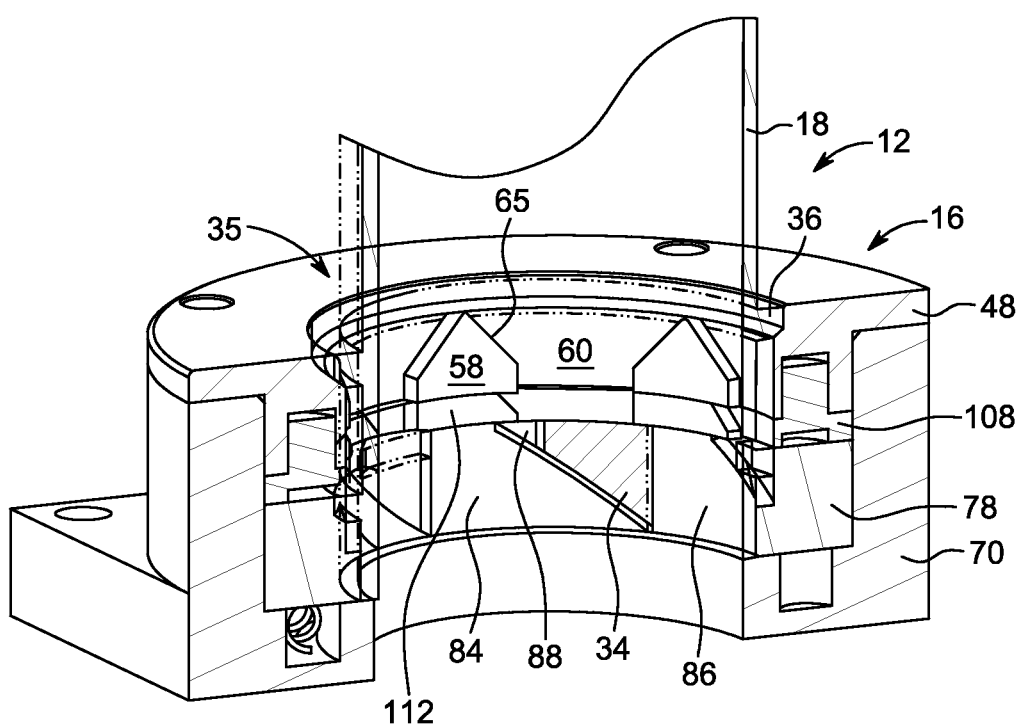
FIG. 3G is a cross-sectional view of the connection interface of FIG. 3C showing a second step in unlocking the syringe from the syringe port.
Figure 3H:
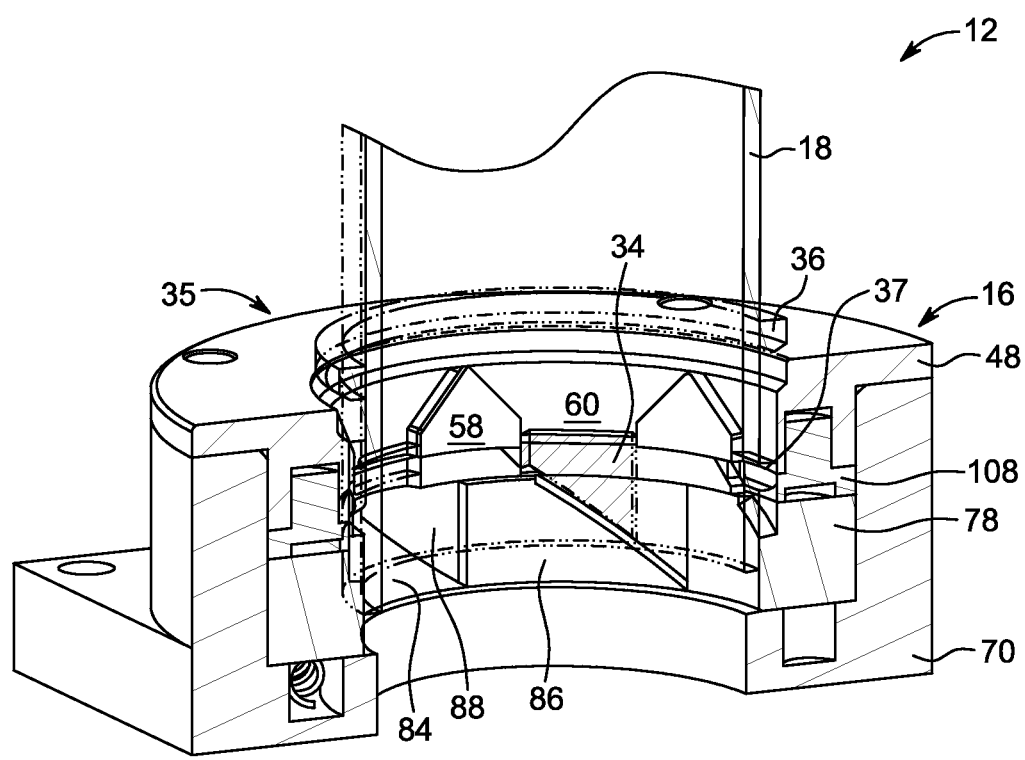
FIG. 3H is a cross-sectional view of the connection interface of FIG. 3C showing a third step in unlocking the syringe from the syringe port.

To unlock the syringe 12 from the syringe port 16, the syringe 12 is rotated in a first direction around the longitudinal axis 15, as shown in FIG. 3F. The rotational movement of the syringe 12 causes the third surface 42 of the first lugs 34 to bear against the first inclined surface 90 of the second retaining ring 78 and rotate the second retaining ring 78 against the force of its resilient member 102' (shown in FIG. 2A). After a rotation, for example of approximately 30 degrees, the guide pin 98 on the second retaining ring 78 engages the third retaining ring 108 to cause it to also rotate in the first direction. After additional rotation, for example approximately another 30 degrees of rotation, the first and second lugs 34, 37 line up with the first recesses 60 of the first retaining ring 48, and the locking elements 112 on the third retaining ring 108 move away to clear the space proximal to the first recesses 60 such that the at least one first recesses 60 are aligned with the at least one third 114, as shown in FIG. 3G. At this point, the distally directed force component created by the rotational movement of the third surface 42 of the first lugs 34 against the first inclined surface 90 causes the syringe 12 to move distally and eject from the syringe port 16, as shown in FIG. 3H. As the syringe 12 is ejected from the syringe port 16, the restoring force of the elastically resilient members 102 and 102' cause the third retaining ring 108 and the second retaining ring 78 to return to their respective first positions by rotating in a second direction in preparation for a subsequent insertion of a new syringe 12.

The operation of the locking mechanism 35 can be further discussed with reference to the retention surfaces of the syringe 12 and syringe port 16 that cooperate to retain the syringe 12 in the syringe port 16 once it is engaged are one or more base surfaces 38 and top surfaces 106 of the syringe 12 and the one or more surfaces of the locking elements 112 of the syringe port 16. The guiding surfaces of the syringe 12 and syringe port 16 that cooperate to self-align or automatically rotationally align the syringe 12 and the syringe port 16 for installation are the one or more points 44 and/or third surfaces 42 of the syringe 12 and the one or more guiding surfaces 65 of the syringe port 16. The opening surfaces of the syringe 12 and syringe port 16 that cooperate to open the syringe port 16 for the installation of the syringe 12 are the one or more third surfaces 42 of the syringe 12 and one or more of the inclined surfaces 116 of the syringe port 16. The detachment surfaces of the syringe 12 and syringe port 16 that cooperate to disengage or remove the syringe 12 from the syringe port 16 are the third surfaces 42 of the syringe 16 and inclined surface 90 of the syringe port 16. The ejection surfaces of the syringe 12 and syringe port 16 that cooperate to create a distally directed force to urge ejection of the syringe 12 from syringe port 16 are the third surfaces 42 of the syringe 16 and inclined surfaces 90 of the syringe port 16. The rotational stop surfaces of the syringe 12 and syringe port 16 that cooperate to prevent rotation as a luer connector is screwed onto the syringe 12 are the one or more first surfaces 40 and/or second surfaces 40' of the syringe 12 and the one or more second recesses 88 of the syringe port 16, as well as any frictional force between the one or more base surfaces 38 of the syringe 12 and the one or more locking elements 112 of syringe port 16. The syringe clearance surface(s), which allow the syringe to fit into the syringe port 16, are outer surface 21 of the barrel 18 on one radially adjacent side (left or right) of the lug 34 which clear the sidewall 58 of the first retaining ring 48.

The embodiment of the syringe port 16 of FIGS. 3A-3H has been described from the perspective that there are first recesses 60 cut into the sidewall 58 of the first retaining ring 48. In another embodiment, the sidewall 58 can be considered to project from the cylindrical surface defined by the first recesses 60 of the first retaining ring 48. Each of these two configurations may be used to describe or be embodied in a single embodiment.

While FIGS. 2A-3G illustrate several non-limiting embodiment of the at least one syringe retaining member 32, various other shapes are also contemplated. For example, the one or more first lugs 34 and/or second lugs 37 of the at least one syringe retaining member 32 may have a generally circular, square, rectangular, pentagonal, or any other polygonal shape. Various features may be provided on the at least one syringe retaining member 32 to help self-orient the syringe 12 relative to the syringe port 16 or to releasably lock the syringe 12 with the syringe port 16. In each embodiment, the at least one syringe retaining member 32 is configured for forming a reversible locking engagement with a corresponding locking mechanism in the syringe port 16 of the injector 10 for retaining the syringe 12 in the syringe port 16. Various other shapes for one or more lugs 34 of the at least one syringe retaining member 32 are discussed herein with reference to FIGS. 4A-5Z and 10A-10H.

Figure 4B:
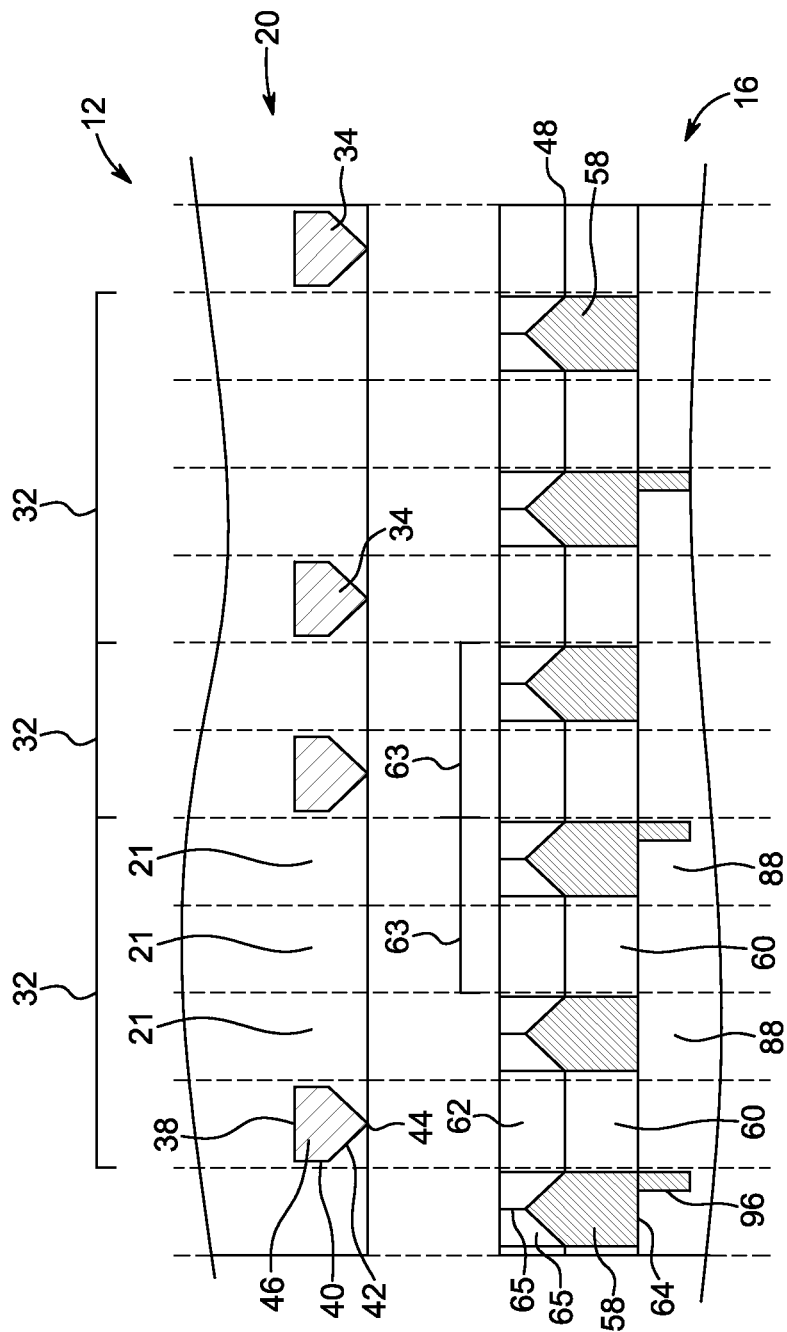
Figure 4C:
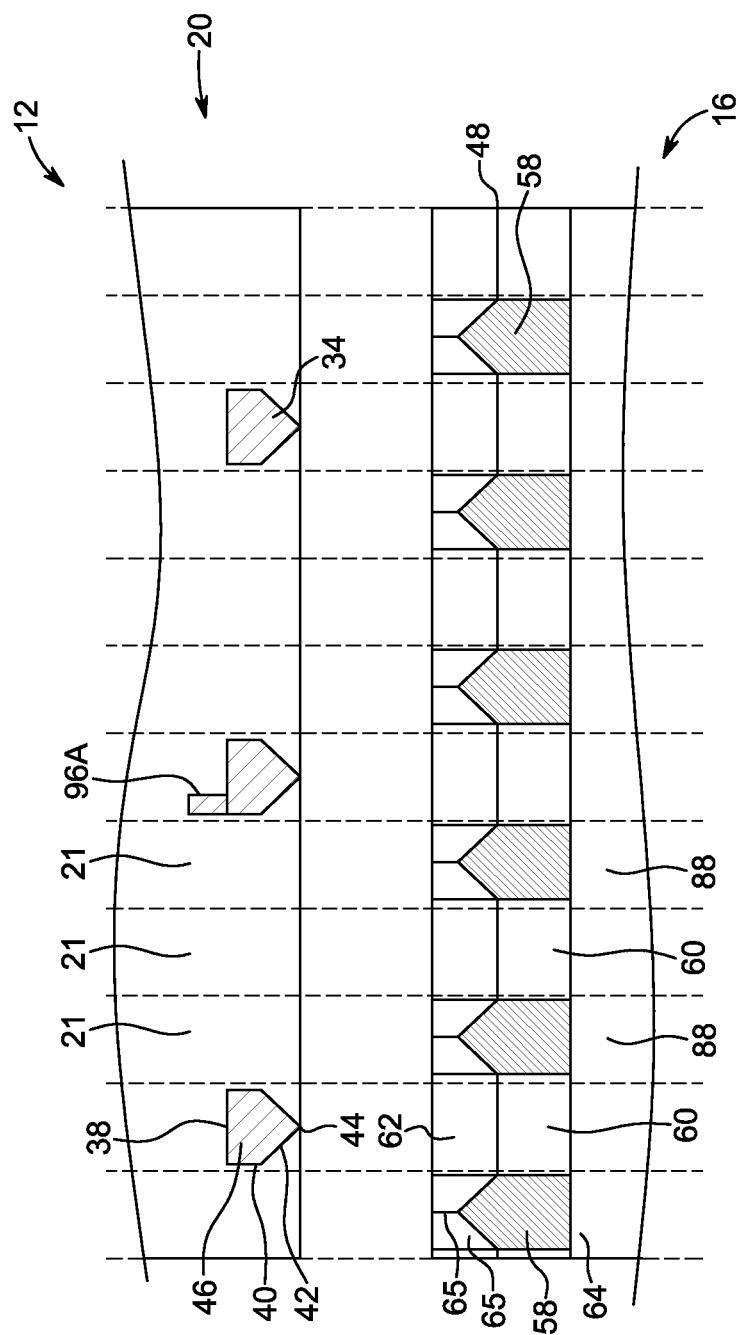
Figure 4D:
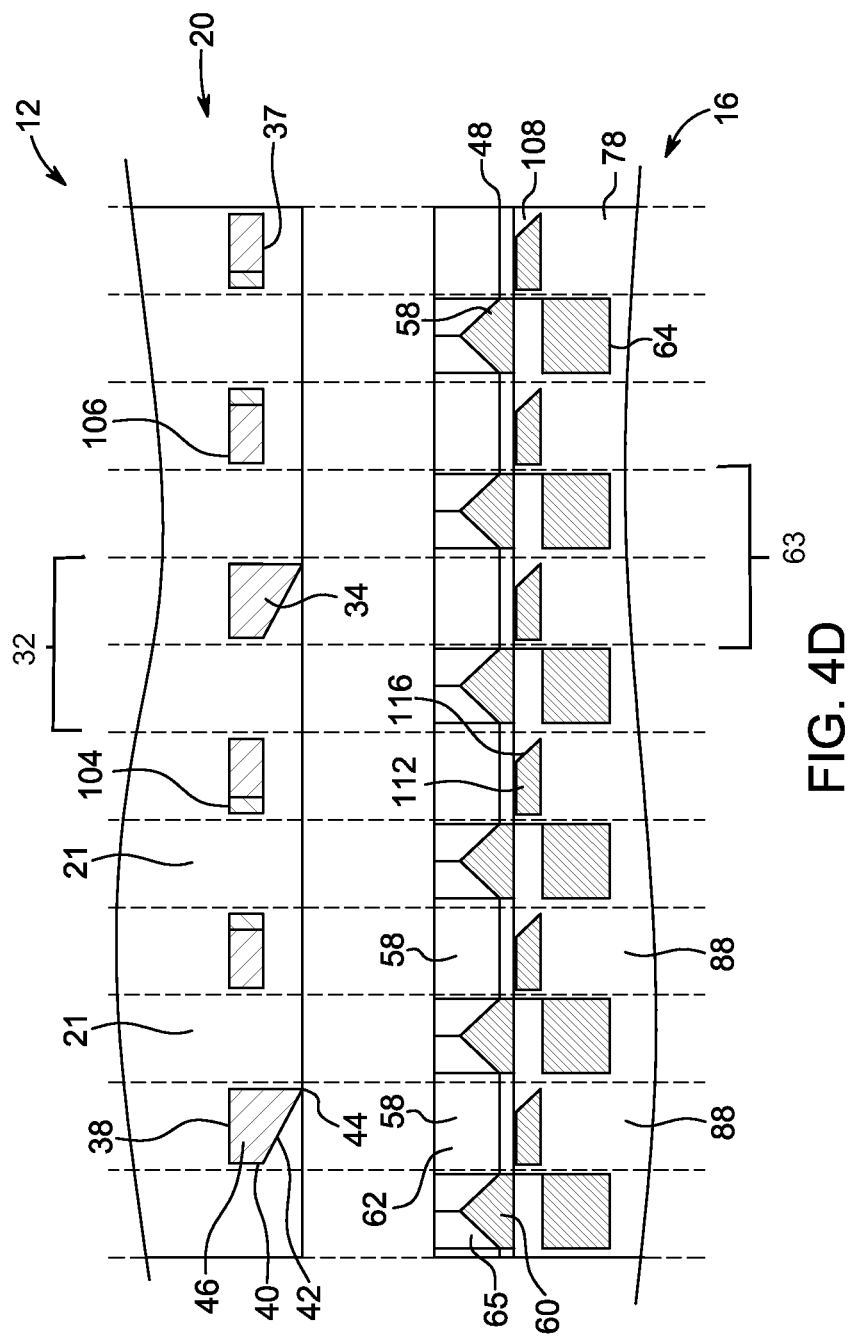
Figure 4E:
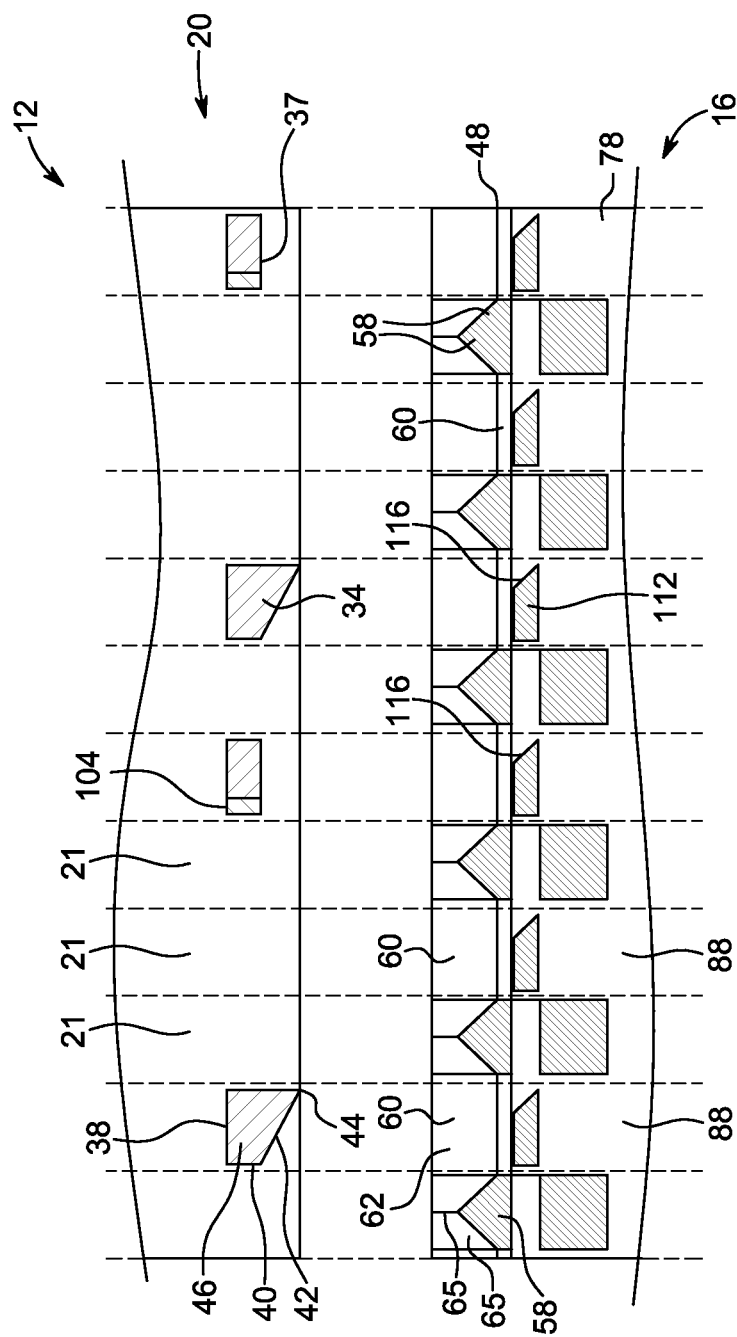
Figure 4F:
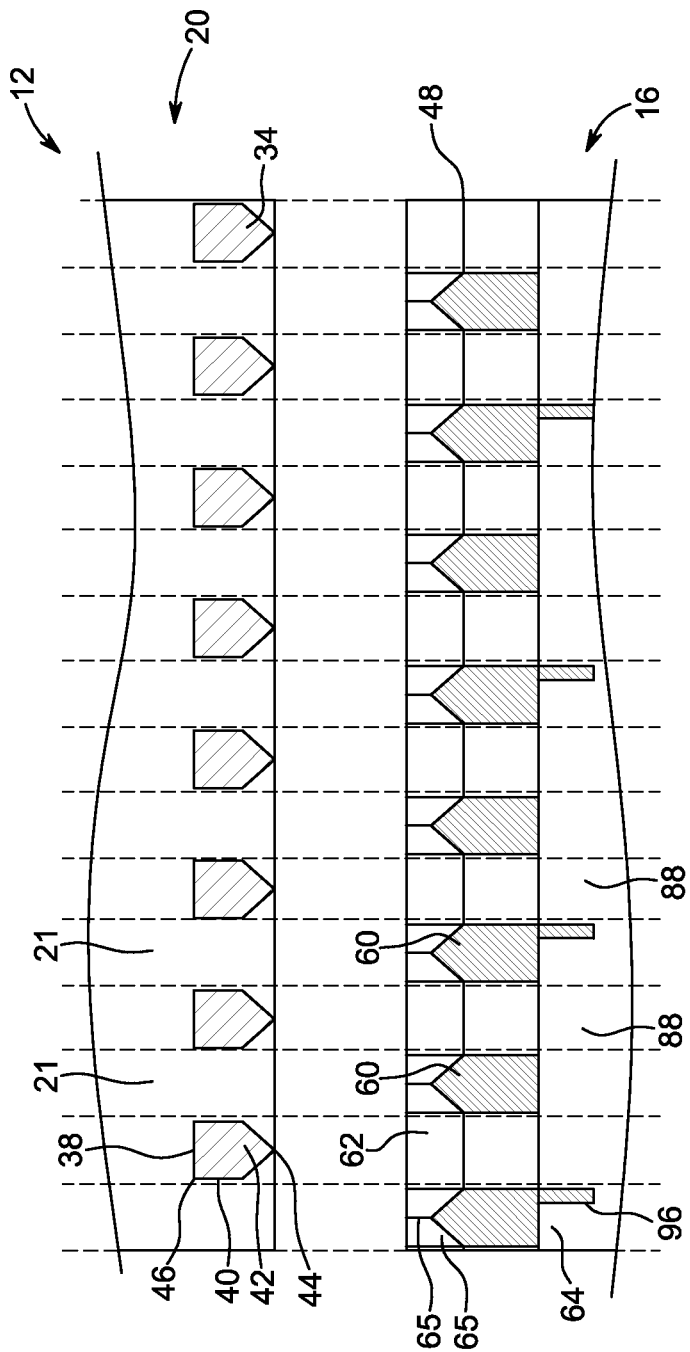
Figure 4G:
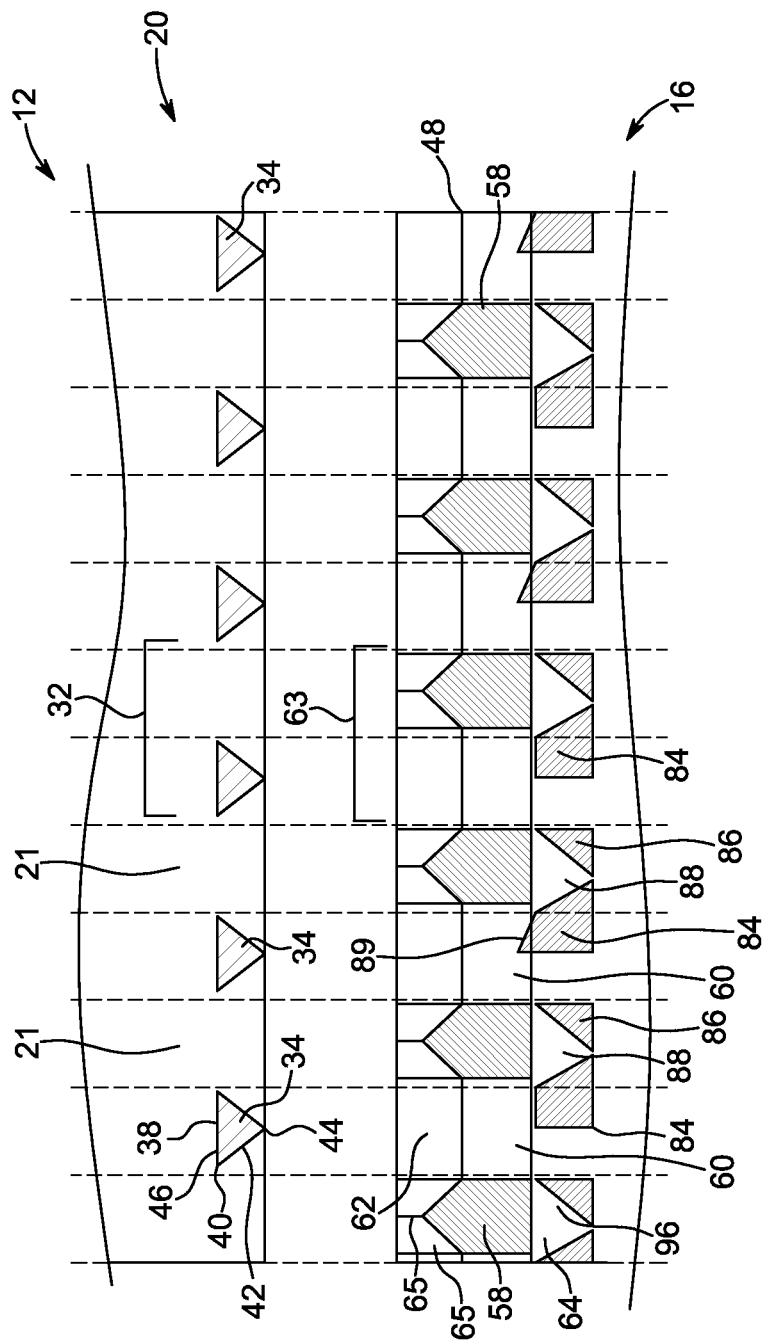
Figure 4H:
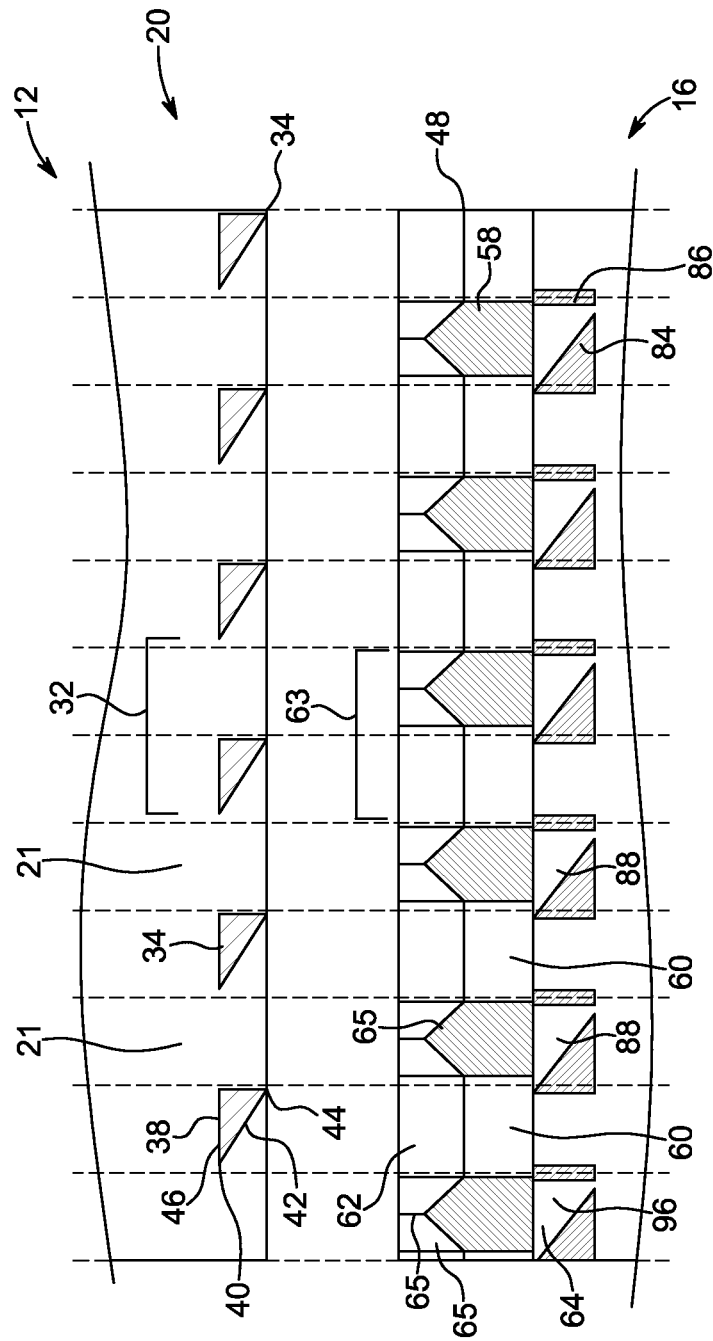
Figure 4I:
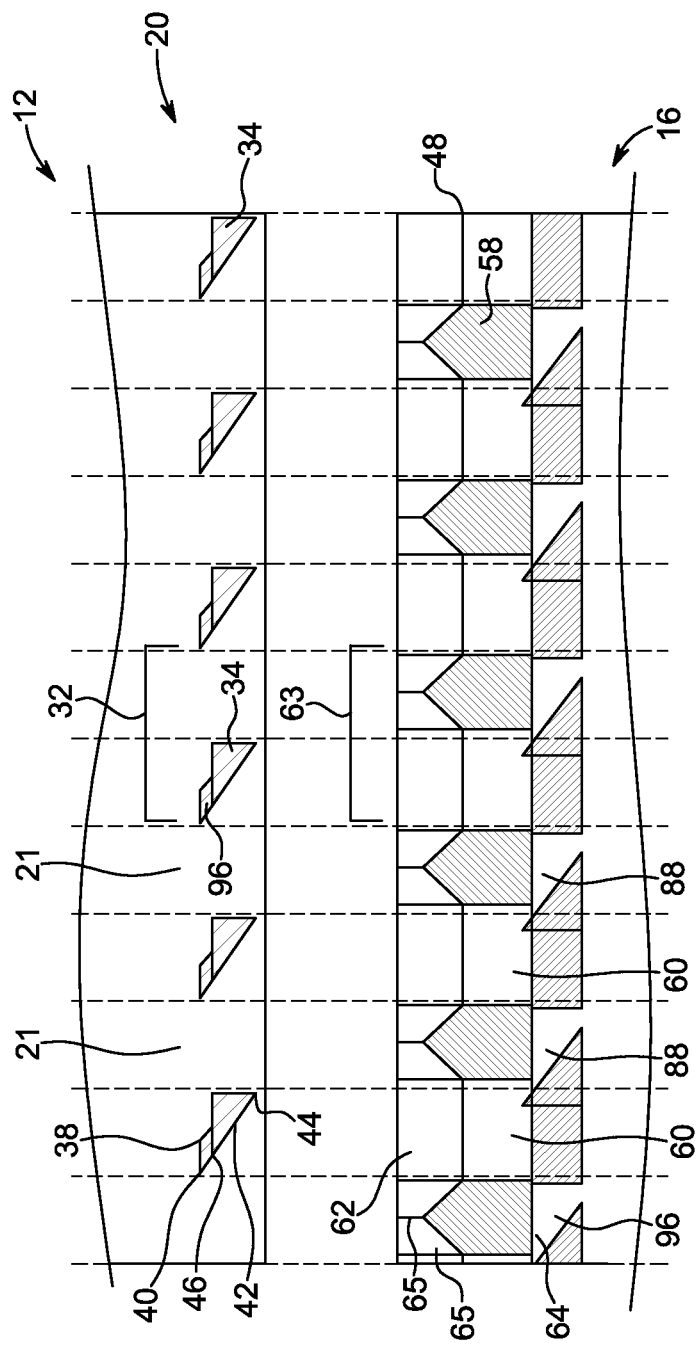
Figure 4J:
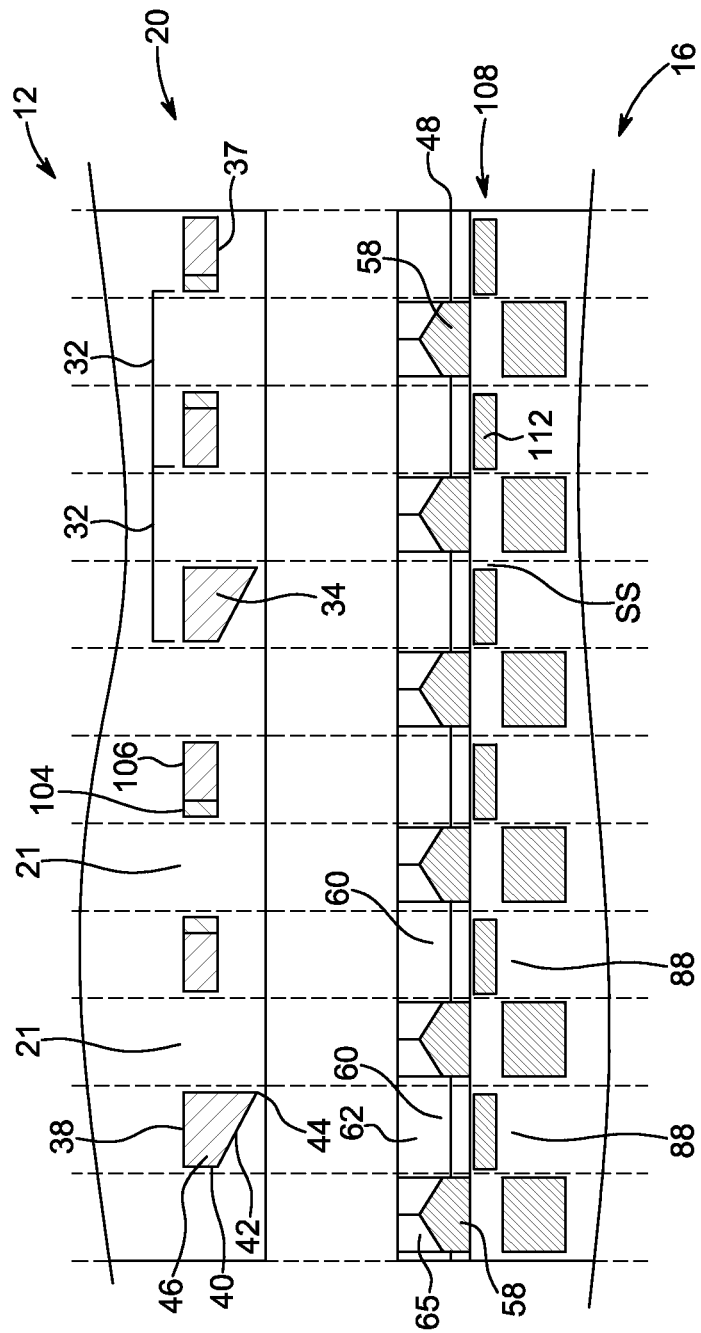
Figure 4K:
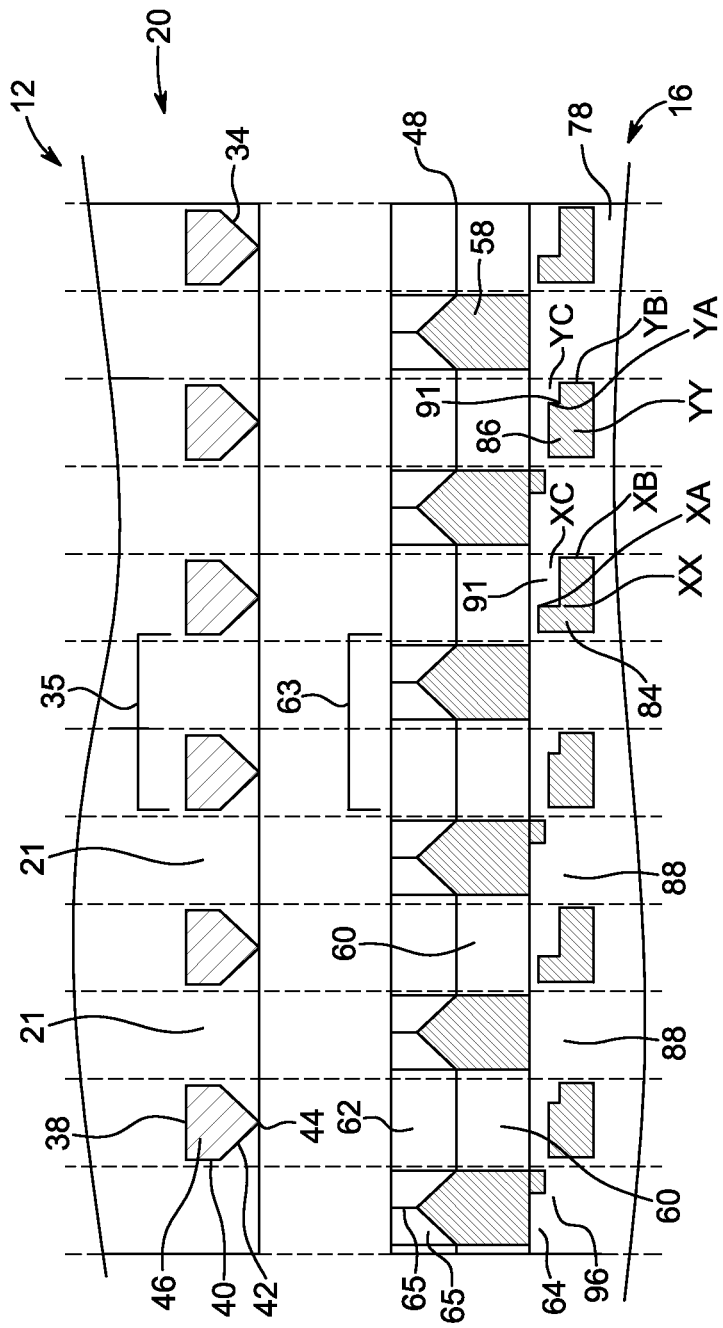
Figure 4L:
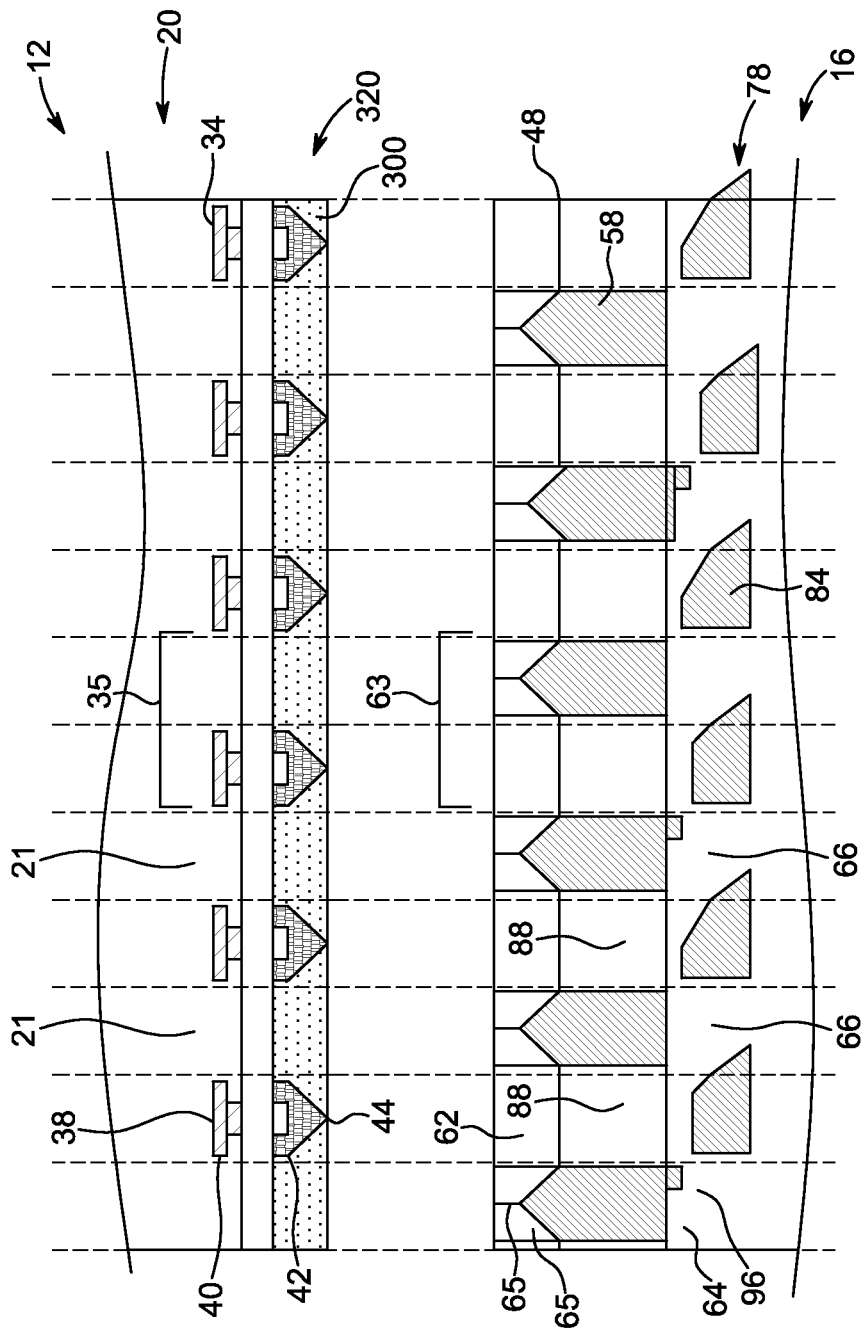

FIGS. 4A-4L show cylindrical plan projection views of various embodiments of the proximal end 20 of the at least one syringe 12 and a corresponding at least one syringe port 16 for receiving the proximal end 20 of the syringe 12. With reference to FIG. 4A, an embodiment of the proximal end 20 of the syringe 12, as generally illustrated in FIG. 2A, is rotationally aligned as shown by the dotted lines for insertion of the syringe 12 into the distal end of the syringe port 16. From this perspective, when self-aligned, the syringe retaining members 32, including the lugs 34 and the outer surface 21 of the barrel 18 located between the lugs 34 are configured to be received within the clearance space 63 of the syringe port 16 to allow insertion of the syringe 12 into the syringe port 16. Similarly, the outer surface 21 of the syringe barrel 18 clears the sidewall 58 of the first retaining ring 48. One way to measure or express the relationship between these elements is through the angle which they subtend on the outside of the syringe 12 and the inside of the syringe port 16. For example, in an embodiment with the six fold symmetry of the syringe retaining members 32, each lug 34 subtends a nominal angle of 30 degrees and each first recess 60 similarly subtends 30 degrees, of course with an allowance for clearance and tolerance so that the lug 34 can slide within the first recess 60. Because the one or more locking tabs 96 extend over a finite angular extent, the base surface 38 of the lug 34 may not be positionable fully under the retention surface 64. For example, if the lugs 34 and the first recesses 60 are both 30 degrees and locking tab 96 occupies an angle of 4 degrees, then the base surface 38 of the lug 34 will overlap with the locking tab 96 over a surface of 26 degrees. To maximize the overlap, the lug 34 can be reduced to 28 degrees and the recess 60 can be increased in width to 32 degrees, including the 4 degrees of the locking tab 96. Upon insertion, the entire width of the lug 34 may be positioned under the retention surface 64 adjacent the locking tab 96. Each lug 34 is configured for being received within the first recess 60 on the first retaining ring 48. The second surface 42 of each lug 34 may be self-guided into alignment with the first recess 60 along the guiding surface 65 to enable the insertion of the lug 34 into the first recess 60. With reference to FIG. 4K, the second retaining ring 78 has first locking elements 84 and second locking elements 86 having a substantially rectangular shape with a recess 91 provided in one of the upper corners. The recess 91 is configured for guiding the second surface 42 of the lugs 34 into the second recess 88 as the lugs 34 are inserted into the syringe port 16.

FIG. 4B shows another embodiment in which the number of lugs 34 is smaller than the number of recesses 60 on the syringe port 16. If one or more lugs 34 are absent, the missing area is taken up by a larger area of the outer surface 21 of the syringe 12. In some embodiments, at least two lugs 34 are provided, adjacent to each other, spaced around the barrel 18, or on opposite sides of the barrel 18, so that one of the lugs 34 will rotate against the corresponding locking tabs 96 for proper engagement of the syringe 12 within the syringe port 16. Each lug 34 is configured for being received within the first recess 60 on the first retaining ring 48. The second surface 42 of each lug 34 may be guided into alignment with the first recess 60 along the guiding surface 65 to enable the insertion of the lug 34 into the first recess 60.

FIG. 4C shows another embodiment in which the one or more locking tabs 96 are formed on the top surface 38 of at least one of the lugs 34. In other embodiments, the one or more locking tabs 96 may be formed separately from the lugs 34. In other embodiments, locking tabs 96A may be provided on both the at least one lugs 34 of syringe 12 and at least one retaining member 58 of the syringe port 16.

FIG. 4D shows a cylindrical plan projection view of an embodiment of the syringe 12 and syringe port 16 shown in FIGS. 3A-3E. FIG. 4E shows a further embodiment in which some, but not all, of the first and second lugs 34, 37 have been removed. In FIG. 4J, the locking elements 112 on the third retaining ring 108 do not have the inclined surface 116 shown in FIGS. 4D-4E. Instead, a space SS is provided between the locking elements 112 and the sidewall 58 for inserting the point 44 of the first lugs 34. In each of these embodiments, at least one first lug 34 is provided.

FIG. 4F shows another embodiment with eight fold symmetry. A benefit of higher symmetry arrangements is that a lower rotational angle of the syringe 12 is necessary for installation and removal. For example, with eight fold symmetry, the rotation of the syringe 12 for removal and ejection can be 22.5 degrees or less. The additional lugs also spread the holding or restraining force more evenly around the syringe barrel 18. In other embodiments, the connection between the syringe 12 and the syringe port 16 may have 8-fold, 10-fold, 12-fold, 16-fold, or any other symmetry.

With reference to FIG. 4G, the lugs 34 have a generally triangular shape with a pair of second surfaces 42 tapering axially to a point 44. The second surfaces 42 are configured to engage the guiding surfaces 65 on the first retaining ring 48 to self-guide the lugs 34 into the first recess 60. The second retaining ring 78 has second recesses 88 shaped correspondingly to receive the lugs 34. At least some of the first locking elements 84 have a ramp 89 to guide the lugs 34 toward the second recess 88 as the syringe 12 is inserted proximally within the syringe port 16. In FIG. 4H, the lugs 34 have a triangular shape with at least one surface that is substantially parallel to the longitudinal axis 15 (shown in FIG. 3A). The second retaining ring 78 has second recesses 88 shaped correspondingly to receive the lugs 34. In FIG. 4I, the lugs 34 have an integral locking tab 96.

Figure 5A:
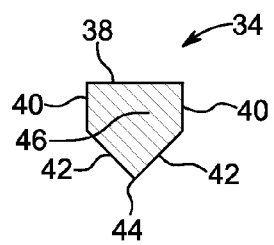
FIGS. 5A-5Z show various embodiments of syringe retaining members on a syringe.
Figure 5B:
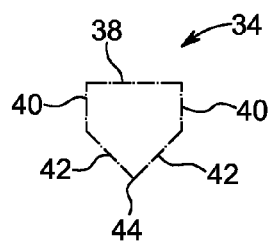
Figure 5C:
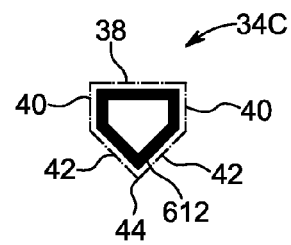
Figure 5D:
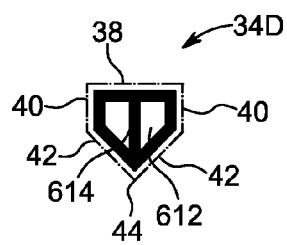
Figure 5E:
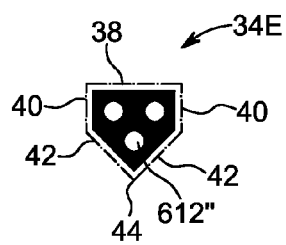
Figure 5F:
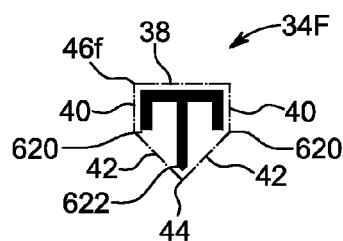
Figure 5G:
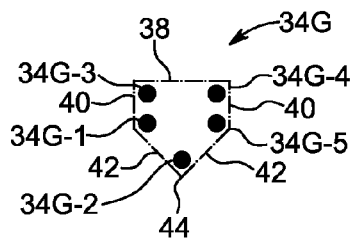
Figure 5H:
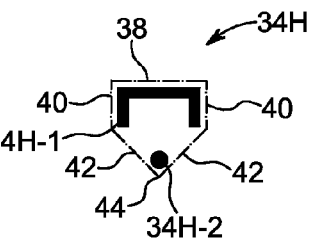
Figure 5I:
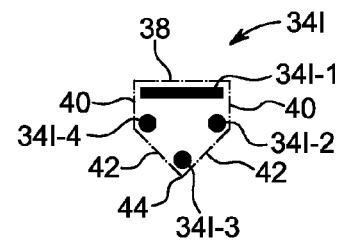
Figure 5J:
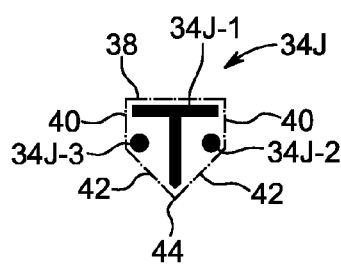
Figure 5K:
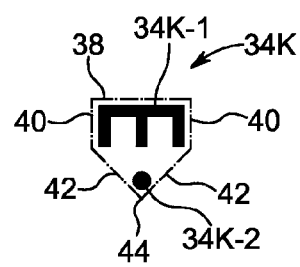
Figure 5L:
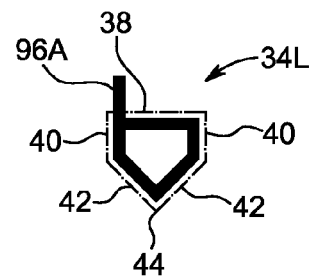
Figure 5M:
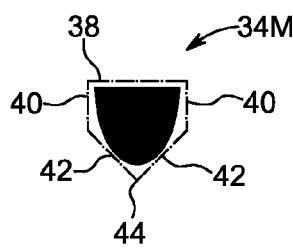
Figure 5N:
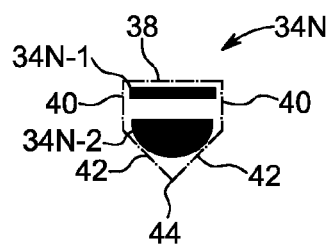
Figure 5O:
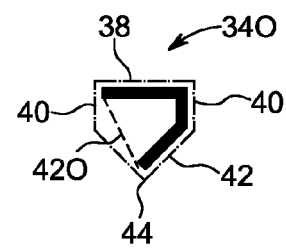
Figure 5P:
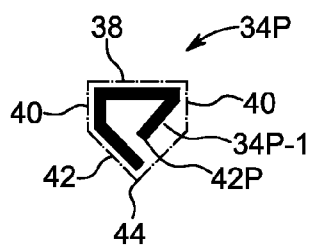
Figure 5Q:
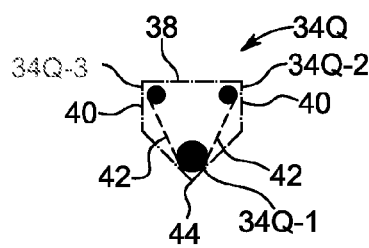
Figure 5R:
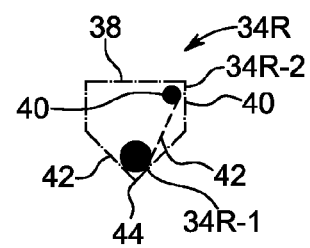
Figure 5T:
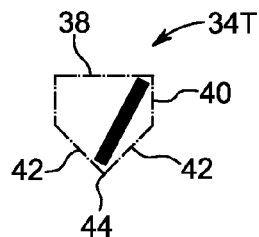
Figure 5U:
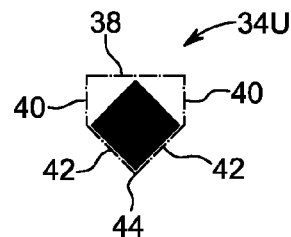
Figure 5V:
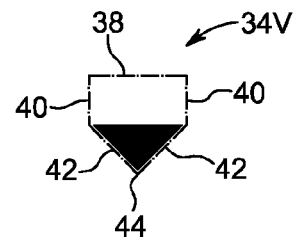
Figure 5W:
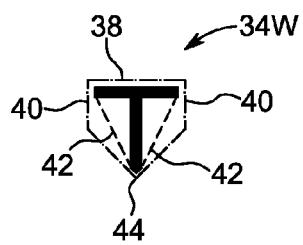
Figure 5X:
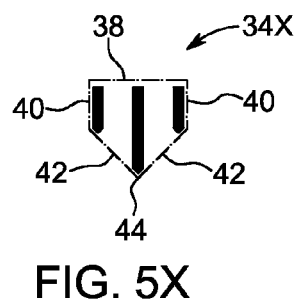
Figure 5Y:
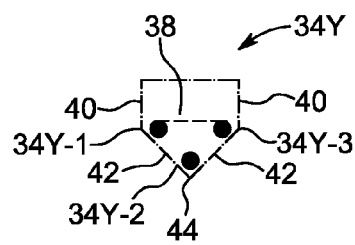
Figure 5Z:
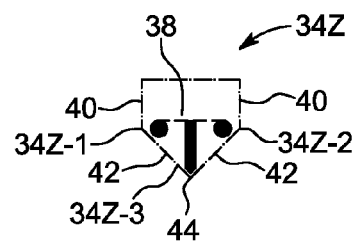

FIGS. 5A-5Z illustrate various embodiments of the lug 34. FIG. 5A shows an example lug 34 having the configuration described herein with reference to FIGS. 2A-2D, while FIG. 5B illustrates an outline of the lug 34 with a dotted line indicating each of the surfaces of the lug 34.

FIG. 5C shows an example of a lug 34c in which the center section 612 has at least one radially inwardly recessed hollow portion and the lug 34c is defined by perimeter surfaces. In some embodiments, the center section 612 may have a thickness that corresponds to the thickness of the syringe barrel 18 (shown in FIG. 3A). In other embodiments, the center section 612 may have a thickness that is greater or less than the thickness of the syringe barrel 18 (shown in FIG. 3A). In some embodiments, the hollow center section 612 extends only through a portion of the sidewall thickness of the syringe barrel 18. The perimeter surfaces may be connected together or have one or more gap therebetween. One benefit of having at least one radially inwardly recessed hollow center section 612 is that sinking of the plastic material can be reduced or eliminated as the material cools during molding. With reference to FIG. 5D, one or more reinforcing members 614 may be provided in the center section 612. The one or more reinforcing members 614 may be connected to or separated from the perimeter surfaces of the lug 34D. In cases where the retention force needs to be high and thus there is significant stress on the surface of the lug 34D, the presence of additional material or reinforcing members, for example one or more reinforcing members 614, can allow the lug 34D to operate under such higher forces. FIG. 5E shows a lug 34E in which a plurality of radially inwardly recessed hollow portions 612" are provided. In some embodiments, the voids 612" may have a substantially circular shape; however, various other shapes may be readily implemented.

FIG. 5F illustrates a lug 34F in which the second surfaces 42 are not physical surfaces but are virtual surfaces defined by the dashed lines extending between points 620 and 622. These virtual surfaces taper axially in a manner described herein with reference to the first and second surfaces 40, 42 on the lug 34 shown in FIGS. 2A and 3A.

According to certain embodiments, lug 34 may be a combination of a plurality of lugs that together form the surfaces of lug 34 which can be a combination of physical surfaces and/or virtual surfaces. FIG. 5G shows an embodiment where the lug 34G is an assembly of a plurality of lugs 34G-1 to 34G-5. As shown with the dotted lines in FIG. 5G, the functional surfaces of the lug 34G are defined by the interaction of two or more of the lugs 34G-1 to 34G-5. The second surfaces 42 are not physical surfaces but are virtual surfaces defined by the dashed lines extending between 34G-1 and 34G-2 and between 34G-4 and 34G-5. These virtual surfaces taper axially in a manner described herein with reference to the first and second surfaces 40, 42 on the lug 34 shown in FIG. 2A.

FIG. 5H shows a lug 34H having a pair of lugs 34H-1 and 34H-4. In the embodiment of FIG. 5H, the base surface 38 and the first surfaces 40 are formed on the lug 34H-1, while point 44 is a surface of lug 34H-2. The second surfaces 42 are virtual surfaces formed between the two lugs 34H-1 and 34H-2. These virtual surfaces taper axially in a manner described herein with reference to the first and second surfaces 40, 42 on the lug 34 shown in FIG. 2A.

FIG. 5I shows a lug 34I having four lugs 34I-1 to 34I-2. In the embodiment of FIG. 5I, the base surface 38 is formed on the lug 34I-1, while point 44 is a surface of lug 34I-3. The first surfaces 40 are virtual surfaces formed between 34I-1 and 34I-2, and between 34I-2 and 34I-4. The second surfaces 42 are virtual surfaces formed between 34I-2 and 34I-3, and between 34I-3 and 34I-4. These virtual surfaces taper axially in a manner described herein with reference to the first and second surfaces 40, 42 on the lug 34 shown in FIG. 2A.

FIG. 5J shows a lug 34J having a T-shaped central lug 34J-1 and a pair of lateral lugs 34J-2 and 34J-3. In the embodiment of FIG. 5J, the base surface 38 is formed on the top surface of the lug 34J-1, while point 44 is on the bottom surface of the lug 34J-1. The first surfaces 40 are virtual surfaces formed between a top portion of 34J-1 and 34J-2, and between the top portion of 34J-1 and 34J-3. The second surfaces 42 are virtual surfaces formed between a bottom portion of 34J-1 and 34J-2, and between the bottom portion of 34J-1 and 34J-3. FIG. 5W shows a T-shaped lug 34W without the pair of lateral lugs shown in FIG. 5J. In FIG. 5W, the second surfaces 42 are virtual surfaces formed between the top portion of lug 34W and the bottom portion at the point 44. These virtual surfaces taper axially in a manner described herein with reference to the first and second surfaces 40, 42 on the lug 34 shown in FIG. 2A.

FIG. 5K shows a lug 34K having an upper lug 34K-1 and a lower lug 34K-2. In the embodiment of FIG. 5K, the base surface 38 is formed on the top surface of the lug 34K-1, while point 44 is represented by the lug 34K-2. A pair of first surfaces 40 extends along lateral portions of 34K-1 and 34K-2. The second surfaces 42 are virtual surfaces formed between a terminal portion of the first surfaces 40 and 34K-2. These virtual surfaces taper axially in a manner described herein with reference to the first and second surfaces 40, 42 on the lug 34 shown in FIG. 2A.

FIG. 5L shows a lug 34L having a shape similar to the shape of lug 34C described herein with reference to FIG. 5C. Lug 34L further has an integrated locking tab 96a extending from a portion of the base surface 38.

FIG. 5M shows a lug 34M having a substantially linear base surface 38 and curved first and second surfaces 40, 42. The first and second surfaces 40, 42 may be curved to have a substantially elliptical form. The first and second surfaces 40, 42 taper axially in a curvilinear form to point 44. FIG. 5N shows a lug 34N having a shape similar to that of lug 34M shown in FIG. 5M. The lug 34N is formed from an upper lug 34N-1 and a lower lug 34N-2. The upper lug 34N-1 defines a substantially linear base surface 38, while the lower lug 34N-2 is spaced apart from the upper lug 34N-1 by a gap and has a substantially curved shape that tapers axially inwardly along the second surfaces 42.

FIGS. 5O-5P show lugs 34O, 34P having a shape similar to the shape of lug 34C described herein with reference to FIG. 5C. Lugs 34O, 34P have at least one of the first or second surfaces 40, 42 removed such that lugs 34O, 34P have a discontinuous outline with at least one virtual second surface 42O extending between the point 44 and the first surface 40. This virtual second surface 42O tapers axially in a manner described herein with reference to the first and second surfaces 40, 42 on the lug 34 shown in FIG. 2A.

FIG. 5Q shows a lug 34Q formed from three circular lugs 34Q-1 to 34Q-3. The circular lugs 34Q-1 to 34Q-3 are positioned such that virtual surfaces are defined therebetween. In particular, a pair of second virtual surfaces is defined by the pair of upper circular lugs 34Q-2 and 34Q-3 and the lower circular lug 34Q-1. The lugs 34Q-1 to 34Q-3 may have any other shape, such as oval, square, triangular, rhomboid, or other polygonal shape. Each virtual second surface 42 tapers axially in a manner described herein with reference to the first and second surfaces 40, 42 on the lug 34 shown in FIG. 2A. FIG. 5R shows a lug 34R having a shape formed from two circular lugs 34R-1 to 34R-2 with a single virtual second surface 42 defined therebetween. The lugs 34R-1 to 34R-2 may have any other shape, such as oval, square, triangular, rhomboid, or other polygonal shape. FIG. 5Y shows a lug 34Y formed from three circular lugs 34Y-1 to 34Y-3 where the upper pair of lugs 34Y-1 and 34Y-2 is closer axially to the lower lug 34Y-3 than in the lug embodiment 34Q described with reference to FIG. 5Q. In FIG. 5Z, the lower lug 34Z-3 of lug 34Z is represented as a rectangular element rather than a circular element.

With reference to FIGS. 5S(1)-5S(3), a pair of lugs 34SA and 34SB is provided on separate lugs 34 separated by the outer surface 21 of the barrel 18. On the first lug 34SA, a single lug 34S-1 is provided in an upper corner, for example the upper right corner of the outline of lug 34 where a virtual base surface 38 is joined with a virtual first surface 40. The first lug 34SA is configured to engage the locking tab 96 provided on the first retaining ring 48 of the locking mechanism 35 when the syringe 12 is inserted into the syringe port 16 (as shown in cylindrical plan projection FIG. 5S(3)). The second lug 34SB is formed as a single lug 34S-2 located at the point 44. The second lug 34SB is configured to self-orient and guide the syringe 12 into the syringe port 16 by engaging the guiding surface 65 on the first retaining ring 48. The lugs 34S-1 and 34S-2 may have a circular, oval, triangular, square, rectangular, or other polygonal shape.

With reference to FIG. 5T, the lug 34T is formed as a rectangular second surface 42 that tapers axially from the base surface 38 to the point 44. This second surface 42 tapers axially in a manner described herein with reference to the first and second surfaces 40, 42 on the lug 34 shown in FIG. 2A.

With reference to FIG. 5U, the lug 34U is shaped as a square lug having two sides aligned along the direction of tapered second surfaces 42. FIG. 5V shows a triangular lug 34V having two sides aligned along the direction of tapered second surfaces 42. In other embodiments, lug 34V may include at least one second lug defining the base surface 38. The second surfaces 42 in FIGS. 5T-5V taper axially in a manner described herein with reference to the first and second surfaces 40, 42 on the lug 34 shown in FIG. 2A.

FIG. 5X shows a lug 34X having a plurality of parallel elements spaced apart horizontally relative to a vertical axis. A virtual second surface 42 is defined between at least two adjacent parallel elements. The second surface 42 in FIG. 5X tapers axially in a manner described herein with reference to the first and second surfaces 40, 42 on the lug 34 shown in FIG. 2A. Some embodiments of syringe 12 may include various combinations of any of lugs 34A through 34X and/or 10A through 10 H in the at least one syringe retaining members 32.

Figure 6A:
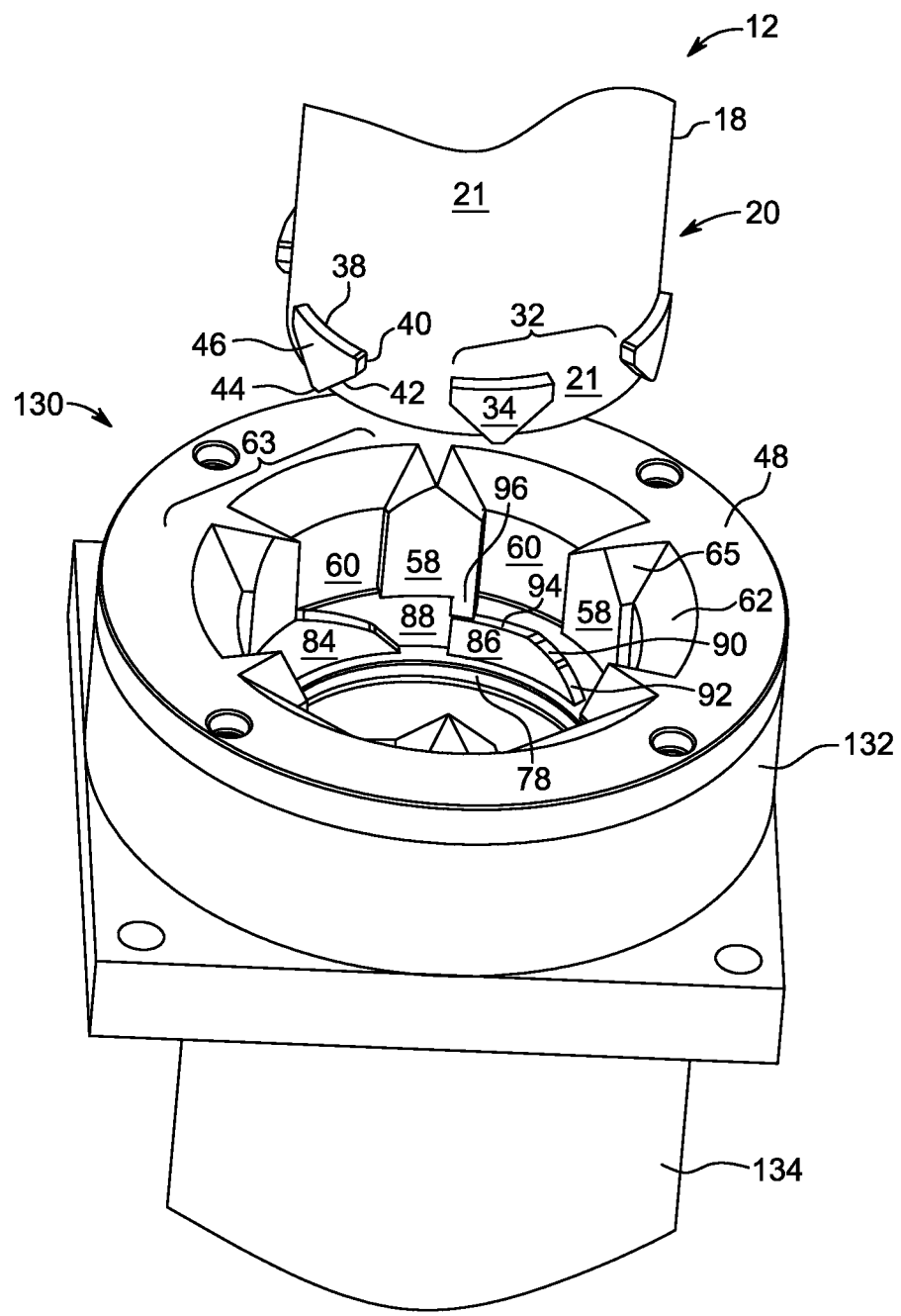
FIG. 6A is a perspective view of a coupling configured for connecting a syringe of the present disclosure to an injector.

With reference to FIG. 6A, a coupling 130, including a mounting member therefor, can be fabricated to be separate from and attachable to the syringe barrel 18. The coupling 130 can, for example, be configured to accept the syringe 12 having at least one syringe retaining member 32 described herein and to adapt the syringe 12 for use with a fluid injector having a syringe port with a locking mechanism not configured to receive the at least one syringe retaining member 32. For example, the coupling 130 can adapt the syringe 12 for use with the fluid injector described in U.S. Pat. No. 5,383,858 or U.S. Pat. No. 6,652,489, or any other fluid injector. In some embodiments, the coupling 130 is releasably connectable to the injector. In other embodiments, the coupling 130 may be inserted into and retained in a locking mechanism of the fluid injector. The coupling 130 may also be releasably connected or attached to the syringe 12 independently of the attachment of the coupling to the injector.

Figure 7A:
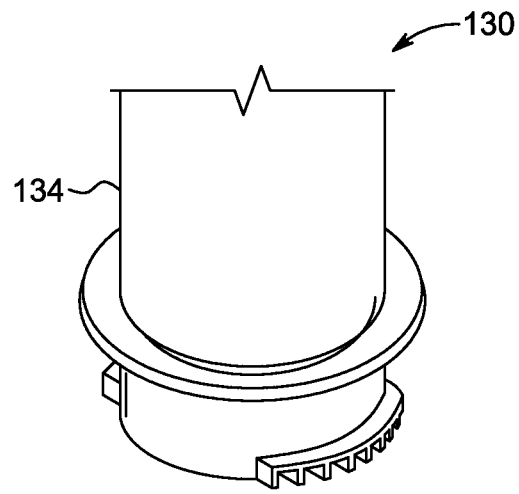
FIGS. 7A-7B are perspective views of alternative embodiments of connection portions of the coupling shown in FIG. 6A.
Figure 7B:
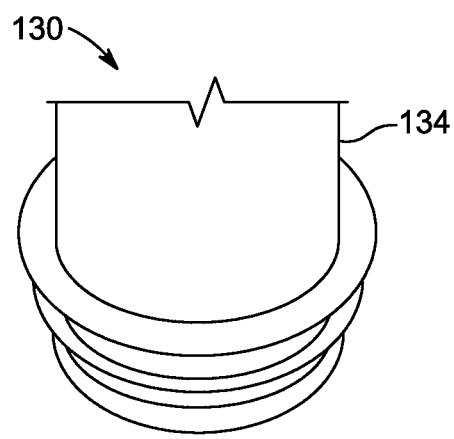

With reference to FIG. 6A, the coupling 130 has a first portion 132 configured for receiving a syringe 12 having at least one syringe retaining member 32, according to an embodiment described herein, and a second portion 134 configured for loading into an injector having a syringe port which is not configured to receive the syringe 12 having at least one syringe retaining member 32 according to an embodiment described herein. The first portion 132 may be directly connected and monolithically formed with the second portion 134. In some embodiments, the first portion 132 may be releasably connected to the second portion 134 such that various second portions (shown in FIGS. 7A-7B) may be used with the first portion 132. With continued reference to FIG. 6A, the first portion 132 has a locking mechanism 35 described herein with reference to FIGS. 2A-2D. In other embodiments, the first portion 132 may have a locking mechanism 35 described with reference to FIGS. 3A-3H. In various embodiments, the first portion 132 of the coupling 130 is configured for releasably receiving the syringe 12 having a corresponding at least one syringe retaining member 32, as described herein. With reference to FIGS. 7A-7B, the second portion 134 of the coupling 130 may have a connection interface configured for connecting with an injector that would otherwise not be capable of receiving the syringe 12 having a syringe retaining member 32 described herein. FIG. 7A shows the second portion 134 configured for use with an engagement mechanism of the injector described in U.S. Pat. No. 5,383,858, while FIG. 7B shows the second portion 134 configured for use with an engagement mechanism of the injector described in U.S. Pat. No. 6,652,489. The second portion 134 may be configured to interface with various other injectors not expressly described herein. In some embodiments, the coupling 130 may have a separate mechanism for engaging and disengaging the coupling 130 to and from a locking mechanism of the injector.

Figure 6B:
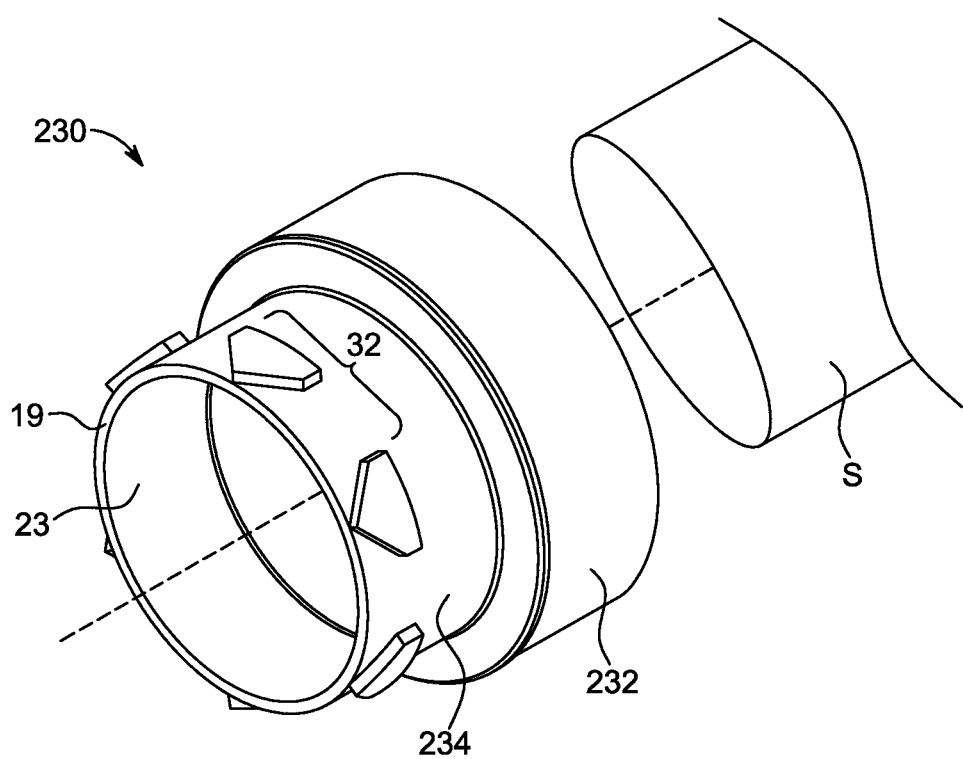
FIG. 6B is a perspective view of an adapter configured for connecting a syringe to an injector of the present disclosure.

With reference to FIG. 6B, an adapter 230 may be configured to receive a syringe S not having one or more syringe retaining members 32 described herein for removably connecting with an injector having the locking mechanism 35 in accordance with one of the embodiments described herein. In various embodiments, the adapter 230 may be configured for connecting to a syringe S for subsequent installation on an injector. For example, the adapter 230 may be connected to the non-compatible syringe S releasably or permanently. Such an adapter 230 may have a connection interface having at least one engagement member 32 in accordance with embodiments described herein. The adapter 230 may be configured for being releasably connectable with an injector having a locking mechanism 35 described herein. The adapter 230 and the syringe S may be connected prior to connecting to the injector, or the adapter 230 may be connected to the injector before the syringe S is connected to the adapter 230. The adapter 230 and syringe S may be removed from the injector after use, with the adapter 230 being disposed of with the syringe S, or being removed from the used syringe S and saved for subsequent use with a different syringe S.

In one embodiment, a first portion 232 of the adapter 230 may be configured for permanently or releasably receiving the syringe S, which is not compatible for use with any of the locking mechanisms 35 described herein. In some embodiments, the syringe S may be the syringe described in U.S. Pat. No. 5,383,858 or U.S. Pat. No. 6,652,489, or any other syringe type. The adapter 230 allows the non-compatible syringe S to engage and be retained by the locking mechanisms 35 described herein. In some embodiments, the adapter 230 may have a separate mechanism for engaging and disengaging the syringe S while the adapter 230 remains connected to the locking mechanism 35 of the injector 10. The first portion 232 may also be a cradle or sleeve to hold or retain other syringes S, for example hand held syringes or syringes having different retention mechanisms or features and allowing them to engage and be retained by locking mechanisms 35. A second portion 234 of the adapter 230 may have at least one syringe retaining member 32 in accordance with embodiments described herein. In some embodiments, the at least one syringe retaining member 32 may have one or more lugs 34 described herein with reference to FIGS. 2A-5Z and 10A-10H. The second portion 234 of the adapter 230 may be configured for being releasably connectable with an injector having a locking mechanism 35 described herein. In this manner, various non-compatible syringes S may be used with an injector having a locking mechanism 35 described herein. In various embodiments, the adapter 230 may be configured for connecting a pressure jacket (not shown) to the injector for use in injection procedures requiring high pressure. For example, the adapter 230 having the pressure jacket may be configured for being releasably connectable with an injector. Such an adapter 230 may have a connection interface having at least one syringe retaining member 32 in accordance with one of the embodiments described herein or alternatively have a connection interface that allows non-compatible syringes to be used with the injector. The adapter 230 may be configured for being releasably, permanently, or semi-permanently connectable with an injector having a locking mechanism 35 described herein and allowing syringes S having alternate retaining mechanisms to be used with the injector.

Once connected with the injector, the syringe S may be loaded into the adapter 230 or the pressure jacket and be retained therein at its proximal or distal end.

Figure 4M:
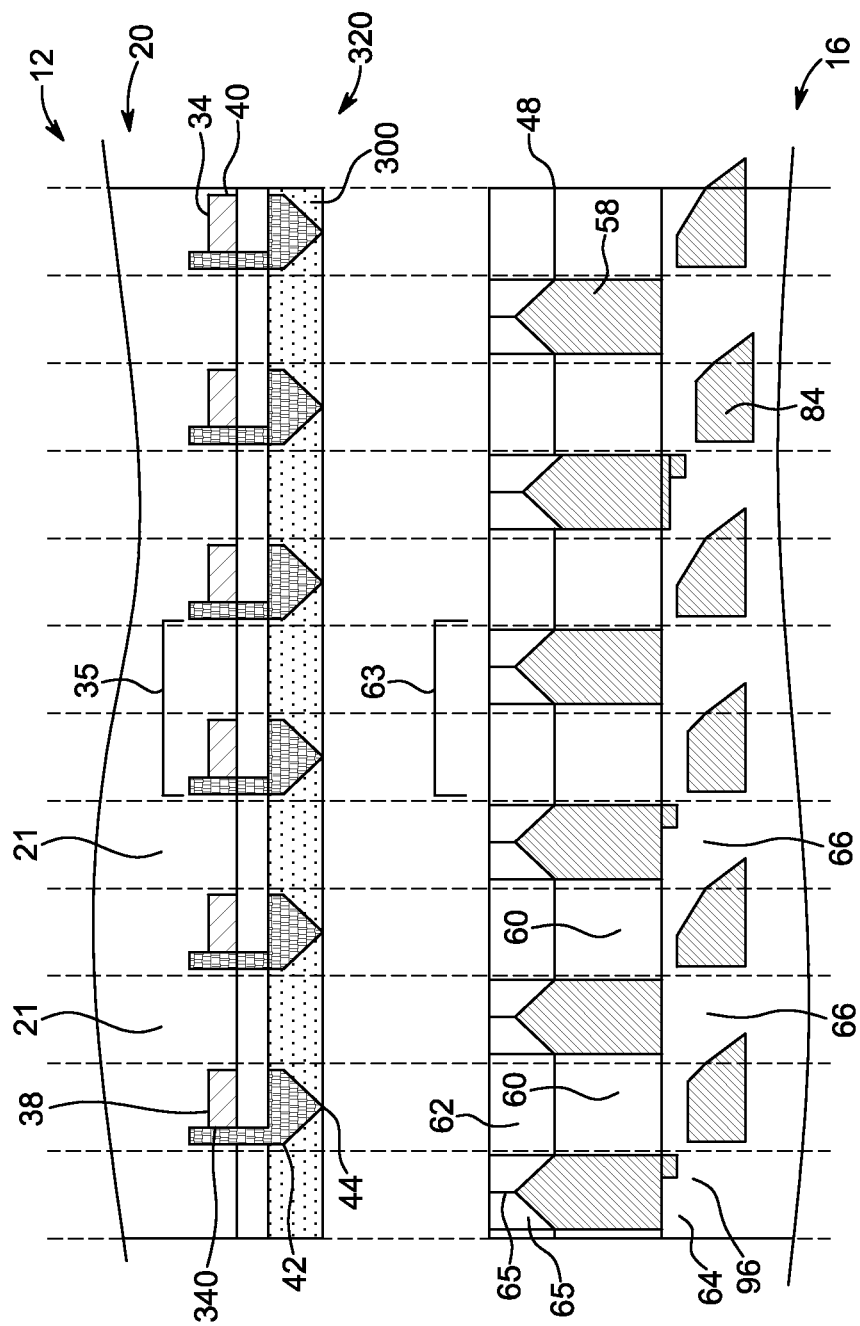

In various embodiments, an adapter 230 may be configured for connecting a syringe 12 having some but not all of the features necessary for subsequent installation into an injector 10 described herein. For example, with reference to FIG. 4L, an adapter 320 may be a ring 300 that provides surfaces 42 and 44 and mates with a syringe that has one or more lugs with at least a base surface 38 for retention within locking mechanism 35. According to this embodiment, the ring 300 may be inserted in syringe port 16 and remain therein for use with subsequent syringes. The adapter 320 allows a syringe which could not by itself mate or function fully with the syringe port 16 to mate and at least perform the retention function with the locking mechanism 35. FIG. 4M shows another embodiment of an adapter 320 having a ring with prominences 340 that extend distally out of the syringe port 16. These prominences 340 can be combined or connected, for example to form a ring extending radially outward from the syringe port 16. By rotating the adapter 320, the syringe 12 and the adapter 320 may be released from the syringe port 16. Similarly upon insertion, to the adapter 320 may be pushed proximally for engagement with the syringe 12.

Figure 8A:
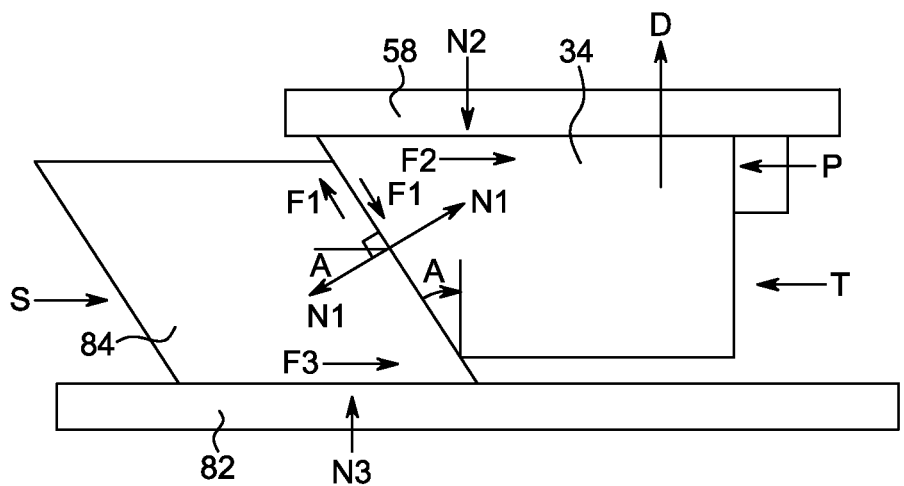
FIG. 8A is a schematic diagram of forces on an embodiment of a syringe retaining member and connection interface during ejection of a syringe from a fluid injector.
Figure 8B:
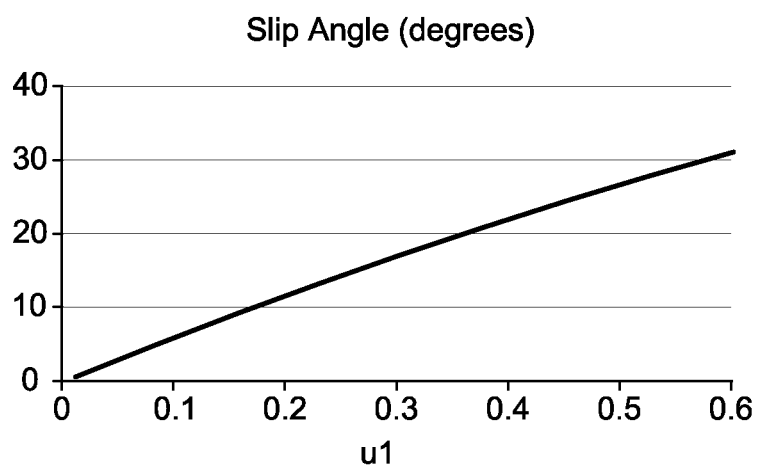
FIG. 8B is a graph of a slip angle for syringe ejection as a function of a coefficient of friction between a syringe retaining member and a locking mechanism.
Figure 8C:
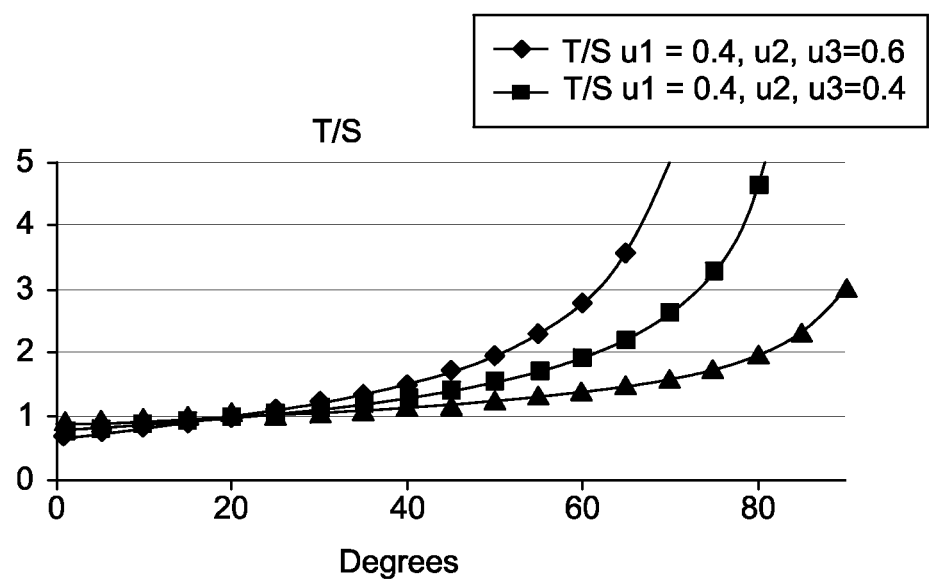
FIG. 8C is a graph of a ratio of a rotational force on a syringe during ejection relative to a restoring force of a locking mechanism as a function of an angle of tapered surfaces at a connection interface.

FIG. 8A is an illustration of a generalized free body diagram of forces present during ejection of the syringe 12 from the syringe port 16. A normal force N1 and a frictional force F1 of the lug 34 act against the first locking element 84, and a normal force N2 and a frictional force F2 of the lug 34 act on the retention surface of sidewall 58 as well as the force T applied by the user to rotate the syringe 12 and any force D urging the syringe 12 distally provided by the drip flange or other means. In some embodiments, the syringe 12 may be made from a polyethylene terephthalate (PET) material, while the first locking element 84 may be made from a polyoxymethylene (POM) material, such as DELRIN™. The coefficient of friction $\mu$ of DELRIN™ on another DELRIN™ surface is approximately 0.4. Using this value, a practical limit of the angle A to enable ejection is approximately 20 degrees relative to a direction of the longitudinal axis 15 of the syringe 12. Thus for angles greater than 20 degrees, there will be slip and upon sufficient motion for the lugs 34 to clear the projections, the syringe 12 will be ejected and pop distally in the syringe port (FIG. 8B). FIG. 8C shows that the ratio of the force T to rotate the syringe 12 to the restoring force S of the resilient member 102 increases as the angle A increases. The ratio remains substantially constant as the angle increases for low angle values, but then increases significantly at higher angles. In some examples, an angle of at least 30 degrees and less than approximately 60 degrees may be used.

Figure 9A:
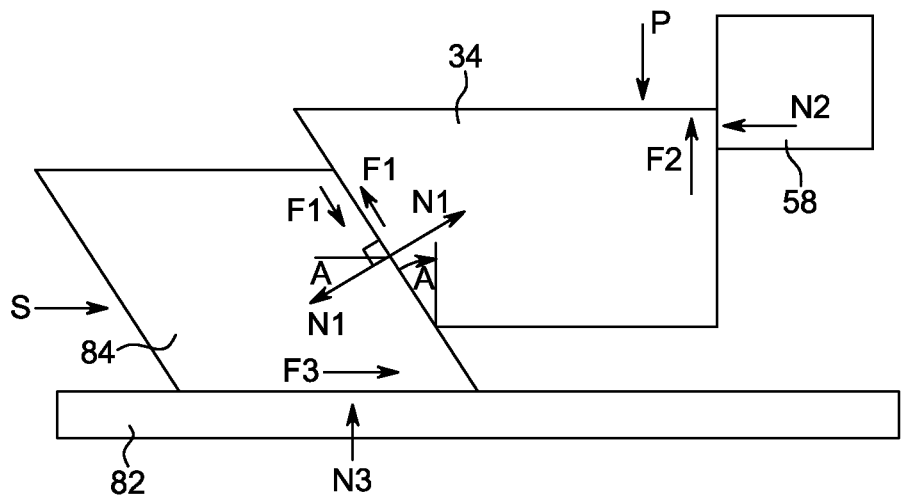
FIG. 9A is a schematic diagram of forces on an embodiment of a syringe retaining member and connection interface during an insertion of a syringe into a fluid injector.
Figure 9B:
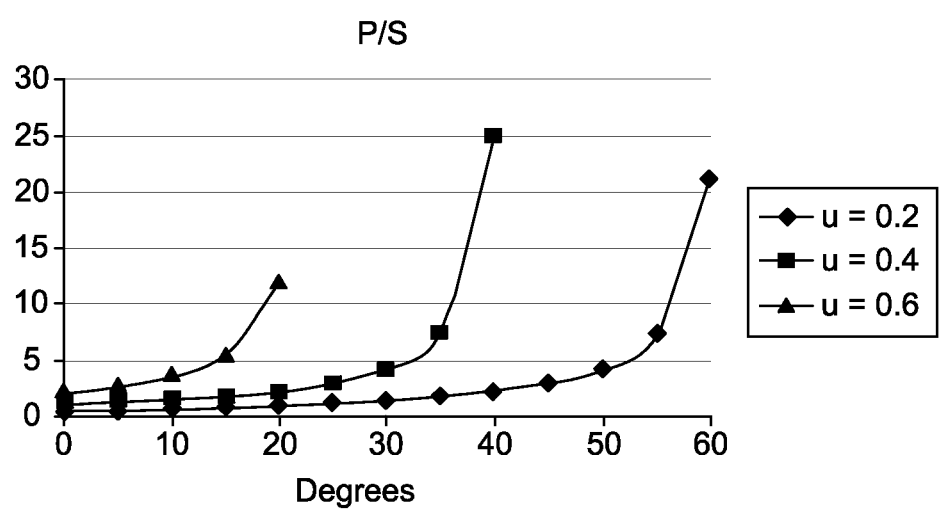
FIG. 9B is a graph of a slip angle for syringe ejection as a function of a coefficient of friction between a syringe and a locking mechanism.

FIG. 9A is an illustration of a generalized free body diagram of forces acting at the interface during the insertion of the syringe 12 into the syringe port 16. The one or more lugs 34 interact with the one or more first locking elements 84 due to a lateral force P provided by the user. During the rotation, the one or more lugs 34 are in sliding contact with the sidewall 58. In addition, the second retaining ring (not shown) slides over the bottom surface 82 of the housing. Performing a static force analysis on this generalized interaction provides an estimate of the force for insertion as a function of the angle A of the interaction of the two surfaces for various coefficients of friction $\mu$ between the surfaces, as shown in FIG. 9B.

Figure 10A:
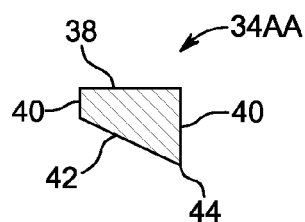
FIGS. 10A-10H show various embodiments of syringe retaining members on the syringe.
Figure 10B:
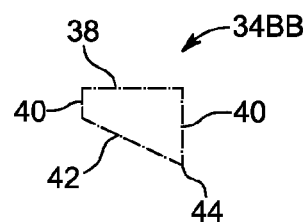
Figure 10C:
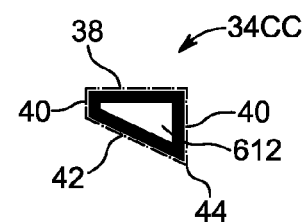
Figure 10D:
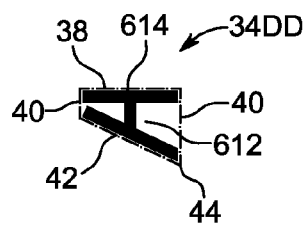
Figure 10E:
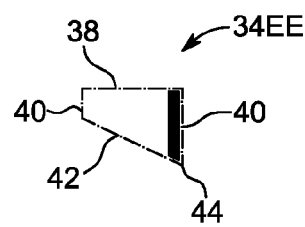
Figure 10F:
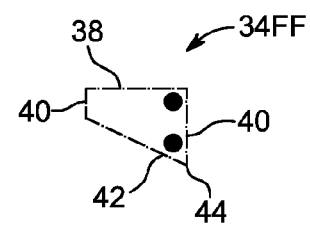
Figure 10G:
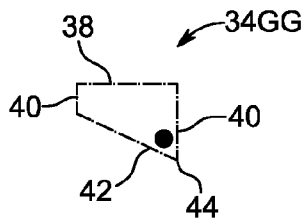
Figure 10H:
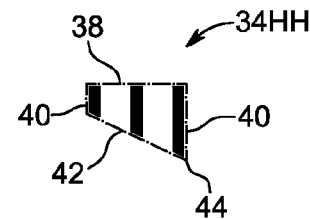

FIGS. 10A-10H, illustrate various embodiments of the lug 34 for use with various embodiments of the locking mechanisms 35 described herein. FIG. 10A shows an example lug 34AA having the configuration described herein with reference to FIGS. 3A-3H, while FIG. 10B illustrates an outline of the lug 34BB with a dotted line indicating each of the surfaces of the lug 34. FIG. 10C shows an example of a lug 34CC in which the center section 612 includes a radially inwardly recessed hollow portion and the lug 34CC is defined by perimeter surfaces. In some embodiments, the center section 612 may have a thickness that corresponds to the thickness of the syringe barrel 18 (shown in FIG. 3A). In other embodiments, the center section 612 may have a thickness that is greater or less than the thickness of the syringe barrel 18 (shown in FIG. 3A). The perimeter surfaces may be connected together or have one or more gap therebetween. One benefit of having at least one radially inwardly recessed hollow center section 612 is that sinking of the plastic material can be reduced or eliminated as the material cools during molding. With reference to FIG. 10D, one or more reinforcing members 614 may be provided in the center section 612, which has two peripheral gaps as mentioned above. The one or more reinforcing members 614 may be connected to or separated from the perimeter surfaces of the lug 34DD. In cases where the retention force needs to be high and thus there is significant stress on the surface of the lug 34DD, the presence of additional material or reinforcing members, for example one or more reinforcing members 614, can allow the lug 34EE to operate under such higher forces. FIG. 10E shows a lug 34EE having a single vertical or longitudinal member, for example defining surface 40, point 44, and base surface 38. FIG. 10F shows a lug 34FF having two generally rounded lugs, for example defining surface 40, point 44, and base surface 38. FIG. 10G shows a lug 34GG having one rounded lug. The bottom of lug 34GG defines the point 44 and the top defines the base surface 38. FIG. 10H shows a lug 34HH assembled from three generally vertical and parallel lugs with an even top surface which form the base surface 38 and tapered bottom surface. It should be noted that one or more variations of the lugs 34 shown in FIGS. 5 and 10 or other variations are within the scope of this disclosure can operate with one or more variations of the syringe ports 16 that are within the scope of this disclosure.

With reference to FIG. 1B, a system may be provided to transmit information from the syringe 12 to the injector 10 (shown in FIG. 1A). In one embodiment, the syringe 12 may be provided with one or more encoding devices 49 for example, on one or more of the syringe retaining members 32. In other embodiments, the one or more encoding devices 49 may be provided on the outer surface 21 (shown in FIG. 1B), the inner surface 23 (shown in FIG. 1B), within at least a portion of the sidewall 19 (shown in FIG. 1B) of the proximal end 20 of the syringe 12, or on the plunger 26. In some embodiments, the encoding device 49 may be an optically readable member, such as a barcode, while in other embodiments, the encoding device 49 may be an RFID tag, near-field communication device, or any other suitable encoding device. A plurality of encoding devices 49 may be disposed around an inner or outer circumference of the syringe 12 and/or the plunger 26. At least one sensor 51 (shown in FIG. 2A) may be provided on the syringe port 16 to read the encoding device 49. In some embodiments, the at least one sensor 51 may be provided on at least one second recess 88. Examples of information which could be encoded on encoding device 49 include, without limitation, dimensions of syringe 12, volume of syringe 12, content of the syringe 12 (in the case of a pre-filled syringe), manufacturing information such as lot numbers, dates and tool cavity number, recommended contrast media flow rates and pressures, and/or loading/injection sequences. In one embodiment, the presence, absence, or shape of one or more syringe retaining members 32 may serve as the encoding device. For example, one absent syringe retaining members 32 may represent a first code. Two or more adjacent absent syringe retaining members 32 may represent a second code. Two or more non-adjacent absent syringe retaining members 32 may represent a third code. Various other combinations of present/absent or differently shaped syringe retaining members 32 may represent various other codes. The presence or absence of individual syringe retaining members 32 can be determined by the injector using mechanical switches, electrical material sensors, optically, visually, or by other means know in the sensing art. This syringe encoding information is communicated to the injector control for communication to the operator and for subsequent use in correctly programming and controlling the injector.

In some embodiments, at least a portion of the injector 10 (shown in FIG. 1A), such as the base 70 of the locking mechanism 35 shown in FIGS. 2A and 3A, may have an inner support ring (not shown) that protrudes into at least a portion of the interior volume 25 of the proximal end 20 of the syringe 12. Such a support ring may be removably extendable into at least a portion of the interior volume 25. The support ring may provide radial and axial support to at least a portion of one or more syringe retaining members 32 and/or the inner sidewall 23 (shown in FIG. 1B) of the syringe 12 when the syringe 12 is inserted into the locking mechanism 35. In embodiments where at least one sensor 51 is provided on the syringe port 16, such as shown in FIG. 2A, the support ring may provide a contrasting surface for detecting the presence or absence of the at least one encoding device 49 on syringe 12. For example, the support ring may provide a contrasting opaque surface against a translucent or transparent sidewall 19 of the syringe 12 to facilitate the detection of the at least one encoding device 49.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

We claim:

1. A syringe comprising:
    a barrel having a proximal end, a distal end, and a sidewall extending substantially circumferentially between the proximal end and the distal end along a longitudinal axis; and
    at least one syringe retaining member having at least one lug protruding radially outwardly relative to an outer surface of the sidewall, the at least one lug tapering axially along the outer surface of the sidewall in a direction from the distal end toward the proximal end,
    wherein the at least one lug is configured for engagement with a locking mechanism on a fluid injector to releasably lock the syringe with the fluid injector, and
    wherein a taper of the at least one lug rotationally guides the syringe into self-orienting alignment with the locking mechanism and axially ejects the syringe upon rotation of the syringe.

2. The syringe of claim 1, wherein the at least one lug comprises a first surface tapered axially along the outer surface of the sidewall in the direction from the distal end toward the proximal end.

3. The syringe of claim 2, wherein the at least one lug further comprises a second surface tapered axially along the outer surface of the sidewall in a direction opposite the first surface.

4. The syringe of claim 3, wherein the at least one lug further comprises a base surface arranged substantially perpendicularly relative to the longitudinal axis.

5. The syringe of claim 4, wherein the at least one lug further comprises at least one surface connecting the first surface and the second surface to the base surface.

6. The syringe of claim 4, wherein at least one of the first surface, the second surface, and the base surface has a shape selected from the group consisting of linear, curved, continuous, discontinuous, and planar.

7. The syringe of claim 1, wherein a plurality of lugs is spaced around at least a portion of the outer surface of the sidewall with equal or unequal angular intervals around the outer surface of the sidewall.

8. The syringe of claim 7, wherein the plurality of lugs is aligned longitudinally at or near the proximal end relative to the longitudinal axis.

9. The syringe of claim 7, wherein at least one of the plurality of lugs is offset toward the proximal end or the distal end of the barrel.

10. The syringe of claim 1, wherein the at least one lug comprises at least one first lug and at least one second lug, and wherein the at least one second lug is same as or different from the at least one first lug.

11. The syringe of claim 10, wherein at least one of the at least one first lug and the at least one second lug comprises an inclined release member protruding from the outer surface of the sidewall to a top surface of the at least one of the at least one first lug and the at least one second lug.

12. The syringe of claim 1, wherein at least one of the at least one lug comprises one or more locking tabs having at least one stop surface for preventing a rotation of the syringe within the locking mechanism.

13. The syringe of claim 1, wherein the at least one of the at least one lug comprises at least one radially inwardly recessed hollow portion.

14. The syringe of claim 1, further comprising at least one flange protruding radially outwardly from the outer surface of the sidewall relative to the longitudinal axis and extending circumferentially around at least a portion of the outer surface of the sidewall.

15. The syringe of claim 14, further comprising a longitudinal stop surface on the at least one flange for limiting a length of a longitudinal insertion of the syringe into the locking mechanism.

16. The syringe of claim 1, wherein the at least one lug has a shape having a triangle-shaped, arrowhead-shaped, rectangular, or rounded outline.

17. A syringe comprising:
a barrel having a proximal end, a distal end, and a sidewall extending substantially circumferentially between the proximal end and the distal end along a longitudinal axis; and
at least one lug protruding radially outwardly relative to an outer surface of the sidewall, the at least one lug having at least one surface tapering axially along the outer surface of the sidewall in a direction from the distal end toward the proximal end,
wherein the at least one lug is configured for engagement with a locking mechanism on a fluid injector to releasably lock the syringe with the fluid injector, and
wherein the at least one surface rotationally guides the syringe into self-orienting alignment with the locking mechanism and wherein the at least one surface axially ejects the syringe upon rotation of the syringe.

18. A syringe comprising:
a barrel having a proximal end, a distal end, and a sidewall extending substantially circumferentially between the proximal end and the distal end along a longitudinal axis; and
a plurality of lugs protruding radially outwardly relative to an outer surface of the sidewall and spaced around at least a portion of the outer surface of the sidewall, at least one of the plurality of lugs comprising:
a first surface tapered axially along the outer surface of the sidewall in a direction from the distal end toward the proximal end;
a second surface tapered axially along the outer surface of the sidewall in a direction opposite the first surface;
a base surface arranged substantially perpendicularly relative to the longitudinal axis; and
at least one surface connecting the first surface and the second surface to the base surface,
wherein at least one of the plurality of lugs is configured for engagement with a locking mechanism on a fluid injector to releasably lock the syringe with the fluid injector, and
wherein at least one of the first surface and the second surface rotationally guides the syringe into self-orienting alignment with the locking mechanism, and
wherein at least one of the first surface and the second surface axially ejects the syringe upon rotation of the syringe.

19. A fluid injection apparatus, comprising:
at least one syringe comprising a cylindrical barrel with a distal end, a proximal end, a sidewall, and a longitudinal axis extending between the distal end and the proximal end, the barrel having at least one lug protruding radially outwardly from an outer surface of the sidewall, the at least one lug having a surface tapered axially in a direction toward the proximal end;
an injector comprising an injector housing defining at least one syringe port for receiving the at least one syringe; and
a locking mechanism associated with the at least one syringe port for securing the at least one syringe within the at least one syringe port, the locking mechanism configured for engaging the at least one lug of the at least one syringe to releasably lock the at least one syringe within the at least one syringe port,
wherein the tapered surface of the at least one lug rotationally guides the at least one syringe into self-orienting alignment with the locking mechanism and axially ejects the at least one syringe upon rotation of the at least one syringe.

20. The fluid injection apparatus of claim 19, wherein the locking mechanism comprises:
a housing having a proximal end, a distal end, and a central opening extending therebetween;
a first retaining ring at the distal end of the housing; and
a second retaining ring within the central opening of the housing between the proximal end of the housing and the first retaining ring,
wherein the second retaining ring is selectively rotatable relative to the first retaining ring to operatively engage the at least one lug of the at least one syringe.

21. The fluid injection apparatus of claim 20, wherein the first retaining ring has at least one first recess configured to receive the at least one lug of the at least one syringe when the proximal end of the at least one syringe is inserted into the at least one syringe port.

22. The fluid injection apparatus of claim 21, wherein the at least one first recess has at least one guide surface for guiding the at least one lug of the at least one syringe into the at least one first recess, and wherein at least one lateral surface of the at least one first recess defines a guide path for guiding a movement of the at least one lug within the at least one first recess.

23. The fluid injection apparatus of claim 22, wherein the at least one guide surface is radially angled or curved relative to the longitudinal axis in a direction from the distal end toward the proximal end of the first retaining ring.

24. The fluid injection apparatus of claim 20, wherein a plurality of lugs is spaced around at least a portion of the outer surface of the sidewall of the at least one syringe, and
    wherein a plurality of first recesses is spaced apart around at least a portion of an inner surface of the first retaining ring.

25. The fluid injection apparatus of claim 20, wherein the second retaining ring has one or more locking elements on at least a portion of an inner sidewall of the second retaining ring.

26. The fluid injection apparatus of claim 25, wherein the one or more locking elements are separated by one or more second recesses.

27. The fluid injection apparatus of claim 26, wherein at least one of the one or more second recesses is configured to receive the at least one lug of the at least one syringe when the proximal end of the at least one syringe is inserted through the first retaining ring.

28. The fluid injection apparatus of claim 20, wherein the first retaining ring comprises one or more first recesses and the second retaining ring comprises one or more second recesses configured for receiving the at least one lug upon rotation of the second retaining ring into selective alignment with the one or more first recesses.

29. The fluid injection apparatus of claim 20, further comprising a third retaining ring between the first retaining ring and the second retaining ring.

30. The fluid injection apparatus of claim 20, wherein at least one elastically resilient member is coupled with the second retaining ring.

\* \* \* \* \*

UNITED STATES PATENT AND TRADEMARK OFFICE
CERTIFICATE OF CORRECTION

PATENT NO.       : 9,173,995 B1  
APPLICATION NO.  : 14/526294  
DATED            : November 3, 2015  
INVENTOR(S)      : Tucker et al.

It is certified that error appears in the above-identified patent and that said Letters Patent is hereby corrected as shown below:

IN THE SPECIFICATION:  
Column 6, Line 59, delete "nearest the to an" and insert -- nearest to an --, therefor.  
Column 17, Line 45, delete "syringe 16" and insert -- syringe 12 --, therefor.  
Column 25, Line 28, delete "syringe 16" and insert -- syringe 12 --, therefor.  
Column 25, Line 32, delete "syringe 16" and insert -- syringe 12 --, therefor.  
Column 32, Line 58, delete "of the housing" and insert -- of housing 70 --, therefor.  
Column 34, Line 16, delete "base 70" and insert -- housing 70 --, therefor.  
Column 34, Line 23, delete "sidewall" and insert -- surface --, therefor.

Signed and Sealed this  
First Day of March, 2016

Michelle K. Lee  
*Director of the United States Patent and Trademark Office*